(12) United States Patent
Van Criekinge et al.

(10) Patent No.: US 9,371,569 B2
(45) Date of Patent: Jun. 21, 2016

(54) DETECTION AND PROGNOSIS OF CERVICAL CANCER

(71) Applicant: MDxHealth SA, Sart-Tilman (BE)

(72) Inventors: Wim Van Criekinge, Sart-Tilman (BE); Valerie Deregowski, Sart-Tilman (BE); Luc Dehaspe, Sart-Tilman (BE); G. Bea A. Wisman, Groningen (NL); Ate G. J. Van der Zee, Groningen (NL); E. M. D. Schuuring, Groningen (NL)

(73) Assignee: MDxHealth S.A., Herstal (BE)

( * ) Notice: Subject to any disclaimer, the term of this patent is extended or adjusted under 35 U.S.C. 154(b) by 0 days.

(21) Appl. No.: 14/180,239

(22) Filed: Feb. 13, 2014

(65) Prior Publication Data

US 2015/0017634 A1    Jan. 15, 2015

Related U.S. Application Data

(63) Continuation of application No. 12/933,747, filed as application No. PCT/EP2009/053386 on Mar. 23, 2009, now abandoned.

(60) Provisional application No. 61/038,549, filed on Mar. 21, 2008.

(51) Int. Cl.
    *C12Q 1/68* (2006.01)

(52) U.S. Cl.
    CPC ........ *C12Q 1/6886* (2013.01); *C12Q 2600/112* (2013.01); *C12Q 2600/154* (2013.01); *C12Q 2600/16* (2013.01)

(58) Field of Classification Search
    None
    See application file for complete search history.

(56) References Cited

U.S. PATENT DOCUMENTS

2005/0250137 A1* 11/2005 Tainsky et al. ............... 435/6
2010/0144836 A1*  6/2010 Van Engeland et al. .... 514/44 A

FOREIGN PATENT DOCUMENTS

WO    WO 2006113678 A2 * 10/2006

OTHER PUBLICATIONS

Widschwendter et al., Gynecologic Oncology, 2004 vol. 93 pp. 407-416.*

* cited by examiner

*Primary Examiner* — Michele K Joike
*Assistant Examiner* — Mindy G Brown
(74) *Attorney, Agent, or Firm* — Andrus Intellectual Property Law, LLP

(57) ABSTRACT

The present invention relates to methods and kits for identifying, diagnosing, prognosing, and monitoring cervical cancer. These methods include determining the methylation status or the expression levels of particular genes, or a combination thereof.

23 Claims, 15 Drawing Sheets

Figure 5B

| Nr | Assay Name | Gene ID | Official Gene Symbol | Refseq | Sense Primer sequence (5' – 3') SEQ ID NO's 337-342 | Antisense Primer sequence (5' – 3') SEQ ID NO's 343-348 |
|---|---|---|---|---|---|---|
| 1 | ALX4_75634 | 60529 | ALX4 | NM_021926 | CGTTAGGTTTTGTTGTTTAGCGT | CGACACAACTTTCCTATCGACC |
| 2 | ALX4_75635 | 60529 | ALX4 | NM_021926 | CGTTAGGTTTTGTTGTTTAGCGT | AACTTTCCTATCGACCGCC |
| 3 | ALX4_75636 | 60529 | ALX4 | NM_021926 | GTTTCGTAGTTTAGCGTTAGAGCGT | AAAACGAATACTTCTTACCGACC |
| 4 | ALX4_75637 | 60529 | ALX4 | NM_021926 | GTTTCGTAGTTTCGTAGTTTCGTAG | TTCTTACCGACCCAAAACGTA |
| 5 | ALX4_75642 | 60529 | ALX4 | NM_021926 | GGTCGTTGTTATGGACGTTT | AAAATTATACCGAACTTATCGCCT |
| 6 | ALX4_75643 | 60529 | ALX4 | NM_021926 | TTCGTTATATTTTAGTTTAGCGTTT | ACACAAACCTTCGTCGTCC |

| Nr | Assay Name | Gene ID | Official Gene Symbol | Refseq | Amplicon Sequence (converted) (5' – 3') SEQ ID NO's 349-354 |
|---|---|---|---|---|---|
| 1 | ALX4_75634 | 60529 | ALX4 | NM_021926 | CGTTAGGTTTTGTTGTTTAGCGTCGTAACGGGTTCGGTTTTTGGCGTTTTCGAATTTTTGTGTTTTGGCGGCGGTCGATAGGAAAGTTGTGTCG |
| 2 | ALX4_75635 | 60529 | ALX4 | NM_021926 | CGTTAGGTTTTGTTGTTTAGCGTCGTAACGGGTTCGGTTTTTGGCGTTTTCGAATTTTTGTGTTTTGGCGGCGGTCGATAGGAAAGTT |
| 3 | ALX4_75636 | 60529 | ALX4 | NM_021926 | GTTTCGTAGTTTAGCGTTAGAGCGTTGCGCGGAGATTTTTTGTCGTCGTACGTTTTGGGTCGGTAAGAAGTATTCGTTTT |
| 4 | ALX4_75637 | 60529 | ALX4 | NM_021926 | GTTTCGTAGTTTCGTAGTTTCGTAGTTTAGCGTTAGAGCGTTGCGCGGAGATTTTTTGTCGTCGTACGTTTTGGGTCGGTAAGAA |
| 5 | ALX4_75642 | 60529 | ALX4 | NM_021926 | GGTCGTTGTTATGGACGTTTATTATAGTTCGGTGTCGTAGAGTCGGGAGGGTTCGTCGTTTTTTAGGGTATTTTTCGGAGGCGATAAGTTCGGTATAATTTT |
| 6 | ALX4_75643 | 60529 | ALX4 | NM_021926 | TTCGTTATATTTTAGTTTAGCGTTTTTATAGAGGGGAAATAGTTAATAAGACGTGTAAGTGATTATGTATTGGACGACGAAGGTTTGTGT |

Figure 5B (cont.)

| Nr | Assay Name | Gene ID | Official Gene Symbol | Refseq | Amplicon Sequence (not converted) (5' – 3') SEQ ID NO's 355-360 |
|---|---|---|---|---|---|
| 1 | ALX4_75634 | 60529 | ALX4 | NM_021926 | CGCCAGGTCCTGCTGCCCAGCGCCGTAACGGGCCCGGCTCTTGGCGTCCCCGAATCCCTGTGCTTTGGCGGCGGCCGACAGGAAAGTTGTGCCG |
| 2 | ALX4_75635 | 60529 | ALX4 | NM_021926 | CGCCAGGTCCTGCTGCCCAGCGCCGTAACGGGCCCGGCTCTTGGCGTCCCCGAATCCCTGTGCTTTGGCGGCGGCCGACAGGAAAGTT |
| 3 | ALX4_75636 | 60529 | ALX4 | NM_021926 | GCCCCGCAGCCCAGCGCCAGAGCGCTGCGCGGAGACTCCTTGCCGCCGCACGCCCTGGGCCGGTAAGAAGCATCCGCTTC |
| 4 | ALX4_75637 | 60529 | ALX4 | NM_021926 | GCCCCGCAGCCCCGCAGCCCCGCAGCCCCAGCGCCAGAGCGCTGCGCGGAGACTCCTTGCCGCCGCACGCCCTGGGCCGGTAAGAA |
| 5 | ALX4_75642 | 60529 | ALX4 | NM_021926 | GGCCGCTGCCATGGACGCCTACTACAGCCCGGTGTCGCAGAGTCGGGAGGGCTCGTCGCCTTTTAGGGCATTTCCCGGAGGCGACAAGTTCGGCACAACTTT |
| 6 | ALX4_75643 | 60529 | ALX4 | NM_021926 | TCCGCTACATCCCAGCCCAGCGCCCTTACACAGAGGGAAATAGTTAACAAGACGTGCAAGTGACCATGCACTGGACGACGAAGGCTTGTGT |

| Lightcycler ranking | Base5 ranking | Assays | 27 Cancers | 20 Normals | p-value |
|---|---|---|---|---|---|
| 1 | 8 | JAM3 | | | 7.84E-08 |
| 2 | 4 | EPB41L3_19071 | | | 1.52E-06 |
| 3 | 21 | NOL4_19645 | | | 2.47E-05 |
| 4 | 11 | SOX1_27153 | | | 8.38E-05 |
| 5 | 10 | SLIT2_23672 | | | 1.25E-04 |
| 6 | 121 | PAK3_3 | | | 1.36E-04 |
| 7 | 9 | JPH3_12611 | | | 1.42E-04 |
| 8 | 20 | TERT_23702 | | | 1.43E-04 |
| 9 | NT | CALCA_2 | | | 6.35E-04 |
| 10 | 22 | HOXA11_23844 | | | 7.75E-04 |
| 11 | 46 | DBC1_23879 | | | 1.03E-03 |
| 12 | 1 | LMX1A_9513 | | | 2.59E-03 |
| 13 | 30 | POMC | | | 5.44E-03 |
| 14 | 49 | ALX4_25062 | | | 5.83E-03 |
| 15 | 24 | C13orf18_19885 | | | 7.46E-03 |
| 16 | 36 | TFPI-2 | | | 7.46E-03 |
| 17 | 5 | WT1_1 | | | 7.76E-03 |
| 18 | 28 | SLIT1_23651 | | | 9.91E-03 |
| 19 | 17 | SLIT2_23676 | | | 1.15E-02 |
| 20 | 39 | EGR4_24277 | | | 1.28E-02 |
| 21 | 27 | GATA4_13295 | | | 1.44E-02 |
| 22 | 15 | CDH4_24735 | | | 2.02E-02 |
| 23 | 19 | DKK2_23970 | | | 3.64E-02 |
| 24 | 47 | GDAP1L1_19775 | | | 5.99E-02 |
| 25 | 7 | ALX3_25180 | | | 6.25E-02 |
| 26 | 6 | DKK2_23973 | | | 7.07E-02 |
| 27 | 321 | RECK_18940 | | | 1.03E-01 |
| 28 | 37 | TWIST1_9329 | | | 1.07E-01 |
| 29 | 45 | C16orf48_22922 | | | 1.65E-01 |
| 30 | 12 | SOX1_27159 | | | 1.76E-01 |
| 31 | 58 | CYCLIND2_1 | | | 1.76E-01 |
| 32 | 38 | SST_23808 | | | 2.00E-01 |
| 33 | 136 | NPTX1_2 | | | 2.54E-01 |
| 34 | 34 | DAPK1 | | | 2.67E-01 |
| 35 | 65 | COL1A1_23253 | | | 2.72E-01 |
| 36 | 125 | HOXA7_2 | | | 2.92E-01 |
| 37 | 25 | PAX1_27210 | | | 3.33E-01 |
| 38 | 76 | CDH1_17968 | | | 3.37E-01 |
| 39 | 29 | LOC285016_22940 | | | 4.29E-01 |
| 40 | 48 | OGFOD2_23131 | | | 4.29E-01 |
| 41 | 94 | BMP2_17901 | | | 5.73E-01 |
| 42 | 91 | FOXE1_13314 | | | 6.09E-01 |
| 43 | 14 | RPRM_2 | | | 6.70E-01 |
| 44 | 35 | GDAP1L1_19773 | | | 6.75E-01 |
| 45 | 341 | UGT1A1_22912 | | | 6.75E-01 |
| 46 | 2 | SLIT2_23681 | | | 1.00E+00 |
| 46 | 26 | WIT1_24567 | | | 1.00E+00 |
| 46 | 18 | PAX1_27211 | | | 1.00E+00 |
| 46 | 13 | RALY_19607 | | | 1.00E+00 |
| 46 | 127 | CTDSPL_23804 | | | 1.00E+00 |
| 46 | 78 | SOCS1_23595 | | | 1.00E+00 |
| 46 | 71 | CDK6_9703 | | | 1.00E+00 |
| 46 | 51 | TLL1_24051 | | | 1.00E+00 |
| 46 | 3 | ISYNA1_19726 | | | 1.00E+00 |
| 46 | 16 | CPT1C_23912 | | | 1.00E+00 |
| 46 | 174 | SMPD1_24061 | | | 1.00E+00 |
| 46 | 120 | SEMA3F_23485 | | | 1.00E+00 |
| 46 | 110 | AURKA_24802 | | | 1.00E+00 |
| 46 | 164 | SLIT1_23653 | | | 1.00E+00 |
| 46 | 32 | Gst-Pi_New3 | | | 1.00E+00 |
| 46 | 281 | KRAS_24235 | | | 1.00E+00 |
| 46 | 250 | GADD45A_24463 | | | 1.00E+00 |
| 46 | 52 | CTDSPL_23795 | | | 1.00E+00 |
| NA | NA | Beta_Actin | | | NA |

US 9,371,569 B2

DETECTION AND PROGNOSIS OF CERVICAL CANCER

FIELD OF THE INVENTION

The present invention relates to the area of cancer diagnostics and therapeutics. In particular, it relates to methods and kits for identifying, diagnosing, prognosing, and monitoring cervical cancer. These methods include determining the methylation status or the expression levels of particular genes, or a combination thereof.

BACKGROUND TO THE INVENTION

Cervical cancer is the fifth most deadly cancer in women. Worldwide, approximately 500,000 cases of cervical cancer are diagnosed and about 250,000 women die from this disease annually (www.who.int/mediacentre/factsheets).

Most (80-90%) invasive cervical cancer develops in flat, scaly surface cells that line the cervix (called squamous cell carcinomas, SCC). Approximately 10-15% of cases develop in glandular surface cells (called adenocarcinomas, AdC). Less commonly, cervical cancers have features of both SCC and AdC. These are called adenosquamous carcinomas or mixed carcinomas (www.cancer.org).

During the process of cervical cancer development, normal cervical cells gradually develop pre-cancerous changes that turn into cancer. Cervical cancer evolves from pre-existing noninvasive premalignant lesions referred to as cervical intraepithelial neoplasias (CINs), ranging from CIN I (mild dysplasia) to CIN II (moderate dysplasia) to CIN III (severe dysplasia/carcinoma in situ). This process usually takes several years but sometimes can happen in less than a year. For most women, pre-cancerous cells will remain unchanged and disappear without any treatment.

Screening for malignant and premalignant disorders of the cervix is usually performed according to the Papanicolaou (PAP) system. The cervical smears are examined by light microscopy and the specimens containing morphologically abnormal cells are classified into PAP I to V, at a scale of increasing severity of the lesion. But, present PAP test has some limitations and is not completely ideal for screening as it suffers from suboptimal single-test sensitivity, limited reproducibility, and many equivocal.

There is a strong association between certain subtypes of the Human Papillomavirus (HPV) and cervical cancer. Studies have shown that only high-risk HPV types are involved in the progression from cytological normal cervix cells to high grade squamous intraepithelial lesions. Around 15 high-risk (cancer-causing) HPV types have been identified. Although it has been suggested that high-risk HPV testing may improve cervical cancer screening, the specificity for high grade cervical neoplasia of high risk HPV testing is relatively low. This low specificity of HPV testing leads to a higher number of unnecessarily follow-up diagnostic workups (e.g. colposcopy) and unnecessarily treatment with cryotherapy or loop electrosurgical excision procedure, which permanently alters the cervix and have unknown consequences on fertility and pregnancy.

To improve early detection, the combination of HPV and PAP tests is now approved by the FDA for screening women 30 years of age and older. However, co-testing substantially increases the cost of screening.

In the meanwhile, vaccines for preventing cervical cancer have been developed and one has already been approved by the FDA. But, immunization will only protect against HPV types that are targeted by the vaccine; protection will not be absolute and its longevity is uncertain; as yet, the possibility of genotype replacement cannot be excluded; and older women not covered by vaccination programs will continue to be at risk. Therefore, cervical screening will still be required for control.

Cancer biomarkers have been described in literature and aberrant methylation of genes has been linked to cervical cancer (Virmani et al, 2001). In addition, methylation markers may serve for predictive purposes as they often reflect the sensitivity to therapy or duration of patient survival.

DNA methylation is a chemical modification of DNA performed by enzymes called methyltransferases, in which a methyl group (m) is added to certain cytosines (C) of DNA. This non-mutational (epigenetic) process (mC) is a critical factor in gene expression regulation. (See J. G. Herman, Seminars in Cancer Biology, 9: 359-67, 1999).

An early diagnosis is critical for the successful treatment of many types of cancer, including cervical cancer. If the exact methylation profiles of cervical tumors are available and drugs targeting the specific genes are obtainable, then the treatment of cervical cancer could be more focused and rational. Therefore, the detection and mapping of novel methylation markers is an essential step towards improvement of cervical cancer prevention, screening, and treatment. Thus, there is a continuing need in the art to identify methylation markers that can be used for improved assessment of cervical cancer.

SUMMARY OF THE INVENTION

The present invention is based on the finding that several genes are identified as being differentially methylated in cervical cancers. This information is useful for cervical cancer screening, risk-assessment, prognosis, disease identification, disease staging, and identification of therapeutic targets. The identification of new genes that are methylated in cervical cancer allows accurate and effective early diagnostic assays, methylation profiling using multiple genes and identification of new targets for therapeutic intervention.

Accordingly, in a first aspect, the invention provides a method for identifying cervical cancer or its precursor, or predisposition to cervical cancer. Epigenetic modification of at least one gene selected from the group consisting of genes according to Table 1, is detected in a test sample containing cervical cells or nucleic acids from cervical cells. The test sample is identified as containing cells that are neoplastic, precursor to neoplastic, or predisposed to neoplasia, or as containing nucleic acids from cells that are neoplastic, precursor to neoplastic, or predisposed to neoplasia.

Preferably, the at least one gene is selected from a group of genes consisting of JAM3, LMX1A, CDO1, NID2, ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, GPNMB, GREM1, Gst-Pi, HHIP, HIN1, HOOK2, HOXA1, HOXA11, HOXA7, HOXD1, IGSF4, ISYNA1, JPH3, KNDC1, KRAS, LAMA1, LOC285016, LOX, LTB4R, MAL, MTAP, MYO18B, NDRG2, NOL4, NPTX1, NPTX2, OGFOD2, PAK3, PAX1, PDCD4, PHACTR3, POMC, PRKCE, RAD23B, RALY, RARA, RASSF1A, RBP4, RECK, RPRM, SALL4, SEMA3F, SLC5A8, SLIT1, SLIT2, SLIT3, SMPD1, SOCS1, SOX1, SOX17, SPARC, SPN, SST, TAC1, TERT, TFPI-2, TLL1, TNFAIP1, TRMT1, TWIST1, UGT1A1, WIF1, WIT1, WT1, XRCC3, and ZGPAT.

In one embodiment of the present invention, the detection of epigenetic modification comprises detection of methylation of a CpG dinucleotide motif in the gene and/or promoter region of the gene; and/or detection of expression of mRNA of the gene.

The invention also relates to a kit for assessing cervical cancer or its precursor, or predisposition to cervical cancer in a test sample containing cervical cells or nucleic acids from cervical cells. The kit comprises in a package: a reagent that (a) modifies methylated cytosine residues but not non-methylated cytosine residues, or that (b) modifies non-methylated cytosine residues but not methylated cytosine residues; and at least one pair of oligonucleotide primers that specifically hybridizes under amplification conditions to a region of a gene selected from the group consisting of genes according to Table 1 and/or the aforementioned group of genes. The region is preferably within about 10 kbp of said gene's transcription start site.

In a further aspect, the invention provides for oligonucleotide primers and/or probes and their sequences for use in the methods and assays of the invention.

The invention also relates to screening protocols for the screening of woman for cervical cancer and the precursors thereof. Such method for cervical cancer screening combines hr-HPV testing and methylation testing, or combines PAP tests with methylation testing. Methylation testing in such screening method preferably detects the epigenetic modification of at least one gene selected from the group consisting of JAM3, LMX1A, CDO1, NID2, ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, GPNMB, GREM1, Gst-Pi, HHIP, HIN1, HOOK2, HOXA1, HOXA11, HOXA7, HOXD1, IGSF4, ISYNA1, JPH3, KNDC1, KRAS, LAMA1, LOC285016, LOX, LTB4R, MAL, MTAP, MYO18B, NDRG2, NOL4, NPTX1, NPTX2, OGFOD2, PAK3, PAX1, PDCD4, PHACTR3, POMC, PRKCE, RAD23B, RALY, RARA, RASSF1A, RBP4, RECK, RPRM, SALL4, SEMA3F, SLC5A8, SLIT1, SLIT2, SLIT3, SMPD1, SOCS1, SOX1, SOX17, SPARC, SPN, SST, TAC1, TERT, TFPI-2, TLL1, TNFAIP1, TRMT1, TWIST1, UGT1A1, WIF1, WIT1, WT1, XRCC3, and ZGPAT. Dependent on the outcome, the women screened for cervical cancer is referred for colposcopy, or referred for hr-HPV and/or PAP testing and/or methylation testing on a more regular basis.

Epigenetic loss of gene function can be rescued by the use of DNA demethylating agents and/or DNA methyltransferase inhibitors. Accordingly, the invention also provides for a method for predicting the likelihood of successful treatment or resistance to treatment of cancer with such agent. If the gene is methylated, the likelihood of successful treatment is higher than if the gene is unmethylated, or methylated to a lesser degree. Conversely, if the gene is unmethylated, or methylated to a lesser degree, the likelihood of resistance to treatment is higher than if the gene is methylated.

In a related aspect, epigenetic loss of gene function(s) can identify the stage of the disease and from that the need of treatment. Accordingly, the invention provides for a method for predicting suitable treatment comprising determining the methylation status of a gene or a combination of genes. If the gene is methylated, the need of cervical resection is identified; if the gene is unmethylated or methylated to a lesser degree, it is decided that there is no need for cervical resection.

A: schematic representation of the restriction enzyme sites (B: BstUI and T: TaqI) in the virtual hypermethylated BSP nucleotide sequence after bisulfate treatment. Vertical bars represent CG site, arrow represents TSS (retrieved from Ensembl).

B: Result of COBRA analysis of the BSP products of 10 tumor samples (T1-T10), in vitro methylated DNA as a positive control (IV) and leukocyte DNA as a negative (unmethylated) control (L).

C: Schematic representation of the sequencing results. From each tumor, the BSP-products were cloned into TOPO-pCR4 (Invitrogen) and sequencing (BaseClear) was performed on M13-PCR products of 7-9 independent clones. Circles represent CG dinucleotides: the darker, the more clones at this site were methylated.

Figure 4:
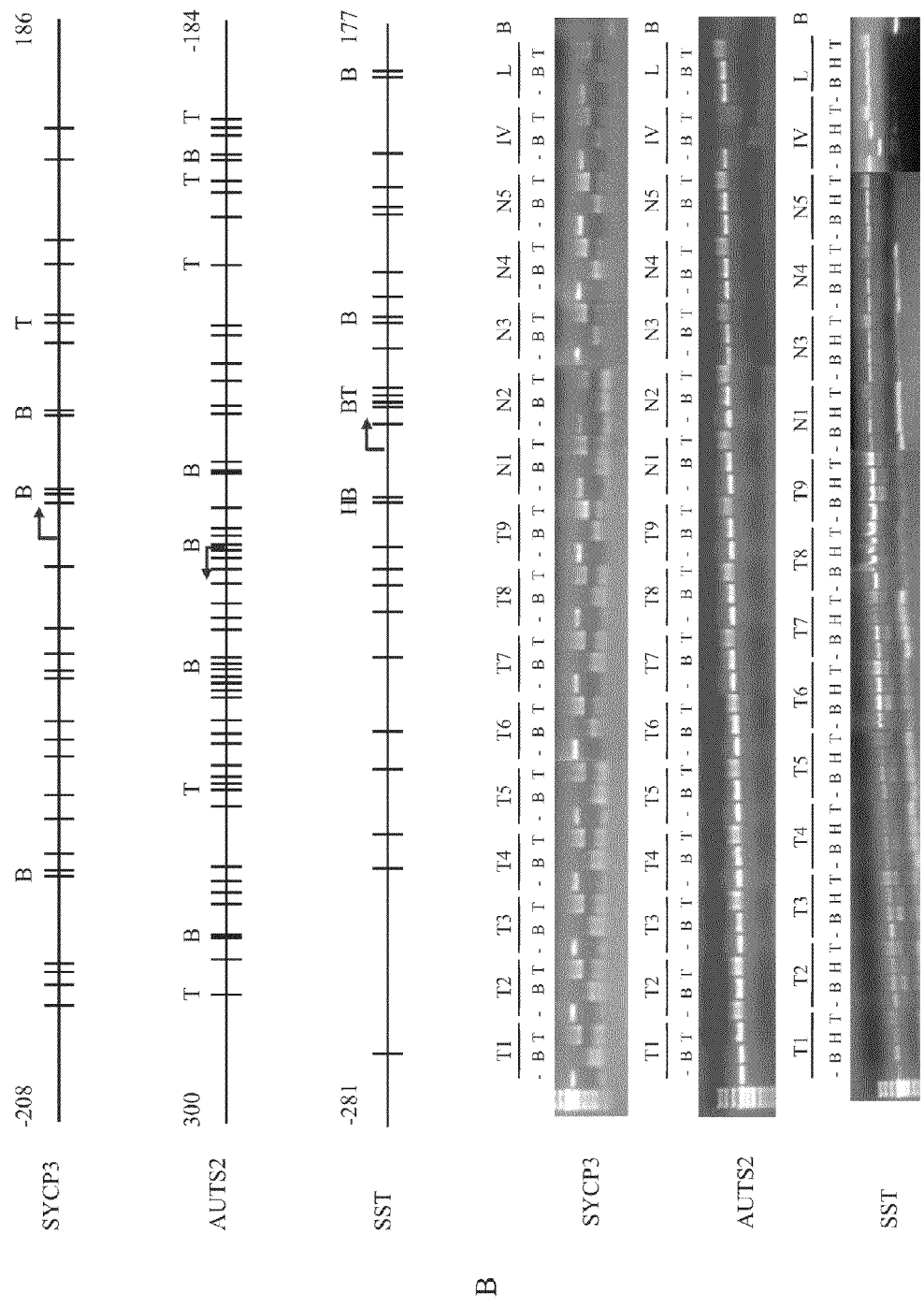

FIG. 4: Representative COBRA on 3 gene promoters (SST, AUTS2 and SYCP3).

A: schematic representation of the restriction enzyme sites in the virtual hypermethylated BSP nucleotide sequence after bisulfate treatment. (B: BstUI, T: TaqI and H: HinfI). Bars represent CG site and arrow is TSS (retrieved from Ensembl).

B: Result of COBRA analysis of BSP products of tumor samples (T1-T10) and 5 normal cervices (N1-N5), in vitro methylated DNA as a positive control (IV) and leukocyte DNA as a negative (unmethylated) control (L); lane B is water blank.

FIG. 5:

A: Position of the different primers relative to the TSS (transcription start site). Multiple primer designs are displayed by blue boxes and red boxes (=final primer pairs retained for the assays). The exon of ALX4 is indicated in green. The number of CpG count is spotted in blue over a region of 20 Kb.

Figure 5A:
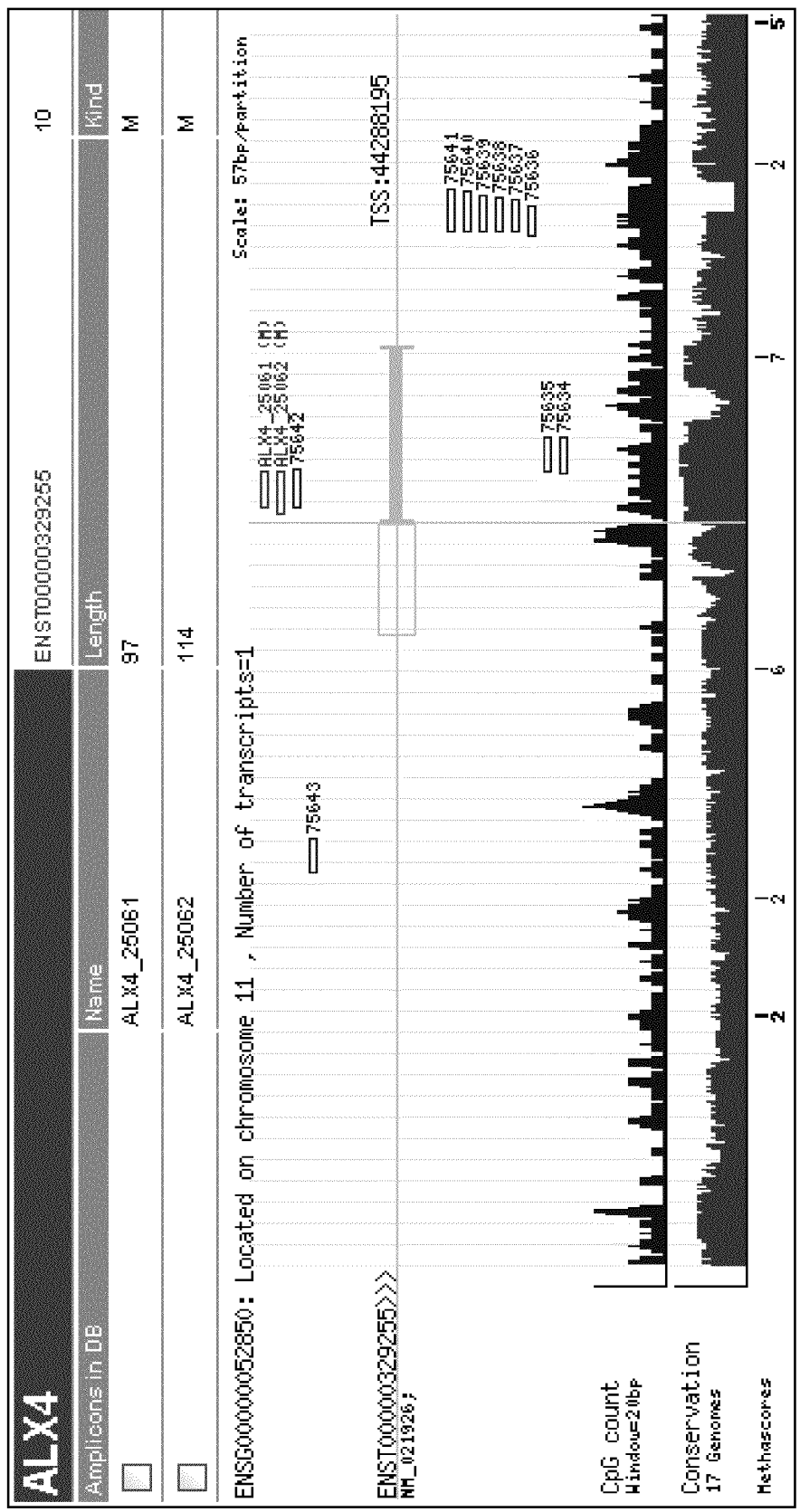

B: List of sequences for the different primer sets, converted and unconverted amplicon sequences used in FIG. 5 A.

Figure 6A:
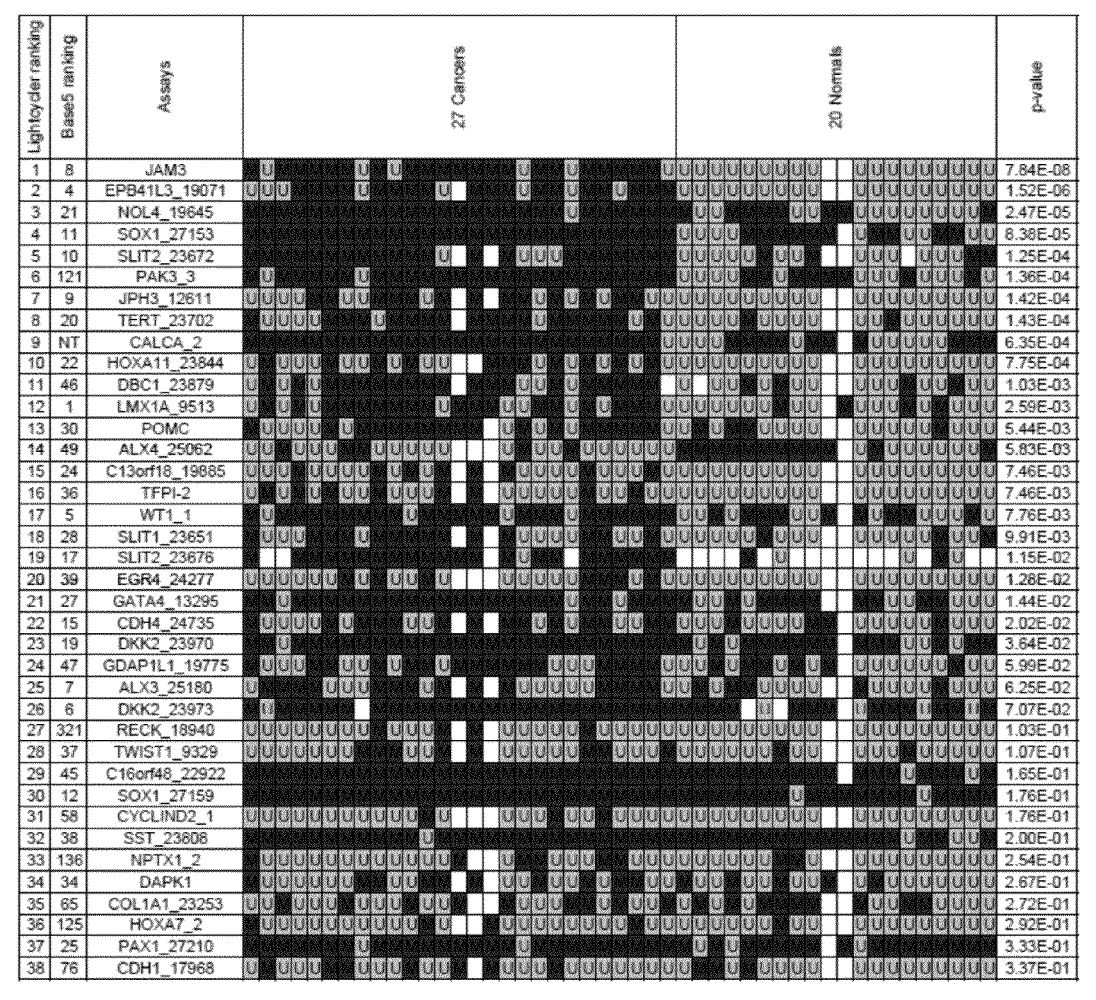

FIGS. 6A and B: Ranked methylation table from the Lightcycler platform. 27 methylation profiles from cervical cancer samples (left) are compared against 20 normal tissue samples (right). Samples are shown along the X-axis where each vertical column represents the methylation profile of one individual sample across the 63 different assays (Y-axis). Assays demonstrating the best methylation discriminators between the 2 groups are displayed at the top, with discrimination effect decreasing towards the bottom. The black boxes indi- FIG. 7: Amplification plot for the standard curve for TAC1_56187

Figure 8:
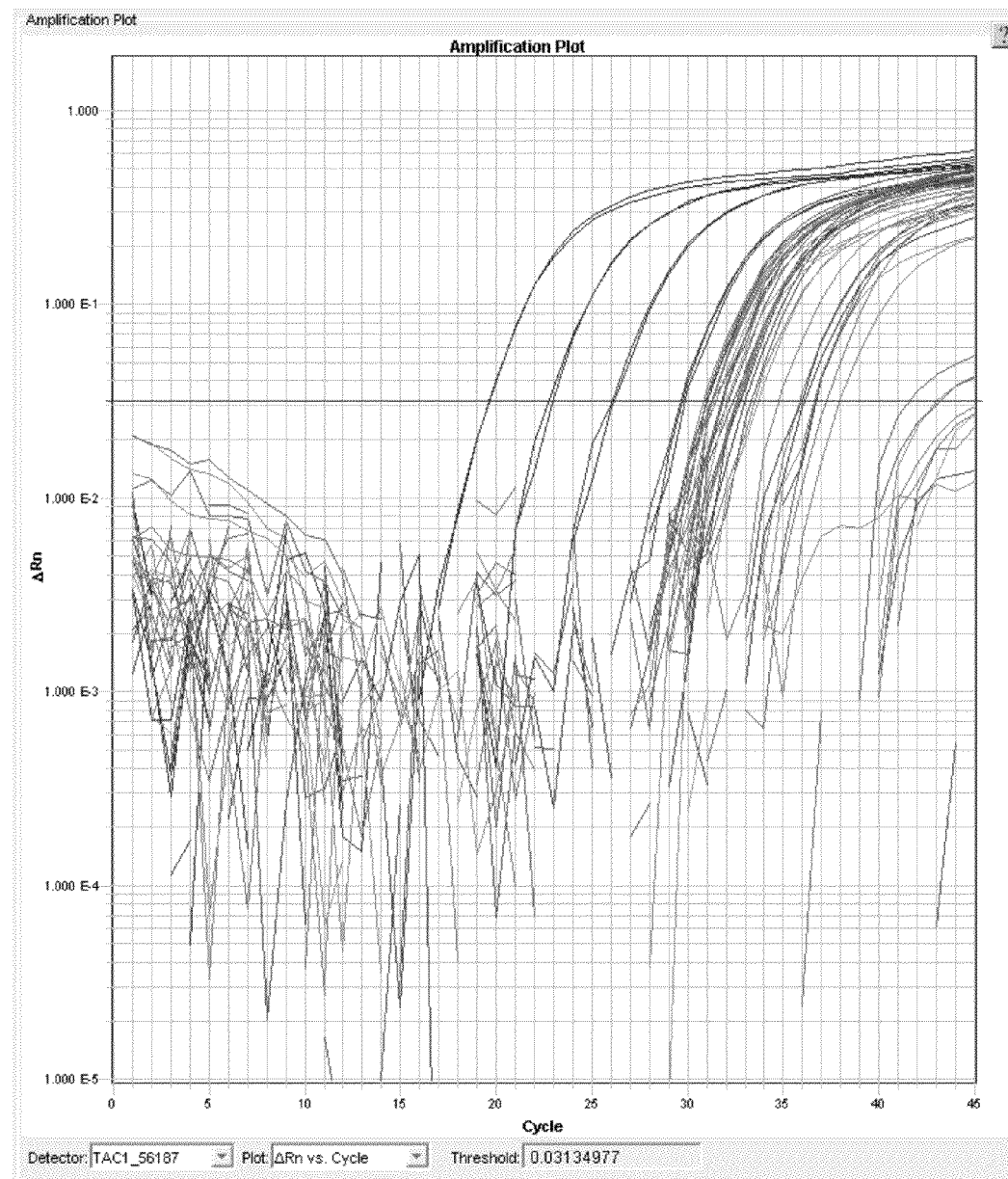

FIG. 8: Amplification plot for standard curve and samples for TAC1_56187

Figure 9:
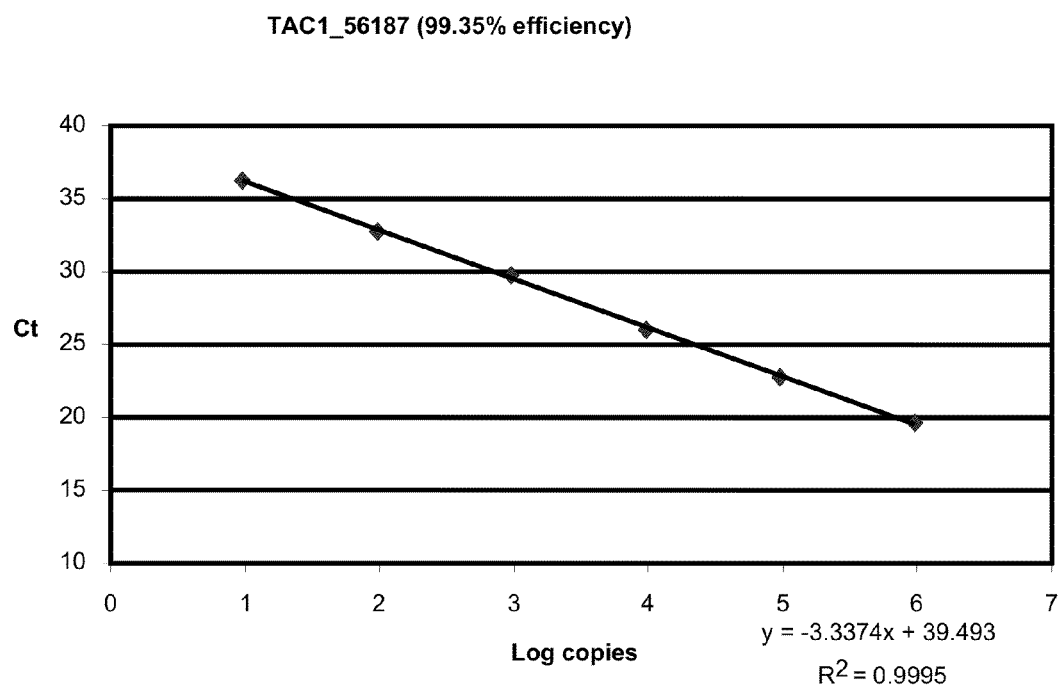

FIG. 9: Linear regression of standard curve for TAC1_56187

Figure 10:
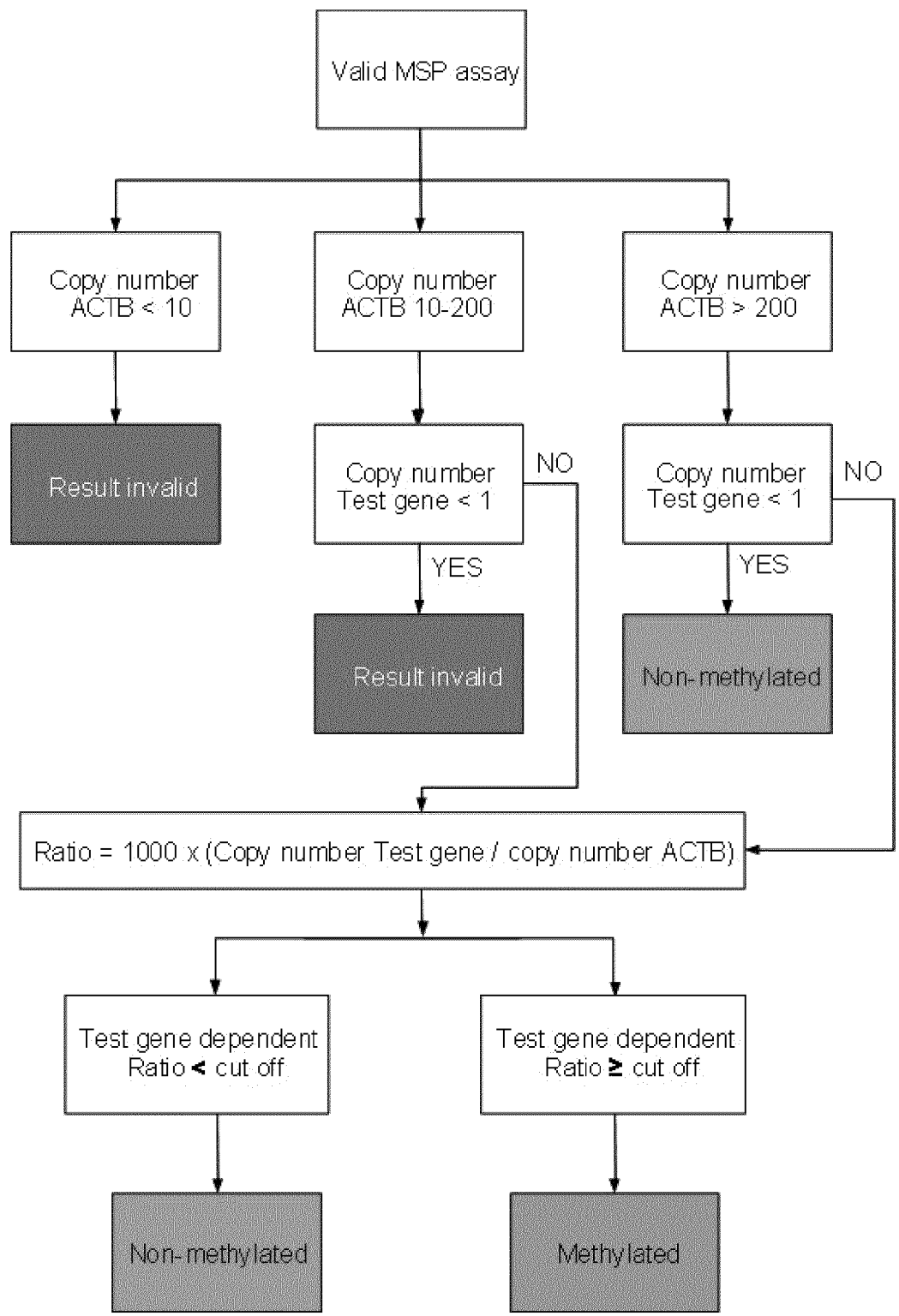

FIG. 10: Decision tree for ratio determination

Figure 11:
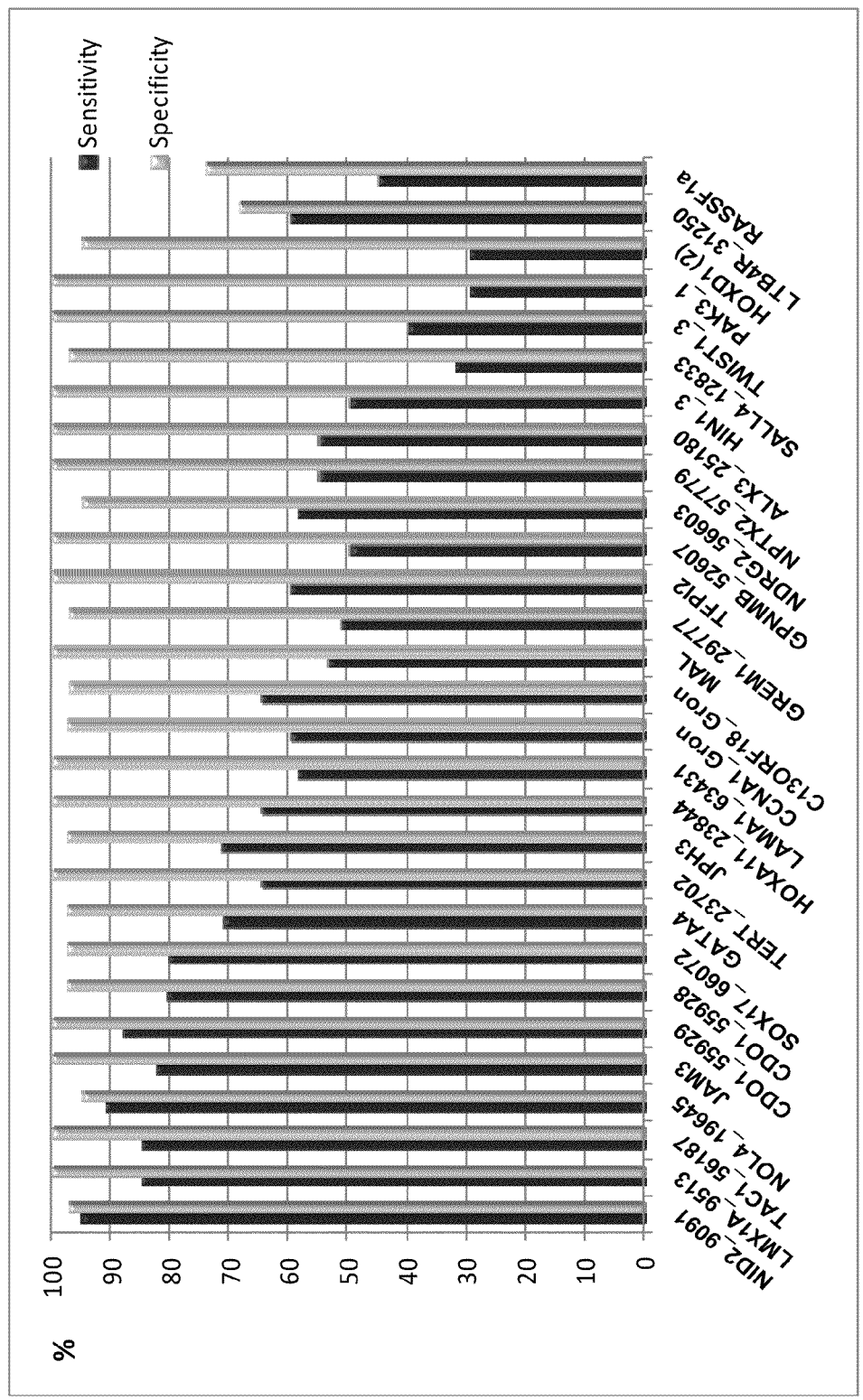

FIG. 11: Performance of the individual markers on cervical tissue samples using qMSP.

DETAILED DESCRIPTION OF THE INVENTION

We describe a new sorting methodology to enrich for genes which are silenced by promoter methylation in human cervical cancer. The pharmacological unmasking expression microarray approach is an elegant method to enrich for genes that are silenced and re-expressed during functional reversal of DNA methylation upon treatment with demethylating agents. However, such experiments are performed in in vitro (cancer) cell lines mostly with poor relevance when extrapolating to primary cancers. To overcome this problem, we incorporated data from primary cancer samples in the experimental design. A pharmacological unmasking microarray approach was combined with microarray expression data of primary cancer samples. For the integration of data from both cell lines and primary cancers, we developed a novel ranking strategy, which combines reactivation in cell lines and no expression in primary cancer tissue.

We also used a Genome-wide Promoter Alignment approach with the capacity to define a further substantial fraction of the cancer gene promoter CpG island DNA methylome. Markers clustering with known methylation markers might indicate towards common mechanisms underlying the methylation event and thus identify novel genes that are more methylation-prone.

Studies of the genes defined by the different approaches will contribute to understanding the molecular pathways driving tumorigenesis, provide useful new DNA methylation biomarkers to monitor cancer risk assessment, early diagnosis, and prognosis, and permit better monitoring of gene re-expression during cancer prevention and/or therapy strategies.

Using the aforementioned techniques, we have identified cytosines within CpG dinucleotides of DNA from particular genes isolated from a test sample, which are differentially methylated in human cervical cancer tissue samples and normal cervical tissue control samples. The cancer tissues samples are hypermethylated or hypomethylated with respect to the normal samples (collectively termed epigenetic modification). The differential methylation has been found in genomic DNA of at least one gene selected from the group consisting of JAM3, LMX1A, CDO1, NID2, ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, GPNMB, GREM1, Gst-Pi, HHIP, HIN1, HOOK2, HOXA1, HOXA11, HOXA7, HOXD1, IGSF4, ISYNA1, JPH3, KNDC1, KRAS, LAMA1, LOC285016, LOX, LTB4R, MAL, MTAP, MYO18B, NDRG2, NOL4, NPTX1, NPTX2, OGFOD2, PAK3, PAX1, PDCD4, PHACTR3, POMC, PRKCE, RAD23B, RALY, RARA, RASSF1A, RBP4, RECK, RPRM, SALL4, SEMA3F, SLC5A8, SLIT1, SLIT2, SLIT3, SMPD1, SOCS1, SOX1, SOX17, SPARC, SPN, SST, TAC1, TERT, TFPI-2, TLL1, TNFAIP1, TRMT1, TWIST1, UGT1A1, WIF1, WIT1, WT1, XRCC3, and ZGPAT.

Accordingly, in a first aspect, the invention provides a method for identifying cervical cancer or its precursor, or predisposition to cervical cancer. Epigenetic modification of at least one gene selected from the group consisting of genes according to Table 1, is detected in a test sample containing cervical cells or nucleic acids from cervical cells. The test sample is identified as containing cells that are neoplastic, precursor to neoplastic, or predisposed to neoplasia, or as containing nucleic acids from cells that are neoplastic, precursor to neoplastic, or predisposed to neoplasia.

Preferably, the at least one gene is selected from a group of genes consisting of JAM3, LMX1A, CDO1, NID2, ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, GPNMB, GREM1, Gst-Pi, HHIP, HIN1, HOOK2, HOXA1, HOXA11, HOXA7, HOXD1, IGSF4, ISYNA1, JPH3, KNDC1, KRAS, LAMA1, LOC285016, LOX, LTB4R, MAL, MTAP, MYO18B, NDRG2, NOL4, NPTX1, NPTX2, OGFOD2, PAK3, PAX1, PDCD4, PHACTR3, POMC, PRKCE, RAD23B, RALY, RARA, RASSF1A, RBP4, RECK, RPRM, SALL4, SEMA3F, SLC5A8, SLIT1, SLIT2, SLIT3, SMPD1, SOCS1, SOX1, SOX17, SPARC, SPN, SST, TAC1, TERT, TFPI-2, TLL1, TNFAIP1, TRMT1, TWIST1, UGT1A1, WIF1, WIT1, WT1, XRCC3, and ZGPAT.

Preferably, at least one gene is selected from the group consisting of JAM3, LMX1A, CDO1, NID2, CCNA1, HOXA11, GREM1 and TAC1. Preferably, epigenetic silencing of a gene combination is detected and preferably selected from the group of gene combinations consisting of:

NID2 and HOXA11;
JAM3, CDO1, HOXA11, and CCNA1;
JAM3 and HOXA11;
JAM3, HOXA11 and GREM1;
JAM3, NID2, HOXA11 and CDO1;
JAM3, TAC1, HOXA11, and CDO1;
JAM3, HOXA11, and CDO1;
JAM3 and CDO1;
JAM3 and NID2;
NID2 and CDO1;
JAM3 and LMX1A
NID2 and LMX1A, and
JAM3, CDO1 and NID2

"Identifying" a disease or predisposition of disease is defined herein to include detecting by way of routine examination, screening for a disease or pre-stadia of a disease, monitoring staging and the state and/or progression of the disease, checking for recurrence of disease following treatment and monitoring the success of a particular treatment. The identification can also have prognostic value, and the prognostic value of the tests can be used as a marker of potential susceptibility to cancer.

The term "Epigenetic modification" can be described as a stable alteration in gene expression potential that takes place during development and cell proliferation, mediated by mechanisms other than alterations in the primary nucleotide sequence of a gene. Three related mechanisms that cause alteration in gene expression are recognized: DNA methylation, histone code changes and RNA interference.

Epigenetic modification of a gene can be determined by any method known in the art. One method is to determine that a gene which is expressed in normal cells or other control cells is less expressed or not expressed in tumor cells. Diminished gene expression can be assessed in terms of DNA methylation status or in terms of expression levels as determined by their methylation status, generally manifested as hypermethylation. Conversely, a gene can be more highly expressed in tumor cells than in control cells in the case of hypomethylation. This method does not, on its own, however, indicate that the silencing or activation is epigenetic, as the mechanism of the silencing or activation could be genetic, for example, by somatic mutation. One method to determine that silencing is epigenetic is to treat with a reagent, such as DAC (5'-deazacytidine), or with a reagent which changes the histone acetylation status of cellular DNA or any other treatment affecting epigenetic mechanisms present in cells, and observe that the silencing is reversed, i.e., that the expression of the gene is reactivated or restored.

Another means to determine epigenetic modification is to determine the presence of methylated CpG dinucleotide motifs in the silenced gene or the absence of methylation CpG dinucleotide motifs in the activated gene. In one embodiment, epigenetic modification of a CpG dinucleotide motif in the promoter region of the at least one gene selected from a group of genes according to Table 1 is determined. Methylation of a CpG island at a promoter usually prevents expression of the gene. The islands can surround the 5' region of the coding region of the gene as well as the 3' region of the coding region. Thus, CpG islands can be found in multiple regions of a nucleic acid sequence. The term "region" when used in reference to a gene includes sequences upstream of coding sequences in a regulatory region including a promoter region, in the coding regions (e.g., exons), downstream of coding regions in, for example, enhancer regions, and in introns. All of these regions can be assessed to determine their methylation status. When the CpG distribution in the promoter region is rather scarce, levels of methylation are assessed in the intron and/or exon regions. The region of assessment can be a region that comprises both intron and exon sequences and thus overlaps both regions. Typically these reside near the transcription start site (TSS), for example, within about 10 kbp, within about 5 kbp, within about 3 kbp, within about 1 kbp, within about 750 bp, within about 500 bp, within 200 bp or within 100 bp. Once a gene has been identified as the target of epigenetic modification in tumor cells, determination of reduced or enhanced expression can be used as an indicator of epigenetic modification.

Expression of a gene can be assessed using any means known in the art. Typically expression is assessed and compared in test samples and control samples which may be normal, non-malignant cells. Either mRNA or protein can be measured. Methods employing hybridization to nucleic acid probes can be employed for measuring specific mRNAs. Such methods include using nucleic acid probe arrays (e.g. microarray technology, in situ hybridization, Northern blots). Messenger RNA can also be assessed using amplification techniques, such as RT-PCR. Sequencing-based methods are an alternative; these methods started with the use of expressed sequence tags (ESTs), and now include methods based on short tags, such as serial analysis of gene expression (SAGE) and massively parallel signature sequencing (MPSS). Differential display techniques provide another means of analyzing gene expression; this family of techniques is based on random amplification of cDNA fragments generated by restriction digestion, and bands that differ between two tissues identify cDNAs of interest. Specific proteins can be assessed using any convenient method including immunoassays and immuno-cytochemistry but are not limited to that. Most such methods will employ antibodies, or engineered equivalents thereof, which are specific for the particular protein or protein fragments. The sequences of the mRNA (cDNA) and proteins of the markers of the present invention are known in the art and publicly available.

Alternatively, methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Non limiting examples of the former are Aat II, Acc III, Ad I, AcI I, Age I, Alu I, Asc I, Ase 1, AsiS I, Ban I, Bbe I, BsaA I, BsaH I, BsiE I, BsiW I, BsrV I, BssK 1, BstB I, BstN I, Bs I, Cla I, Eae I, Eag I, Fau I, Fse I, Hha I, mPl I, HinC II, Hpa 11, Npy99 I, HpyCAIV, Kas I, Mbo I, Mlu I, MapA 11. Msp I, Nae I, Nar I, Not 1, Pml I, Pst I, Pvu I, Rsr II, Sac II, Sap I, Sau3A I, Sfl I, Sfo I, SgrA I, Sma I SnaB I, Tsc I, Xma I, and Zra I. Non limiting examples of the latter are Acc II, Ava I, BssH II, BstU I, Hpa II, Not I, and Mho I.

Alternatively, chemical reagents can be used that selectively modify either the methylated or non-methylated form of CpG dinucleotide motifs. Modified products can be detected directly, or after a further reaction which creates products that are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali. Other means for detection that are reliant on specific sequences can be used, including but not limited to hybridization, amplification, sequencing, and ligase chain reaction. Combinations of such techniques can be used as is desired.

The principle behind electrophoresis is the separation of nucleic acids via their size and charge. Many assays exist for detecting methylation and most rely on determining the presence or absence of a specific nucleic acid product. Gel electrophoresis is commonly used in a laboratory for this purpose.

One may use MALDI mass spectrometry in combination with a methylation detection assay to observe the size of a nucleic acid product. The principle behind mass spectrometry is the ionizing of nucleic acids and separating them according to their mass to charge ratio. Similar to electrophoresis, one can use mass spectrometry to detect a specific nucleic acid that was created in an experiment to determine methylation (Tost, J. et al. 2003).

One form of chromatography, high performance liquid chromatography, is used to separate components of a mixture based on a variety of chemical interactions between a substance being analyzed and a chromatography column. DNA is first treated with sodium bisulfite, which converts an unmethylated cytosine to uracil, while methylated cytosine residues remain unaffected. One may amplify the region containing potential methylation sites via PCR and separate the products via denaturing high performance liquid chromatography (DHPLC). DHPLC has the resolution capabilities to distinguish between methylated (containing cytosine) and unmethylated (containing uracil) DNA sequences. Deng, D. et al. describes simultaneous detection of CpG methylation and single nucleotide polymorphism by denaturing high performance liquid chromatography.

Hybridization is a technique for detecting specific nucleic acid sequences that is based on the annealing of two complementary nucleic acid strands to form a double-stranded molecule. One example of the use of hybridization is a microarray assay to determine the methylation status of DNA. After sodium bisulfite treatment of DNA, which converts an unmethylated cytosine to uracil while methylated cytosine residues remain unaffected, oligonucleotides complementary to potential methylation sites can hybridize to the bisulfite-treated DNA. The oligonucleotides are designed to be complimentary to either sequence containing uracil (thymine) or sequence containing cytosine, representing unmethylated and methylated DNA, respectively. Computer-based microarray technology can determine which oligonucleotides hybridize with the DNA sequence and one can deduce the methylation status of the DNA. Similarly primers can be designed to be complimentary to either sequence containing uracil (thymine) or sequence containing cytosine. Primers and probes that recognize the converted methylated form of DNA are dubbed methylation-specific primers or probes (MSP).

An additional method of determining the results after sodium bisulfite treatment involves sequencing the DNA to directly observe any bisulfite-modifications. Pyrosequencing technology is a method of sequencing-by-synthesis in real time. It is based on an indirect bioluminometric assay of the pyrophosphate (PPi) that is released from each deoxynucleotide (dNTP) upon DNA-chain elongation. This method presents a DNA template-primer complex with a dNTP in the presence of an exonuclease-deficient Klenow DNA polymerase. The four nucleotides are sequentially added to the reaction mix in a predetermined order. If the nucleotide is complementary to the template base and thus incorporated, PPi is released. The PPi and other reagents are used as a substrate in a luciferase reaction producing visible light that is detected by either a luminometer or a charge-coupled device. The light produced is proportional to the number of nucleotides added to the DNA primer and results in a peak indicating the number and type of nucleotide present in the form of a program. Pyrosequencing can exploit the sequence differences that arise following sodium bisulfite-conversion of DNA.

A variety of amplification techniques may be used in a reaction for creating distinguishable products. Some of these techniques employ PCR. Other suitable amplification methods include the ligase chain reaction (LCR) (Barringer et al, 1990), transcription amplification (Kwoh et al. 1989; WO88/10315), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO90/06995), nucleic acid based sequence amplification (NASBA) (U.S. Pat. Nos. 5,409,818; 5,554,517; 6,063,603), microsatellite length polymorphism (MLP), and nick displacement amplification (WO2004/067726).

Sequence variation that reflects the methylation status at CpG dinucleotides in the original genomic DNA offers two approaches to PCR primer design. In the first approach, the primers do not themselves cover or hybridize to any potential sites of DNA methylation; sequence variation at sites of differential methylation are located between the two primers. Such primers are used in bisulfite genomic sequencing, COBRA, Ms-SNuPE. In the second approach, the primers are designed to anneal specifically with either the methylated or unmethylated version of the converted sequence. If there is a sufficient region of complementarity, e.g., 12, 15, 18, or 20 nucleotides, to the target, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues.

One way to distinguish between modified and unmodified DNA is to hybridize oligonucleotide primers which specifically bind to one form or the other of the DNA. After primer hybridization, an amplification reaction can be performed. The presence of an amplification product indicates that a sample hybridized to the primer. The specificity of the primer indicates whether the DNA had been modified or not, which in turn indicates whether the DNA had been methylated or not. For example, bisulfite ions convert non-methylated cytosine bases to uracil bases. Uracil bases hybridize to adenine bases under hybridization conditions. Thus an oligonucleotide primer which comprises adenine bases in place of guanine bases would hybridize to the bisulfite-modified DNA, whereas an oligonucleotide primer containing the guanine bases would hybridize to the non-converted (initial methylated) cytosine residues in the modified DNA. Amplification using a DNA polymerase and a second primer yield amplification products which can be readily observed. This method is known as MSP (Methylation Specific PCR; U.S. Pat. Nos. 5,786,146; 6,017,704; 6,200,756). Primers are designed to anneal specifically with the converted sequence representing either the methylated or the unmethylated version of the DNA. Preferred primers and primer sets for assessing the methylation status of the concerned gene by way of MSP will specifically hybridize to a converted sequence provided in Table 2, or to its complement sequence. Most preferred primers and primer sets are provided in Table 1 and are represented by SEQ ID NO. 1 to 264. Sense primers comprise or consist essentially of SEQ ID NO. 1 to 132, antisense primers consist essentially of SEQ ID NO. 133 to 264. The amplification products can be optionally hybridized to specific oligonucleotide probes which may also be specific for certain products. Alternatively, oligonucleotide probes can be used which will hybridize to amplification products from both modified and non-modified DNA.

Thus, present invention provides for a method for identifying cervical cancer or its precursor, or predisposition to cervical cancer in a test sample containing cervical cells or nucleic acids from cervical cells comprising: contacting a methylated CpG-containing nucleic acid of at least one gene selected from the group consisting of genes according to Table 1 with bisulfite to convert unmethylated cytosine to uracil; detecting the methylated CpGs in the nucleic acid by contacting the converted nucleic acid with oligonucleotide primers whose sequence discriminates between the bisulfite-treated methylated and unmethylated version of the converted nucleic acid; and identifying the test sample as containing cells that are neoplastic, precursor to neoplastic, or predisposed to neoplasia, or as containing nucleic acids from cells that are neoplastic, precursor to neoplastic, or predisposed to neoplasia.

Modified and non-modified DNA can be distinguished with use of oligonucleotide probes which may also be specific for certain products. Such probes can be hybridized directly to modified DNA or to amplification products of modified DNA. Probes for assessing the methylation status of the concerned gene will specifically hybridize to the converted sequence but not to the corresponding non converted sequence. Probes are designed to anneal specifically with the converted sequence representing either the methylated or unmethylated version of the DNA. Preferred converted sequences are provided in Table 2. Preferred probes anneal specifically with the converted sequence representing the methylated version of the DNA, or to the complement sequence thereof. Oligonucleotide probes can be labeled using detection systems known in the art. These include but are not limited to fluorescent moieties, radioisotope labeled moieties, bioluminescent moieties, luminescent moieties, chemiluminescent moieties, enzymes, substrates, receptors, or ligands.

Another way for the identification of methylated CpG dinucleotides utilizes the ability of the MBD domain of the McCP2 protein to selectively bind to methylated DNA sequences (Cross et al, 1994; Shiraishi et al, 1999). Restriction endonuclease digested genomic DNA is loaded onto expressed His-tagged methyl-CpG binding domain that is immobilized to a solid matrix and used for preparative column chromatography to isolate highly methylated DNA sequences. Variants of this method have been described and may be used in present methods of the invention.

Real time chemistry allows for the detection of PCR amplification during the early phases of the reactions, and makes quantitation of DNA and RNA easier and more precise. A few variants of real-time PCR are well known. They include Taqman® (Roche Molecular Systems), Molecular Beacons®, Amplifluor® (Chemicon International) and Scorpion® DzyNA®, Plexor™ (Promega) etc. The TaqMan® system and Molecular Beacon® system have separate probes labeled with a fluorophore and a fuorescence quencher. In the Scorpion® system the labeled probe in the form of a hairpin structure is linked to the primer.

Quantitation in real time format may be on an absolute basis, or it may be relative to a methylated DNA standard or relative to an unmethylated DNA standard. The absolute copy number of the methylated marker gene can be determined; or the methylation status may be determined by using the ratio between the signal of the marker under investigation and the signal of a reference gene with a known methylation (e.g. β-actin), or by using the ratio between the methylated marker and the sum of the methylated and the non-methylated marker.

Real-Time PCR detects the accumulation of amplicon during the reaction, but alternatively end-point PCR fluorescence detection techniques may be used. Confirming the presence of target DNA at the end point stage may indeed be sufficient and it can use the same approaches as widely used for real time PCR.

DNA methylation analysis has been performed successfully with a number of techniques which are also applicable in present methods of the invention. These include the MALDI-TOFF, MassARRAY (Ehrich, M. et al. 2005), MethyLight (Trinh B. et al. 2001), Quantitative Analysis of Methylated Alleles (Zeschnigk M. et al. 2004), Enzymatic Regional Methylation Assay (Galm et al., 2002), HeavyMethyl (Cottrell, S E et al., 2004), QBSUPT, MS-SNuPE (Gonzalgo and Jones, 1997), MethylQuant (Thomassin H. et al. 2004), Quantitative PCR sequencing, and Oligonucleotide-based microarray systems (Gitan R S et al., 2006).

The number of genes whose modification is tested and/or detected can vary: one, two, three, four, five, six, seven, eight, nine or more genes according to Table 1 can be tested and/or detected. Detection of epigenetic modification of at least one, two, three, four, five, six, seven, eight, nine or more genes according to Table 1 can be used as an indication of cancer or pre-cancer or risk of developing cancer. The genes are preferably selected from the group of JAM3, LMX1A, CDO1, NID2, CCNA1, HOXA11, GREM1 and TAC1. Preferred gene combinations include
 NID2 and HOXA11;
 JAM3, CDO1, HOXA11, and CCNA1;
 JAM3 and HOXA11;
 JAM3, HOXA11 and GREM1;
 JAM3, NID2, HOXA11 and CDO1;
 JAM3, TAC1, HOXA11, and CDO1;
 JAM3, HOXA11, and CDO1;
 JAM3 and CDO1;
 JAM3 and NID2;
 NID2 and CDO1;
 JAM3 and LMX1A
 NID2 and LMX1A, and
 JAM3, CDO1 and NID2.

The accession numbers corresponding to the listed genes can be found at the website for the National Center for Biotechnology Information. Of course, as appropriate, the skilled person would appreciate that functionally relevant variants of each of the gene sequences may also be detected according to the methods of the invention. For example, the methylation status of a number of splice variants may be determined according to the methods of the invention. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences in the database entries. Computer programs for determining percentage nucleotide sequence identity are available in the art, including the Basic Local Alignment Search Tool (BLAST) available from the National Center for Biotechnology Information.

It is possible for the methods of the invention to be used in order to detect more than one gene of interest in the same reaction. Through the use of several specific sets of primers, amplification of several nucleic acid targets can be performed in the same reaction mixture. This may be termed "multiplexing". Multiplexing can also be utilized in the context of detecting both the gene of interest and a reference gene in the same reaction.

The term "test sample" refers to biological material obtained from a mammalian subject, preferably a human subject, and may be any tissue sample, body fluid, body fluid precipitate, or lavage specimen. Test samples for diagnostic, prognostic, or personalized medicine uses can be obtained from cytological samples, from surgical samples, such as biopsies, cervical conization or hysterectomy, from (formalin fixed) paraffin embedded cervix or other organ tissues, from frozen tumor tissue samples, from fresh tumor tissue samples, from a fresh or frozen body fluid such as blood, serum, lymph, or from cervical scrapings, cervical smears, cervical washings and vaginal excretions. Such sources are not meant to be exhaustive, but rather exemplary. A test sample obtainable from such specimens or fluids includes detached tumor cells and/or free nucleic acids that are released from dead or damaged tumor cells. Nucleic acids include RNA, genomic DNA, mitochondrial DNA, single or double stranded, and protein-associated nucleic acids. Any nucleic acid specimen in purified or non-purified form obtained from such specimen cell can be utilized as the starting nucleic acid or acids. The test samples may contain cancer cells or pre-cancer cells or nucleic acids from them. Preferably, the test sample contains squamous cell carcinomas cells or nucleic acids from squamous cell carcinomas, adenocarcinoma cells or nucleic acids of adenocarcinoma cells, adenosquamous carcinoma cells or nucleic acids thereof. Samples may contain mixtures of different types and stages of cervical cancer cells.

Present invention also relates to screening protocols for the screening of woman for cervical cancer and the precursors thereof. Traditionally the Pap Smear has been the primary screening method for the detection of abnormality of the cervix, but its performance is suboptimal. Human Papillomavirus has been associated with the development of cervical cancer. Five high-risk types, 16, 18, 31, 45, and 58, and in particular HPV types 16 and 18 account for approximately 70% of all cervical carcinomas. A small percentage of women showing persistent infection progress from Low-grade to High-grade lesions. The introduction of methylation markers now adds a new dimension to the screening for and treatment of cervical lesions. Method for cervical cancer screening may combine high-risk human papillomavirus (hr-HPV) testing and methylation testing; or cytological evaluation and methylation testing; or hr-HPV testing and cytological evaluation and methylation testing.

Thus, a further embodiment of the present invention relates to a method for cervical cancer detection or screening comprising the steps of:
a) providing a test sample comprising cervical cells or nucleic acids from cervical cells;
b) assaying the test sample of step a) for high-risk human papillomavirus (hr-HPV);
c) if b) is positive for the presence of hr-HPV, assaying the methylation status of at least one gene selected from the group consisting of genes according to Table 1;
d) if the gene of c) is methylated, refer the woman for colposcopy;
e) if the gene of c) is unmethylated, refer the woman to a more regular screening for the presence of hr-HPV.

The present invention relates further to a method for cervical cancer detection or screening comprising the steps of:
a) providing a test sample comprising cervical cells or nucleic acids from cervical cells;
b) assaying the test sample of step a) for hr-HPV;
c) if b) is positive for the presence of hr-HPV, assaying the methylation status of at least one gene selected from the group consisting of genes according to Table 1, and/or typing the hr-HPV for the presence of HPV16 and/or HPV18;
d) if the gene of c) is methylated, and/or HPV16 and/or HPV18 positive, refer the woman for colposcopy;
e) if the gene of c) is unmethylated, refer the woman to a more regular screening for the presence of hr-HPV.

In a related embodiment, the invention provides for a method for cervical cancer detection or screening comprising the steps of:
a) performing cytology evaluation on a test sample comprising cervical cells or nucleic acids from cervical cells;
b) if a) is positive, assaying the methylation status of at least one gene selected from the group consisting of genes according to Table 1;
c) if the at least one gene of b) is methylated, refer the woman for colposcopy;
d) if the at least one gene of b) is unmethylated, refer the woman to cytology testing on a more regular basis.

In a related embodiment, the invention provides for a method for cervical cancer detection or screening comprising the steps of:
a) assaying the methylation status of at least one gene selected from the group consisting of genes according to Table 1;
b) if the at least one gene of b) is methylated, perform cytology testing;
c) if b) is tested positive, refer the woman for colposcopy;
d) if b) is negative, refer the woman to methylation testing on a more regular basis.

In all aspects of the invention, the test sample is preferably a cervical, cervicovaginal or vaginal sample of a woman.

The phrase "cervical cancer screening" refers to organized periodic procedures performed on groups of people for the purpose of detecting cervical cancer.

The phrase "assaying for hr-HPV" refers to testing for the presence of hr-HPV. There are various PCR based assays commercially available to measure hr-HPV copy number or viral load in clinical samples. Many testing methods have been used to detect the presence of HPV in cervicovaginal specimens, including viral load quantification, Southern blot, polymerase chain reaction (PCR), ViraPap (Life Technologies, Gaithersburg, Md.), Hybrid Capture tube testing, Hybrid Capture microtiter plate assays, and CISH. For instance, assaying for hr-HPV may be performed with the FDA approved Hybrid Capture II assay (Digene Corp., Silver Spring, Md.) with a probe cocktail for 13 carcinogenic types.

The so-called "high risk" HPV types are those strains of HPV more likely to lead to the development of cancer, while "low-risk" viruses rarely develop into cancer. The list of strains considered high risk is being adapted with the time and the increase in epidemiological knowledge. As such, those hr-HPV types comprise, without being limited to, strains 16, 18, 31, 33, 35, 39, 45, 51, 52, 56, 58, 59, 68, and 69. Preferred "high risk" HPV types are HPV16 and HPV18.

The phrase "HPV16 testing" refers to testing for the presence of hr-HPV type 16. Similarly, "HPV18 testing" refers to testing for the presence of hr-HPV type 18. The various methods allowing type-specific HPV testing are well known to the person skilled in the art and are applicable in the methods of present invention. For instance, testing for the presence of hr-HPV-16 may be accomplished by PCR amplification using primers specific for HPV type 16, which are known by the skilled in the art.

The phrase "performing cytological evaluation" refers to the cytomorphological assessment of cervical samples, which is usually performed by especially trained medical staff. The various methods allowing cytological testing are well known to the person skilled in the art and are applicable in the methods of present invention. Cytological evaluation may be performed with the known Papanicolaou (PAP) smear test. Alternative means for cytological evaluation include liquid based cytology with for example the ThinPrep technique (Cytyc Corporation, Marlborough, Mass., USA).

The term "triaging" refers to sorting out or classifying patients in order to establish priority of treatment's necessity, priority of proper place of treatment, or any other priority in terms of patient management.

The test sample will most of the time be obtained from a subject suspected of being tumorigenic or from a subject undergoing routine examination and not necessarily being suspected of having a disease. Alternatively the sample is obtained from a subject undergoing treatment, or from patients being checked for recurrence of disease.

Testing can be performed diagnostically or in conjunction with a therapeutic regimen. Testing can be used to monitor efficacy of a therapeutic regimen, whether a chemotherapeutic agent or a biological agent, such as a polynucleotide. Epigenetic loss of function of at least one gene selected from the group consisting of genes according to Table 1 can be rescued by the use of DNA demethylating agents and/or DNA methyltransferase inhibitors. Testing can also be used to determine what therapeutic or preventive regimen to employ on a patient. Moreover, testing can be used to stratify patients into groups for testing agents and determining their efficacy on various groups of patients.

Demethylating agents can be contacted with cells in vitro or in vivo for the purpose of restoring normal gene expression to the cell. Suitable demethylating agents include, but are not limited to 5-aza-2'-deoxycytidine, 5-aza-cytidine, Zebularine, procaine, and L-ethionine. This reaction may be used for diagnosis, for determining predisposition, and for determining suitable therapeutic regimes. Accordingly, the invention also provides for a method for predicting the likelihood of successful treatment or resistance to treatment of cancer with such agent. If the gene is methylated, the likelihood of successful treatment is higher than if the gene is unmethylated, or methylated to a lesser degree. Conversely, if the gene is unmethylated, or methylated to a lesser degree, the likelihood of resistance to treatment is higher than if the gene is methylated.

In a related aspect, epigenetic loss of gene function(s) can identify the stage of the disease and from that the need of treatment. Accordingly, the invention provides for a method for predicting suitable treatment comprising determining the methylation status of a gene or a combination of genes. If the gene is methylated, the need of cervical resection is identified; if the gene is unmethylated or methylated to a lesser degree, it is decided that there is no need for cervical resection. In cases of early stage (CIN) and carcinoma in situ, abnormal tissue is removed by cryosurgery, laser surgery, conization, or simple hysterectomy (removal of the uterus). Invasive cervical cancer is treated with radical hysterectomy (removal of the uterus, fallopian tubes, ovaries, adjacent lymph nodes, and part of the vagina).

To attain high rates of tumor detection, it may be necessary to combine the methods of the invention with established methods and/or markers for cervical cancer identification (Malinowski D, 2007), such as morphology-based detection methods, HPV methylation testing (Badal et al. 2004, Kalantari et al. 2004), KRAS and BRAF mutation detection (Kang et al. 2007), chromosomal amplification (Rao et al. 2004), protein expression (Keating et al. 2001) and HPV detection methods (Brink et al. 2007): several HPV detection kits are known in the art and commercially available, for example kits such as Digene® HPV Test (Qiagen), AMPLICOR HPV Test (Roche), HPV High-Risk Molecular Assay (Third Wave Technologies), LINEAR ARRAY HPV Genotyping Test (Roche), INNO-LiPA HPV Genotyping (Innogenetics), PapilloCheck (Greiner Bio-One GmbH), PreTect HPV-Proofer (Norchip), NucliSENS EasyQ HPV (BioMerieux), F-HPV Typing™ (molGENTIX, S.L.) may be utilized. Such examples are not meant to be exhaustive, but rather exemplary.

Another aspect of the invention is a kit for assessing methylation in a test sample. Kits according to the present invention are assemblages of reagents for testing methylation. They are typically in a package which contains all elements, optionally including instructions. The package may be divided so that components are not mixed until desired. Components may be in different physical states. For example, some components may be lyophilized and some in aqueous solution. Some may be frozen. Individual components may be separately packaged within the kit. The kit may contain reagents, as described above for differentially modifying methylated and non-methylated cytosine residues.

Desirably the kit will contain oligonucleotide primers which specifically hybridize to regions within about 10 kbp, within about 5 kbp, within about 3 kbp, within about 1 kbp, within about 750 bp, within about 500 bp, within 200 bp or within 100 bp kb of the transcription start sites of the genes/markers listed in Table 1.

Typically the kit will contain both a forward and a reverse primer for a single gene or marker. If there is a sufficient region of complementarity, e.g., 12, 15, 18, or 20 nucleotides, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues. The kit may optionally contain oligonucleotide probes. The probes may be specific for sequences containing modified methylated residues or for sequences containing non-methylated residues. The kit may optionally contain reagents for modifying methylated cytosine residues. The kit may also contain components for performing amplification, such as a DNA polymerase and deoxyribonucleotides. Means of detection may also be provided in the kit, including detectable labels on primers or probes. Kits may also contain reagents for detecting gene expression for one of the markers of the present invention. Such reagents may include probes, primers, or antibodies, for example. In the case of enzymes or ligands, substrates or binding partners may be sued to assess the presence of the marker. Kits may contain 1, 2, 3, 4, or more of the primers or primer pairs of the invention. Kits that contain probes may have them as separate molecules or covalently linked to a primer for amplifying the region to which the probes hybridize. Other useful tools for performing the methods of the invention or associated testing, therapy, or calibration may also be included in the kits, including buffers, enzymes, gels, plates, detectable labels, vessels, etc.

According to a further aspect, the invention also employs or relies upon or utilizes oligonucleotide primers and/or probes to determine the methylation status of at least one gene selected from a group of genes consisting of JAM3, LMX1A, CDO1, NID2, ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, GPNMB, GREM1, Gst-Pi, HHIP, HIN1, HOOK2, HOXA1, HOXA11, HOXA7, HOXD1, IGSF4, ISYNA1, JPH3, KNDC1, KRAS, LAMA1, LOC285016, LOX, LTB4R, MAL, MTAP, MYO18B, NDRG2, NOL4, NPTX1, NPTX2, OGFOD2, PAK3, PAX1, PDCD4, PHACTR3, POMC, PRKCE, RAD23B, RALY, RARA, RASSF1A, RBP4, RECK, RPRM, SALL4, SEMA3F, SLC5A8, SLIT1, SLIT2, SLIT3, SMPD1, SOCS1, SOX1, SOX17, SPARC, SPN, SST, TAC1, TERT, TFPI-2, TLL1, TNFAIP1, TRMT1, TWIST1, UGT1A1, WIF1, WIT1, WT1, XRCC3, and ZGPAT. Preferred probes and their sequences bind to at least one of the polynucleotide sequences listed in Table 2, FIG. 5B or to the complement sequence thereof. Preferred primers and probes are selected from the primers and probes comprising or consisting essentially of the nucleotide sequences set forth in Table 1. Related to this, the invention also provides for an isolated polynucleotide which consists of a nucleotide sequence listed in Table 1, Table 2 and FIG. 5B.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

TABLE 1

MSP assays and primer design

| Row Nr | Assay Name | Gene ID | Official Gene Symbol | Refseq | Sense Primer sequence (5'-3') SEQ ID NO's 1-132 | Antisense Primer sequence (5'-3') SEQ ID NO's 133-264 |
|---|---|---|---|---|---|---|
| 1 | ALX3_25178 | 257 | ALX3 | NM_006492 | GTTTGGTTCGGGTTAGCGT | CCTACTTATCTCTCCCGCTCG |
| 2 | ALX3_25180 | 257 | ALX3 | NM_006492 | TTGCGTTTTATTTGTATTTCGC | CTTAACGAACGACTTAACCGACT |
| 3 | ALX4_25062 | 60529 | ALX4 | NM_021926 | TTTTATTGCGAGTCGTCGGTC | TATACCGAACTTATCGCCTCCG |
| 4 | AR_24818 | 367 | AR | NM_000044, NM_001011645 | TGTATAGGAGTCGAAGGGACGTA | AAACAACTCCGAACGACGA |
| 5 | ARID4A_24110 | 5926 | ARID4A | NM_002892 | GTTAGGTAAGTGGTACGGCGA | AAAAACGACTACAACTACGACGA |
| 6 | ARID4A_24112 | 5926 | ARID4A | NM_002892 | ATTTAATGAGGACGGTAGGTAGC | AACAAACTCGCTTCTACACGAA |
| 7 | ATM_9746 | 472 | ATM | XM_940791, NM_900051, NM_138292 | TTTAATATAAGTCGGGTTACGTTCG | ATACGACGCAAAAACTATCGC |
| 8 | AURKA_24802 | 6790 | AURKA | NR_001587, NM_003600 | TTAGGGAGTAAGTGCGTTTGC | AAAAACCGATTAACCTACGCTC |
| 9 | B4GALT1_1 | 2683 | B4GALT1 | NM_001497 | TAGACGGTTACGAGTAGGCGGTA | CCTTCTTAAAACGACGACGAA |
| 10 | B4GalT1_3 | 2683 | B4GALT1 | NM_001497 | TTTTTCGTATTTTAGGAAGTGGC | TTCCTCCCGAACCTTTACGA |
| 11 | BMP2_17901 | 650 | BMP2 | NM_001200 | TTTGGGGTTCGATTATATTTC | CGAAAACTCCGAAACCGAT |
| 12 | BMP6_24310 | 654 | BMP6 | NM_001718 | GTTATTTTCGGCGGGTTC | CTAATAATCGCCCCTTCGC |
| 13 | BNIP3 | 664 | BNIP3 | NM_004052 | TACGCGTAGGTTTTAAGTCGC | TCCCGAACTAAACGAAACCCCG |
| 14 | C13orf18_19885 | 80183 | C13orf18 | NM_025113 | TTTGATTTTGAAAGCGTCGT | ACACCACGCACCTATACGC |
| 15 | C13orf18_Gron | 80183 | C13orf18 | NM_025113 | TTTTTAGGGAAGTAAAGCGTCG | ACGTAATACTAAACCCGAACGC |
| 16 | C16orf48_22922 | 84080 | C16orf48 | NM_032140 | TAGTTTGGTAGTTAGCGGGTC | AAACCTCCGAAATAACCGTC |
| 17 | C9orf19_19865 | 152007 | C9orf19 | NM_022343 | ATAGGGGAGTTCGGTACG | ACAATTTACCCCGCTCGACT |
| 18 | CALCA_2 | 796 | CALCA | NM_001033952 NM_001033953 NM_001741 | CGTTTTTATAGGGTTTTGGTTGGAC | AAATCTCGAAACTCACCTAACGA |
| 19 | CAMK4_27356 | 814 | CAMK4 | NM_001744 | TAGTTGTATCGGTTAGGCGTTT | CTACCTTCGTACCCTTCGATT |
| 20 | CCNA1_gron | 8900 | CCNA1 | NM_003914 | GTTATGGCGATGCGGTTTC | CCAACCTAAAAACGACCGA |
| 21 | CCND2_25209 | 894 | CCND2 | NM_001759 | GAAGGTAGCGTTTTCGATG | AAATAAACCCGATCCGCAA |
| 22 | CDH1_17968 | 999 | CDH1 | NM_004360 | AATTTTAGGTTAGAGGGTTATCGC | ACCAATCAACAACGCGAAC |
| 23 | CDH1_23527 | 999 | CDH1 | NM_004360 | GAGGGGGTAGGAAAGTCGC | CGAAACGACCTAAAAACCTCG |
| 24 | CDH4_24735 | 1002 | CDH4 | NM_001794 | GGGACGATTTTTCGTTGTTC | TTCTACTACTCTCGCTCTCCGAC |

TABLE 1-continued

MSP assays and primer design

| Row Nr | Assay Name | Official Gene ID | Gene Symbol | Refseq | Sense Primer sequence (5'-3') SEQ ID NO's 1-132 | Antisense Primer sequence (5'-3') SEQ ID NO's 133-264 |
|---|---|---|---|---|---|---|
| 25 | CDK6_9703 | 1021 | CDK6 | NM_001259 | AATTTCGTTTGTAGAGTCGTCGT | TCTATATTAAAAACTTCGCTTCG |
| 26 | CDKN1B_23172 | 1027 | CDKN1B | NM_004064 | GTCGGTAAGGTTTGGAGAGC | AAAATAACAAAACCCGTCCG |
| 27 | CDKN2B_27345 | 1030 | CDKN2B | NM_004936 | TTAGAAGTAATTTAGGCGCGTTC | AAACCCCGTACAATAACCGA |
| 28 | CDO1_55928 | 1036 | CDO1 | NM_001801 | AATTTGATTTGTGTGTGTATCGC | GAAACGTAAAAATATCGTCGCA |
| 29 | CDO1_55929 | 1036 | CDO1 | NM_001801 | GTTTACGCGATTTTTGGGAC | AAAAACCCTACGAACACGACT |
| 30 | CLSTN2_19850 | 64084 | CLSTN2 | NM_022131 | AGGGTTTTCGGAGTCGTT | TTCCTCAACCGTCTCCACG |
| 31 | CLU_13810 | 1191 | CLU | NM_001831, NM_203339 | AGGCGTCGTATTTATAGCGTTT | TCCCCTTACTTTCCGCGAC |
| 32 | CLU_19838 | 1191 | CLU | NM_001831, NM_203339 | GTGGGGGTCGGTGTAGTATC | TCCCTACTAAAAACGCCGAA |
| 33 | COL1A1_23253 | 1277 | COL1A1 | NM_000088 | TATAAAAGGGGTTCGGGTTAGTC | AAATTAACGTCCGCTCATACG |
| 34 | CPT1C_23912 | 126129 | CPT1C | NM_152359 | AGGAAGTATTTATTGCGTATGTTTC | CCATCACTTATCCTCGACGC |
| 35 | CTDSPL_23795 | 10217 | CTDSPL | NM_001008392 | TAATTTTAAGGAGGACGAGGGTC | ATAAACTCCAACGACGCGAAA |
| 36 | CTDSPL_23804 | 10217 | CTDSPL | NM_005808 | GTTTTGGGAGAGGCGGTTC | TCATAATAACGAAACGACGACC |
| 37 | CYCLIND2_1 (official full gene name for CCND2) | 894 | CCND2 | NM_001759 | GGTGTAGCGTTTAGGGTCGTC | CGAATTTTCCTACGTAACCG |
| 38 | DAPK1 | 1612 | DAPK1 | NM_004938 | GGATAGTCGGATCGAGTTAACGTC | CCCTCCCAAACGCCGA |
| 39 | DBC1_23879 | 1620 | DBC1 | NM_014618 | AGGATAGGTATGAATTTCGGTTTC | AAACGAACGAACAACACGA |
| 40 | DDX19B_22963 | 11269 | DDX19B | NM_007242, NM_001014449, NM_001015047 | CGGGTTTGAGGGTAATAGAATCG | CGCCACAATAACGTCGAAA |
| 41 | DKK2_23970 | 27123 | DKK2 | NM_014421 | GTGCGGGGTAAGAAGGAAC | AAAAACAATCAAATACGAAACGC |
| 42 | DKK2_23973 | 27123 | DKK2 | NM_014421 | GAGAGAGAAAGCGGGAGTTC | TCACAATTACCCCGAAACG |
| 43 | EGFR_23302 | 1956 | EGFR | NM_201283, NM_005228 | TAGGAGCGTTGTTTCGGTC | CACGACCCCCTAACTCCGT |
| 44 | EGR4_24277 | 1961 | EGR4 | NM_001965 | TTTAGGTGGGAAGCGTATTTATC | AAACGCTAAAACCGCGAAT |
| 45 | EPB41L3_19071 | 23136 | EPB41L3 | NM_012307 | GGGATAGTGGGGTTGACGC | ATAAAAATCCCGACGAACGA |
| 46 | EPB41L3_19072 | 23136 | EPB41L3 | NM_012307 | GCGTGGGTTTTCGTCGTAG | CCCAAAACTACTCGCCGCT |
| 47 | FOS_22338 | 2353 | FOS | NM_005252 | CGGGTTGTAGTTAATATCGAGG | CTCTCTCATTCTACGCCGTTC |
| 48 | FOXE1_13314 | 2304 | FOXE1 | NM_004473 | TTTGTTCGTTTTTCGATTGTTC | TAACGCTATAAAACTCCTACCGC |

TABLE 1-continued

MSP assays and primer design

| Row Nr | Assay Name | Gene ID | Official Gene Symbol | Refseq | Sense Primer sequence (5'-3') SEQ ID NO's 1-132 | Antisense Primer sequence (5'-3') SEQ ID NO's 133-264 |
|---|---|---|---|---|---|---|
| 49 | GADD45A_24463 | 1647 | GADD45A | NM_001924 | CGTTAATCGGATAAGAGTGCG | AAAACCACGCGAAAAACGA |
| 50 | GATA4 | 2626 | GATA4 | NM_002052 | GTATAGTTTCGTAGTTTGCGTTTAGC | AACTCGCGACTCGAATCCCCG |
| 51 | GATA4_13295 | 2626 | GATA4 | NM_002052 | GGTATTGTTATTTTGCGTTTTC | CCCGAAACAAACTACACGAC |
| 52 | GDAP1L1_19773 | 78997 | GDAP1L1 | NM_024034 | GATTTCGGGTTGTTATGGC | CTAACTTAACCGCATCGCTC |
| 53 | GDAP1L1_19775 | 78997 | GDAP1L1 | NM_024034 | GAAAGAAGGAGGTTTCGGC | CCCGATAATAATAACATTCACGA |
| 54 | GNB4 | 59345 | GNB4 | NM_021629 | GTTGTGAGTTGCGTTTTTTACGTC | CGCTACCGATATCCGCTAAACG |
| 55 | GPNMB_52607 | 10457 | GPNMB | NM_001005340 | GGTCGTAGTCGTAGTCGGG | CCGCAAAAACCTAAAACGTAA |
| 56 | GREM1_29777 | 26585 | GREM1 | NM_013372 | GAATTTGGTACGATTTTACGGAG | ATCTAAACTTTCCCTATCGACCG |
| 57 | Gst-Pi_New3 | 2950 | GSTP1 | NM_000852 | ATTTAGTATTGGGCGGAGC | TAACGAAAACTACGACGACGA |
| 58 | HHIP_23319 | 64399 | HHIP | NM_022475 | AGTAGTAGGAATAGAAACGGCGA | AAAACTACAACCGCCACA |
| 59 | HIN1_3 | 92304 | SCGB3A1 | NM_052863 | GAAGTTGGTTAGGGTACGGTC | AACTTCTTATACCCGATCCTCG |
| 60 | HOOK2_19741 | 29911 | HOOK2 | NM_013312 | GGATCGTTGGATTTTGGTTC | TATATCCTCGCCCCACGTAA |
| 61 | HOXA1_27316 | 3198 | HOXA1 | NM_153620 | TTTTTAGAGTAAATAGCGGGAGC | ATACGCCTTACAACCCCTACG |
| 62 | HOXA11_23844 | 3207 | HOXA11 | NM_005523 | TTTTATTTATTCGGGGAGTTGC | ACAAATCCTCGTTCTCGAAT |
| 63 | HOXA7_2 | 3204 | HOXA7 | NM_006896 | TCGTAGGGTTCGTAGTCGTTT | TCCAAATCTTTTTCCGCGA |
| 64 | HOXD1(2) | 3231 | HOXD1 | NM_024501 | GTCGGTTGACGTTTTGAGATAAGTC | ACCGTCTTCTCGAACGACG |
| 65 | IGSF4_18987 | 23705 | CADM1 | NM_014333 | TCGGATTTCGTTTTTAGCGTAT | GAACACCTACCTCAAACTAACGAC |
| 66 | ISYNA1_19726 | 51477 | ISYNA1 | NM_016368 | TAGGTTGGTTTGGTTTCGGTC | TAAACGACGACCTCCATCG |
| 67 | JAM3 | 83700 | JAM3 | NM_032801 | GGGATTATAAGTCGCGTCGC | CGAACGCAAAACCGAAATCG |
| 68 | JPH3_12611 | 57338 | JPH3 | NM_020655 | TTAGATTTCGTAAACGGTGAAAC | TCTCCTCCGAAAAACGCTC |
| 69 | KNDC1_19691 | 85442 | KNDC1 | NM_033404 NM_152643 | TGGATGGAGTTTAGGTTATATCGTC | AAAATACTACGAAACCGCCC |
| 70 | KRAS_24235 | 3845 | KRAS | NM_033360 | AGGAGGGATTGTCGGATTTAC | GCTCCGAATCAAAATTAACGA |
| 71 | LAMA1_63431 | 284217 | LAMA1 | NM_005559 | TTTTTAGATTTATCGAGTGGCG | CGAACTCACCTCTCTACCGAC |
| 72 | LMX1A_9513 | 4009 | LMX1A | NM_177398, NM_177399, NM_001033507 | CGGTATCGTTGTTTAGGAGGC | CGTATAACTATTACCTCGAAACGCT |

TABLE 1-continued

MSP assays and primer design

| Row Nr | Assay Name | Official Gene ID | Gene Symbol | Refseq | Sense Primer sequence (5'-3') SEQ ID NO's 1-132 | Antisense Primer sequence (5'-3') SEQ ID NO's 133-264 |
|---|---|---|---|---|---|---|
| 73 | LOC285016_22940 | 285016 | hCG_1990170 | NM_001002919 | AGTTGTTTGGTATTCG CGGT | CGACCCCTCCTAACTTT CG |
| 74 | LOX_23395 | 4015 | LOX | NM_002317 | GTTAGATTGATTTCGT TCGAGG | AACTAAAATACCCGTAC TCCGCT |
| 75 | LTB4R_31250 | 1241 | LTB4R | NM_181657 | TAGTAGATTTTTAGCG GTGAAGACG | AAAACCTTAACGAAACT AAACGAAA |
| 76 | MAL | 4118 | MAL | NM_002371 | TTCGGGTTTTTTGTT TTTAATTC | GAAAACCATAACGACGT ACTAACG |
| 77 | MTAP_24628 | 4507 | MTAP | NM_002451 | GTAAGTGAGTTTCGA GTGTCGC | CTCCGAAAACCATACGC CC |
| 78 | MYO18B_24620 | 84700 | MYO18B | NM_032608 | GAAAGGTCGGATTTG TTTTTC | ACCATCTCATCACGCCT CG |
| 79 | NDRG2_56603 | 57447 | NDRG2 | NM_201540 NM_201539 NM_201535 NM_201537 | AGATTTTGTGGTTTCG TCGTT | ATCCCCGAACATTACG ATT |
| 80 | NID2_9091 | 22795 | NID2 | NM_007361 | GCGGTTTTAAGGAGT TTTATTTTC | CTACGAAATTCCCTTTA CGCT |
| 81 | NOL4_19645 | 8715 | NOL4 | NM_003787 | GAGAGATTCGGGATT CGTG | GTAATCCAAAAATAAAA ACTACGCC |
| 82 | NPTX1_2 | 4884 | NPTX1 | NM_002522 | AGTACGTTGTTTCGGA GTTTTTC | CTTCATCTACACCTCGA TACCCG |
| 83 | NPTX2_57779 | 4885 | NPTX2 | NM_002523 | GCGTCGTTTTGTATGG GTATC | CCCGATAACCGCTTCGT AT |
| 84 | OGFOD2_23131 | 79676 | OGFOD2 | NM_024623 | CGAGTAGTAGTTGCG TCGGG | ACAAACGACCCTAAAAA CGAAC |
| 85 | PAK3_1 | 5063 | PAK3 | NM_002578 | TGTATGATTTTAGTTC GCGGAT | ACGAATTTTACCTCAAA CGACC |
| 86 | PAK3_3 | 5063 | PAK3 | NM_002578 | GCGGGATTTATTTGTT ACGGA | AACCCGAAACTACGACT ACGAC |
| 87 | PAX1_27210 | 5075 | PAX1 | NM_006192 | ATTGCGTCGGGTTTA GTTTC | GCCCCTTACCCATAACG AAC |
| 88 | PAX1_27211 | 5075 | PAX1 | NM_006192 | GTTTAGGGAAAGCGG ACGA | GAACGACAAACAAAACT CGAAA |
| 89 | PDCD4_11827 | 27250 | PDCD4 | NM_145341, NM_014456 | GTTCGTAGTTCGGGG CGTT | GCGATCCTATCAAATCC GAA |
| 90 | PHACTR3_11692 | 116154 | PHACTR3 | NM_080672 NM_183244 NM_183246 | TTATTTTGCGAGCGGT TTC | GAATACTCTAATTCCAC GCGACT |
| 91 | POMC | 5443 | POMC | NM_000939 | GATTTGGGCGTTTTTG GTTTTTCGC | GACTTCTCATACCGCAA TCG |
| 92 | PRKCE_24134 | 5581 | PRKCE | NM_005400 | GTGGGTTTTAAGTTTA CGGTTTC | CCTACCCTCGAAACAAA CGA |
| 93 | RAD23B_1 | 5887 | RAD23B | NM_002874 | GGCGGAGTTTGTATA GAGGC | AACCCGAATTACGCAAA CG |
| 94 | RALY_19607 | 22913 | RALY | NM_007367 | TTTTTGGGTTCGTTG TTTC | CGCCTCAATAATACCGA CC |
| 95 | RARA_24121 | 5914 | RARA | NM_001024809 | TTCGTTTCGTTTAGGT ATCGTTT | CCTCTCGATTCCCTACG TTT |
| 96 | RARA_24129 | 5914 | RARA | NM_000964, NM_001033603 | TTTAGGATTATAGTGA GCGACGG | TAACCGCCTTTAACCCC GA |

TABLE 1-continued

MSP assays and primer design

| Row Nr | Assay Name | Gene ID | Official Gene Symbol | Refseq | Sense Primer sequence (5'-3') SEQ ID NO's 1-132 | Antisense Primer sequence (5'-3') SEQ ID NO's 133-264 |
|---|---|---|---|---|---|---|
| 97 | RASSF1A | 11186 | RASSF1 | NM_007182. NM_170712 NM_170714 | GCGTTGAAGTCGGGG TTC | CCCGTACTTCGCTAACT TTAAACG |
| 98 | RBP4_24106 | 5950 | RBP4 | NM_006744 | GGTCGTTTCGTTGTTT TATAGC | GCGTTATACAAATACCC CCG |
| 99 | RECK_18940 | 8434 | RECK | NM_021111 | TTACGGTTAGTAGAAG GAGTAGCGT | CTACGACCAAACTAAAT CCGAAC |
| 100 | RPRM_2 | 56475 | RPRM | NM_019845 | TCGAGGAAGAAGATG TCGAAG | AAAAACCCGAACGAAC GTAA |
| 101 | SALL4_12833 | 57167 | SALL4 | NM_020436 | GAGGCGTAAGTAGGC GAAA | CGCATCTACAAACTCCG AAA |
| 102 | SEMA3F_23485 | 6405 | SEMA3F | NM_004186 | GATTAGAGCGAGCGA ACGA | TAACTACTAAACCCGAA CCGAAC |
| 103 | SLC5A8_24598 | 160728 | SLC5A8 | NM_145913 | GGTTTGTTGGTCGTTT TTAGC | CGAAACATCGACACCTT CGT |
| 104 | SLC5A8_24601 | 160728 | SLC5A8 | NM_145913 | GTATTTAGGGTAGCG GGTCG | CGAAATAAAAACTAACA ATCGCC |
| 105 | SLIT1_23651 | 6585 | SLIT1 | NM_003061 | GCGTTATGGTGTTTTT ATAGCGT | TCTTCGATAACTCTACC CCGA |
| 106 | SLIT1_23653 | 6585 | SLIT1 | NM_003061 | TTGTAGGCGGTTTGTA GTCGT | GACAATCATCCATCAAT CGAAA |
| 107 | SLIT2_23672 | 9353 | SLIT2 | NM_004787 | GAGGATCGGTTTAGG TTGC | CAATTCTAAAAACGCAC GACT |
| 108 | SLIT2_23676 | 9353 | SLIT2 | NM_004787 | AGGGGAAGACGAAGA GCGT | CACGAACTAACGCTACG CAA |
| 109 | SLIT2_23681 | 9353 | SLIT2 | NM_004787 | TAGCGGAGAGGAGAT TACGC | GACCCCTACATCTTAAC AACCG |
| 110 | SLIT3_23619 | 6586 | SLIT3 | NM_003062 | AGGGGTATTTATAGG CGTTTAGC | TACCTACTCCGCTACCA ACGTAA |
| 111 | SMPD1_24061 | 6609 | SMPD1 | NM_000543 | GAAGGGTAATCGGGT GTTTTC | CTAATTCGTCTATCCCG TCC |
| 112 | SOCS1_23595 | 8651 | SOCS1 | NM_003745 | GATAGGGTTTTGTTTT CGGC | ATTTTACCCCGCTACCT CG |
| 113 | SOX1_27153 | 6656 | SOX1 | NM_005986 | TTGTAGTTTTCGAGTT GGAGGTC | AAAACGATACGCTAAAC CCG |
| 114 | SOX1_27159 | 6656 | SOX1 | NM_005986 | GTTAGGAGTTCGTCG GTTAGC | CACCCGAATTACAAATA CCGA |
| 115 | SOX17_66072 | 64321 | SOX17 | NM_22454 | GAGATGTTTCGAGGG TTGC | CCGCAATATCACTAAAC CGA |
| 116 | SPARC_Wis | 6678 | SPARC | NM_003118 | TTTCGCGGTTTTTAG ATTGTTC | CATACCTCAATAACAAA CAAACAAACG |
| 117 | SPN_24052 | 6693 | SPN | NM_003123, NM_001030288 | ATCGTAGGTTGGGTTT GGTC | AAAAACAAACACGCGA AA |
| 118 | SST_23808 | 6750 | SST | NM_001048 | TGGTTGCGTTGTTTAT CGTTT | TTACCTACTTCCCCGCG AC |
| 119 | TAC1_56187 | 6863 | TAC1 | NM_003182 | GGGTATTTATTGCGAC GGAT | CCGACGACAACTACCG AAA |
| 120 | TERT_23702 | 7015 | TERT | NM_003219, NM_198255 | GGTTTCGATAGCGTA GTTGTTTC | CTACACCCTAAAAACGC GAAC |

TABLE 1-continued

MSP assays and primer design

| Row Nr | Assay Name | Gene ID | Official Gene Symbol | Refseq | Sense Primer sequence (5'-3') SEQ ID NO's 1-132 | Antisense Primer sequence (5'-3') SEQ ID NO's 133-264 |
|---|---|---|---|---|---|---|
| 121 | TFPI-2 | 7980 | TFPI2 | NM_006528 | GTTCGTTGGGTAAGG CGTTC | CATAAAACGAACACCCG AACCG |
| 122 | TLL1_24051 | 7092 | TLL1 | NM_012464 | TAAGGAATTTTGTATT CGGAGGC | ACCTAACAAACTACGAA CGCCA |
| 123 | TNFAIP1_23212 | 7126 | TNFAIP1 | NM_021137 | GTGGTTAGCGGATTT CGAGT | AACTAAACAACACTCCG AACGA |
| 124 | TRMT1_19794 | 55621 | TRMT1 | NM_017722 | TTTCGTAGGGTTCGGT GTC | CCGAATACTCTCTAAAA CCCGAT |
| 125 | TWIST1_3 | 7291 | TWIST1 | NM_000474 | GTTAGGGTTCGGGGG CGTTGTT | CCGTCGCCTTCCTCCG ACGAA |
| 126 | TWIST1_9329 | 7291 | TWIST1 | NM_000474 | TTTAGTTCGTTAGTTT CGTCGGT | TACTACTACGCCGCTTA CGTCC |
| 127 | UGT1A1_22912 | 54658 | UGT1A1 | NM_007120 | TTTTGTGGTTAGTCGC GGT | ACGTAAAATAAACAATC AACTATCG |
| 128 | WIF1_9096 | 11197 | WIF1 | NM_007191 | GCGTCGTTAGATATTT TGTTGC | TAACACCCAAACCGAAA AACG |
| 129 | WIT1_24567 | 51352 | WIT1 | NM_015855 | GTATGGAGCGTTTTG CGAT | AACGAATCCACATACCC GA |
| 130 | WT1_1 | 7490 | WT1 | NM_024426, NM_024424 | TGTGTTATATCGGTTA GTTGAGAGC | CGCTACTCCTTAAAAAC GCC |
| 131 | XRCC3_9322 | 7517 | XRCC3 | NM_005432 | CGTTTGTTTTTATAGG TTCGGG | ACAACGAAATCGAAAAT CGTAA |
| 132 | ZGPAT_23961 | 84619 | ZGPAT | NM_032527 NM_181484 NM_181485 | TGTATGCGGAGAGGT CGTAG | ACCATTCCCGACTCCTC GT |

TABLE 2

Amplicon details (converted sequences issuing from the methylated version of the DNA)

| Row Nr | Assay Name | Gene ID | Official Gene Symbol | Refseq | Amplicon Sequence (converted) (5'-3') SEQ ID NO's 265-396 |
|---|---|---|---|---|---|
| 1 | ALX3_25178 | 257 | ALX3 | NM_006492 | GTTTGGTTCGGGTTAGCGTTAATTCGGTTTTCGTGG AAGTCGTGGCGAAAGGCGAGAGGGGTAAAAGTTG AGAAATAGGCGAGCGGGAGAGATAAGTAGG |
| 2 | ALX3_25180 | 257 | ALX3 | NM_006492 | TTGCGTTTTATTTGTATTTCGCGTCGTTTCGCGGTTC GCGGTTGATTCGTTTTTCGGTTTGCGGGTTTTTGGA GTTTTATTTTTTAGAGTCGGTTAAGTCGTTCGTTAAG |
| 3 | ALX4_25062 | 60529 | ALX4 | NM_021926 | TTTTATTGCGAGTCGTCGGTCGTTGTTATGGACGTTT ATTATAGTTCGGTGTCGTAGAGTCGGGAGGGTTCGT CGTTTTTTAGGGTATTTTTCGGAGGCGATAAGTTCG GTATA |
| 4 | AR_24818 | 367 | AR | NM_000044, NM_001011645 | TGTATAGGAGTCGAAGGGACGTATTACGTTAGTTTT AGTTCGGTTTTAGCGATAGTTAACGTTTTTTGTAGCG CGGCGGTTTCGAAGTCGTCGTTCGGAGTTGTTT |
| 5 | ARID4A_24110 | 5926 | ARID4A | NM_002892 | GTTAGGTAAGTGGTACGGCGAGCGTAAGGGAAGGG GTTAGTTATTGATTAGCGGTAGTAATTGTAGGAATCG TCGTCGTAGTTGTAGTCGTTTTT |
| 6 | ARID4A_24112 | 5926 | ARID4A | NM_002892 | ATTTAATGAGGACGGTAGGTAGCGAGGTTTTATTCG AAGTTTTTCGGCGTTATGAGTAGTTAATAGGAGTTC GTGTAGAAGCGAGTTTTGTT |

TABLE 2-continued

Amplicon details (converted sequences issuing from the methylated version of the DNA)

| Row Nr | Assay Name | Official Gene ID | Gene Symbol | Refseq | Amplicon Sequence (converted) (5'-3') SEQ ID NO's 265-396 |
|---|---|---|---|---|---|
| 7 | ATM_9746 | 472 | ATM | XM_940791, NM_000051, NM_138292 | TTTAATATAAGTCGGGTTACGTTCGAGGGTAATAATA TGATTAAAATTATAGTAGGAATTATAATAAGGAATAA GATTTAGGTTAAAGTAAATATAGCGATAGTTTTTGCG TCGTAT |
| 8 | AURKA_24802 | 6790 | AURKA | NR_001587, NM_003600 | TTAGGGAGTAAGTGCGTTTGCGCGCGGTGTGCGTT TTTAAACGCGATTTAAGGCGTCGGGTTTGTTGTTAAT TAATTATAAGGTAGTTTCGTTCGAGCGTAGGTTAATC GGTTTTT |
| 9 | B4GALT1_1 | 2683 | B4GALT1 | NM_001497 | TAGACGGTTACGAGTAGGCGGTAGGTTCGTTGTAG GGACGCGTTTGGTATCGCGGCGTTGTCGTTTAGGA GCGGTTTTCGAAGTTTTATTTTTTCGTCGTCGTTTTA AGAAGG |
| 10 | B4GalT1_3 | 2683 | B4GALT1 | NM_001497 | TTTTTCGTATTTTAGGAAGTGGCGCGGTTTGTCGAG GGTAGCGTGGAGGAGGAAGAGGAGGCGCGGTTTAA CGCGATCGAAGTTTCGTCGTAAAGGTTCGGGAGGAA |
| 11 | BMP2_17901 | 650 | BMP2 | NM_001200 | TTTGGGGTTCGATTATATTTCGGTTAGCGCGTTTTAG GTTTTCGATTTTTTGTAGTAGGTGTTTCGTATCGCGG CGTTAGGGATCGGTTTCGGAGTTTTCG |
| 12 | BMP6_24310 | 654 | BMP6 | NM_001718 | GTTATTTTCGGCGGGTTCGTTTTTTTTTTTGGTTTT TAGTTTTTATTTTTATGGTCGTTCGGGGCGTTTTA GTTGTTTAGGTTAGAGAGGTGGCGAAGGGGCGATT ATTAG |
| 13 | BNIP3 | 664 | BNIP3 | NM_004052 | TACGCGTAGGTTTTAAGTCGCGGTTAATGGGCGACG CGGTCGTAGATTCGTTCGGTTTCGTTTGTTTTGTGA GTTTTTTCGTCGGGTTGCGGGGTTTCGTTTAGTTC GGGA |
| 14 | C13orf18_19885 | 80183 | C13orf18 | NM_025113 | TTTGATTTTTGAAAGCGTCGTTGCGTTTCGCGTCGC GGGTAGGTAGGGCGGGATTTTTAGGAGGATCGGTA GAGGCGCGTATAGGTGCGTGGTGT |
| 15 | C13orf18_Gron | 80183 | C13orf18 | NM_025113 | TTTTTAGGGAAGTAAAGCGTCGTTTTCGTCGTAGGT ATCGAGACGTCGTTTAGATGGAAGAAATTTTGGAGA TGCGCGTTTTTATATCGGTGTCGCGGCGTTCGGGTT TAGTATTACGT |
| 16 | C16orf48_22922 | 84080 | C16orf48 | NM_032140 | TAGTTTGGTAGTTAGCGGGTCGGGGCGTTTAGTTTT ATTTTTTAGAGCGTTGCGGTTTTGTGTTTGAAGGTTA AATAGTTTGACGGTATTTCGGAGGTTT |
| 17 | C9orf19_19865 | 152007 | C9orf19 | NM_022343 | ATAGGGGGAGTTCGGTACGGCGCGGGCGTTTAGGA GAGAAGGAATAATAAATGGATGAGGGGGATGTTTAG GGTTGTTTTCGGGATAGTCGAGCGGGGTAAATTGT |
| 18 | CALCA_2 | 796 | CALCA | NM_001033952 NM_001033953 NM_001741 | CGTTTTTATAGGGTTTTGGTTGGACGTCGTCGTCGT CGTTGTTATCGTTTTTGATTTAAGTTATTTTTCGTTAG GTGAGTTTCGAGATTT |
| 19 | CAMK4_27356 | 814 | CAMK4 | NM_001744 | TAGTTGTATCGGTTTAGGCGTTTTGGTGGGGTGGGA AGGATTCGAGTCGTATTTGAATGAAGGTTAGTTTTTT TTAAGATATTAATTAGGTAGGGAGAAATCGAAGGG TACGAAGGTAG |
| 20 | CCNA1_gron | 8900 | CCNA1 | NM_003914 | GTTATGGCGATGCGGTTTCGGAGAGCGTACGTTTGT CGCGGTCGGTATGGAAACGTTTTCGTTAGGTTCGG GGCGTCGTTGATTGGTCGATTTAATAGACGCGGGT GGGTAGTTTAGTCGTATCGTTAAGTTCGGTCGTTTTT TAGGTTGG |
| 21 | CCND2_25209 | 894 | CCND2 | NM_001759 | GAAGGTAGCGTTTTCGATGGTGAGTAGGTTTTGTA GGACGCGGTCGTTTCGGAGTAGGTTGCGGTTTCGT ACGGTTTTGCGGATCGGGTTATTT |
| 22 | CDH1_17968 | 999 | CDH1 | NM_004360 | AATTTTAGGTTAGAGGGTTATCGCGTTTATGCGAGG TCGGGTGGGCGGGTCGTTAGTTTCGTTTTGGGGAG GGGTTCGCGTTGTTGATTGGT |

TABLE 2-continued

Amplicon details (converted sequences issuing from the methylated version of the DNA)

| Row Nr | Assay Name | Official Gene ID | Gene Symbol | Refseq | Amplicon Sequence (converted) (5'-3') SEQ ID NO's 265-396 |
|---|---|---|---|---|---|
| 23 | CDH1_23527 | 999 | CDH1 | NM_004360 | GAGGGGGTAGGAAAGTCGCGTTCGTTTTTATTATT TATTTTTATTTTTATTATTGGGGGGTTCGGAGCGCG CGAGGTTTTTAGGTCGTTTCG |
| 24 | CDH4_24735 | 1002 | CDH4 | NM_001794 | GGGACGATTTTCGTTGTTCGGGGTTTTCGAACGGC GGGGGCGGGAGGCGGTAATTTATTCGGAGCGCGTC GGAGAGCGAGAGTAGTAGAA |
| 25 | CDK6_9703 | 1021 | CDK6 | NM_001259 | AATTTCGTTTGTAGAGTCGTCGTCGTCGTCGTCGTC GGAGGAGCGAGTCGATTTTTTTTTTTTTTTTTTCGAA GCGAAGTTTTTAATATAGA |
| 26 | CDKN1B_23172 | 1027 | CDKN1B | NM_004064 | GTCGGTAAGGTTTGGAGAGCGGTTGGGTTCGCGGG ATTCGCGGGTTTGTATTCGTTTAGATTCGGACGGGT TTTGTTATTTT |
| 27 | CDKN2B_27345 | 1030 | CDKN2B | NM_004936 | TTAGAAGTAATTTAGGCGCGTTCGTTGGTTTTTGAG CGTTAGGAAAAGTTCGGAGTTAACGATCGGTCGTTC GGTTATTGTACGGGGTTT |
| 28 | CDO1_55928 | 1036 | CDO1 | NM_001801 | AATTTGATTTGTGTGTATCGCGTTTTTAGCGATTT CGGATTTATTCGTTGTTAGGGGTTTGGGGGTGGGT TTTTTGTTTTTTGCGACGATATTTTTACGTTTC |
| 29 | CDO1_55929 | 1036 | CDO1 | NM_001801 | GTTTACGCGATTTTTGGGACGTCGGAGATAACGGG GTTTTTGGGAAGGCGCGGAGTTCGGGGAAGTCGGG GATGTGCGCGTGAGTCGTGTTCGTAGGGTTTT |
| 30 | CLSTN2_19850 | 64084 | CLSTN2 | NM_022131 | AGGGTTTTTCGGAGTCGTTTATTAGGGTTTTTGGG GGTTCGGTTTCGATTGGGTAGGGGGATTTGGATAG GGTTTCGGAGCGTGGAGACGGTTGAGGAA |
| 31 | CLU_13810 | 1191 | CLU | NM_001831, NM_203339 | AGGCGTCGTATTTATAGCGTTTTGTTCGCGTATATAT TTTTTTGGGGTTGGTTGTAAATTTGTATGATTTACG TTTAAAGAATGTCGCGGAAAGTAAGGGGA |
| 32 | CLU_19838 | 1191 | CLU | NM_001831, NM_203339 | GTGGGGGTCGGTGTAGTATCGGGTTGGGGGCGTC GGGGGGCGTATTATTATTACGAATAGTTGTGTTGGT TTTAGGAGAGATTTTGAGGTGCGGTCGTTCGGCGTT TTTAGTAGGGA |
| 33 | COL1A1_23253 | 1277 | COL1A1 | NM_000088 | TATAAAAGGGGTTCGGGTTAGTCGTCGGAGTAGAC GGGAGTTTTTTTTCGGGGTCGGAGTAGGAGGTACG CGGAGTGTGAGGTTACGTATGAGCGGACGTTAATTT |
| 34 | CPT1C_23912 | 126129 | CPT1C | NM_152359 | AGGAAGTATTTATTGCGTATGTTTCGTAGTTTGGGAT GTTGAGGTTGTGAGCGGAGGCGAGCGTCGAGGATA AGTGATGG |
| 35 | CTDSPL_23795 | 10217 | CTDSPL | NM_001008392 | TAATTTTAAGGAGGACGAGGGTCGGTTGTCGGGCG CGGGCGAGAAAGGTGAGGAGGGGCGTAGGCGGTC GCGGGTTGGGGGCGAGCGTATATTTCGCGTCGTTG GAGTTTAT |
| 36 | CTDSPL_23804 | 10217 | CTDSPL | NM_005808 | GTTTTGGGAGAGGCGGTTCGGGTTCGCGTTTTAGTT TTCGTCGTCGTCGTCGTTGGGTTCGAGCGGTCGTC GTTTCGTTATTATGA |
| 37 | CYCLIND2_1 (official full gene name for CCND2) | 894 | CCND2 | NM_001759 | GGTGTAGCGTTTAGGGTCGTCGTAGGTCGGGGGTA GGGTTTTAGCGGTTTTTTCGCGGTTAGCGGTTACG TAGGAAAAATTCG |
| 38 | DAPK1 | 1612 | DAPK1 | NM_004938 | GGATAGTCGGATCGAGTTAACGTCGGGGATTTTGTT TTTTCGCGGAGGGGATTCGGTAATTCGTAGCGGTA GGGTTTGGGGTCGGCGTTTGGGAGGG |
| 39 | DBC1_23879 | 1620 | DBC1 | NM_014618 | AGGATAGGTATGAATTTCGGTTTCGGAAGGCGGTTA TTATTTTTTTTGTTTTCGGTTTTTTCGTTTTTCGTTTC GTTGTTGTTCGTTCGTTT |
| 40 | DDX19B_22963 | 11269 | DDX19B | NM_007242, NM_001014449, NM_001015047 | CGGGTTTGAGGGTAATAGAATCGTAGATTTTAAGTG GGTAAAGGGTGGTTAAATAGGAGTGGTTTTCGACGT TATTGTGGCG |

TABLE 2-continued

Amplicon details (converted sequences issuing from the methylated version of the DNA)

| Row Nr | Assay Name | Gene ID | Official Gene Symbol | Refseq | Amplicon Sequence (converted) (5'-3') SEQ ID NO's 265-396 |
|---|---|---|---|---|---|
| 41 | DKK2_23970 | 27123 | DKK2 | NM_014421 | GTGCGGGGTAAGAAGGAACGGAAGCGGTGCGATTT ATAGGGTTGGGTTTTTTGTATTTTGGGTTACGTTTT TTTGGCGAGAAAGCGTTTCGTATTTGATTGTTTTT |
| 42 | DKK2_23973 | 27123 | DKK2 | NM_014421 | GAGAGAGAAAGCGGGAGTTCGCGGCGAGCGTAGC GTAAGTTCGTTTTTTAGGTATCGTTGCGTTGGTAGC GATTCGTTGTTTTTTGTGAGTTAGGGGATAACGTTTC GGGGTAATTGTGA |
| 43 | EGFR_23302 | 1956 | EGFR | NM_201283, NM_005228 | TAGGAGCGTTGTTTCGGTCGTTTCGGAGGGTCGTAT CGTTGTTTTTCGAAGAGTTCGTTTCGGTTTTTTCGAT TAATATTGGACGGAGTTAGGGGGTCGTG |
| 44 | EGR4_24277 | 1961 | EGR4 | NM_001965 | TTTAGGTGGGAAGCGTATTTATCGGACGGTCGGTTC GGTGAGGCGTAGCGTTTTAGATTGGCGTATTCGCG GTTTTAGCGTTT |
| 45 | EPB41L3_19071 | 23136 | EPB41L3 | NM_012307 | GGGATAGTGGGGTTGACGCGTGGTTTCGGCGTCGC GCGGTTTTTCGAATTTCGAGTTTCGCGTTCGGCGCG GTCGGGGTTTTAATCGTTTTTTCGTTCGTCGGGATT TTTAT |
| 46 | EPB41L3_19072 | 23136 | EPB41L3 | NM_012307 | GCGTGGGTTTTCGTCGTAGTTTCGCGGAGTTTCGGT GTTTTTTGTAATAGGGGGCGGGGGGAATAGCGGCG AGTAGTTTTGGG |
| 47 | FOS_22338 | 2353 | FOS | NM_005252 | CGGGTTGTAGTTAATATCGAGGGTGTAGTGCGGGG GGAGGCGGGGTCGCGGTTGGGGGAGGGGAGGC GGGAACGGCGTAGAATGAGAGAG |
| 48 | FOXE1_13314 | 2304 | FOXE1 | NM_004473 | TTTGTTCGTTTTCGATTGTTCGTTTTCGGGGTTCG GCGTATTTTTTAGGTAGGAGTAGTTGTGGCGGCG CGGTAGGAGTTTTATAGCGTTA |
| 49 | GADD45A_24463 | 1647 | GADD45A | NM_001924 | CGTTAATCGGATAAGAGTGCGCGCGGGATTCGTTTT TTTTTTTCGGTATCGTTTTCGTTTTCGTTTTTTCGGTT CGTTTTTCGCGTGGTTTT |
| 50 | GATA4 | 2626 | GATA4 | NM_002052 | GTATAGTTTCGTAGTTTGCGTTTAGCGGAGGTGTAG TCGGGGTCGCGTATTTTCGTTTCGTTTTTGTACGTG ATTTTTATAGGTTAGTTAGCGTTTTAGGGTCGAGTTG TTGGGTCGGGGATTCGAGTCGCGAGTT |
| 51 | GATA4_13295 | 2626 | GATA4 | NM_002052 | GGTATTGTTATTTTGCGTTTTCGGAGTCGTTGGTGG GCGATAAGTTTTCGTTTATTTTTTTTATGTGCGAGTT GTCGTGTAGTTTGTTTCGGG |
| 52 | GDAP1L1_19773 | 78997 | GDAP1L1 | NM_024034 | GATTTCGGGTTGTTATGGCGATTTTTAATAATTTGAT TTTTATTAATTGTAGTTGGTGGTTTATTTTCGCGTTG GAGAGCGATGCGGTTAAGTTAG |
| 53 | GDAP1L1_19775 | 78997 | GDAP1L1 | NM_024034 | GAAAGAAGGAGGTTTCGGCGCGGCGGTTTTTTTTCG TTTAGTATTATATGGTTTCGTCGAGTTTGTTTTTTTT TTTTTTTTTTTCGTTTCGTGAATGTTATTATTTATCG GG |
| 54 | GNB4 | 59345 | GNB4 | NM_021629 | GTTGTGAGTTGCGTTTTTTACGTCGGTTTCGCGTTTT AGGGGTTGTTGAGCGTTTAGCGGATATCGGTAGCG |
| 55 | GPNMB_52607 | 10457 | GPNMB | NM_001005340 | GGTCGTAGTCGTAGTCGGGAGATTGAGGGTTAGGG CGCGGTCGCGGGGTTTTTGGGTCGGGGCGCGGTT TACGTTTTAGGTTTTTGCGG |
| 56 | GREM1_29777 | 26585 | GREM1 | NM_013372 | GAATTTGGTACGATTTTACGGAGATTTCGTTTTTTTT AGCGTAGTTTTCGTTATTGAGCGCGGGATTAACGTA GGCGATGTCGGGCGGTCGATAGGGAAAGTTTAGAT |
| 57 | Gst-Pi_New3 | 2950 | GSTP1 | NM_000852 | ATTTAGTATTGGGGCGGAGCGGGGCGGGATTATTTT TATAAGGTTCGGAGGTCGCGAGGTTTTCGTTGGAGT TTCGTCGTCGTAGTTTTCGTTA |

TABLE 2-continued

Amplicon details (converted sequences issuing from the methylated version of the DNA)

| Row Nr | Assay Name | Gene ID | Official Gene Symbol | Refseq | Amplicon Sequence (converted) (5'-3') SEQ ID NO's 265-396 |
|---|---|---|---|---|---|
| 58 | HHIP_23319 | 64399 | HHIP | NM_022475 | AGTAGTAGGAATAGAAACGGCGACGGCGGCG GGGTAGGCGGAGGTAGGGTTAGCGTTGGGTTTTAG ATGATGTTGAGGTTTTTTTGTCGGCGGTTGTAGTTTT |
| 59 | HIN1_3 | 92304 | SCGB3A1 | NM_052863 | GAAGTTGGTTAGGGTACGGTCGTGAGCGGAGCGGG TAGGGTTTTTTTAGGAGCGCGGGCGAGGTCGGCGT TGGAGGGGCGAGGATCGGGTATAAGAAGTT |
| 60 | HOOK2_19741 | 29911 | HOOK2 | NM_013312 | GGATCGTTGGATTTTGGTTCGAGTATTCGTTTTCGTT ACGTGGTAAGTTTGCGTGGAAAGGATAGGTGAGGTT TCGTTTTTTTGTGGTTGGTTTACGTGGGGCGAGGAT ATA |
| 61 | HOXA1_27316 | 3198 | HOXA1 | NM_153620 | TTTTTAGAGTAAATAGCGGGAGCGTATTGGGGGTAT TTATTATTTACGTTGTTTTTTGATTAACGCGTAGG GGTTGTAAGGCGTAT |
| 62 | HOXA11_23844 | 3207 | HOXA11 | NM_005523 | TTTTATTTATTCGGGGAGTTGCGGGTGGGAGGTGG GGACGAGAGTTGAGTTTTATCGTTTTTTGTATATTC GAGAACGAGGATTTTGT |
| 63 | HOXA7_2 | 3204 | HOXA7 | NM_006896 | TCGTAGGGTTCGTAGTCGTTTAGAATGGAAGGGTAA GAGGTTTAAATATGCGGTTAAAGAATTCGTTCGCGT TCGGCGGGTTTGGCGCGTTTCGCGGAAAAAGATTT GGA |
| 64 | HOXD1(2) | 3231 | HOXD1 | NM_024501 | GTCGGTTGACGTTTTGAGATAAGTCGGAAAAGGGTC GGGTTCGTCGAAGGTCGCGTAATTTATTTGGTCGTT GAGGAGGAAAGAGTCGTCGTTCGAGAAGACGGT |
| 65 | IGSF4_18987 | 23705 | CADM1 | NM_014333 | TCGGATTTCGTTTTAGCGTATGTTATTAGTATTTTAT TAGTTGTTCGTTCGGGTTTCGGAGGTAGTTAACGTC GTTAGTTTGAGGTAGGTGTTC |
| 66 | ISYNA1_19726 | 51477 | ISYNA1 | NM_016368 | TAGGTTGGTTTGGTTTCGGTCGTTTAGAGTTTTCGTT GATTTTTGTTTATTTCGGGTTTTTAGTTCGTCGCGA TGGAGGTCGTCGTTTA |
| 67 | JAM3 | 83700 | JAM3 | NM_032801 | GGGATTATAAGTCGCGTCGCGTTGTCGTTGGTTTTT TAGTAATTTTCGATATGGCGTTGAGGCGGTTATCGC GATTTCGGTTTTGCGTTCG |
| 68 | JPH3_12611 | 57338 | JPH3 | NM_020655 | TTAGATTTCGTAAACGGTGAAAACGGATTTAGGCGA TCGATATAGTAGAGTCGCGGTCGTCGGCGGTTTTG GGTCGCGAGCGTTTTTCGGAGGAGA |
| 69 | KNDC1_19691 | 85442 | KNDC1 | NM_033404 NM_152643 | TGGATGGAGTTTAGGTTATATCGTCGAGTTGTTTGT GCGTGTTATTTTGGAAGTTATTCGTGTGTTAATTA TGTAGGGCGGTTTCGTAGTATTTT |
| 70 | KRAS_24235 | 3845 | KRAS | NM_033360 | AGGAGGGATTGTCGGATTTACGCGGCGGTTCGTTTT TGTTTAGTCGTAAGGTTGTTTTCGTAGTCGTTAATT TTGATTCGGAGC |
| 71 | LAMA1_63431 | 284217 | LAMA1 | NM_005559 | TTTTTAGATTTATCGAGTGGCGGCGGAGGCGAGATG CGCGGGGCGTGTTTTTGGTTTTGTTGTTGTGTGTC GTCGCGTAGTGTCGGTAGAGAGGTGAGTTCG |
| 72 | LMX1A_9513 | 4009 | LMX1A | NM_177398, NM_177399, NM_001033507 | CGGTATCGTTGTTTAGGAGGCGTCGATATTTCGTA AAGGTTTAGTCGGGGTGAGGGGTATTGGGGGGCGA TCGGGTTAGAGCGTTTCGAGGTAATAGTTATACG |
| 73 | LOC285016_22940 | 285016 | hCG_1990170 | NM_001002919 | AGTTGTTTGGTATTCGCGGTTTTTAAAGGGGAAAGA AAGTTGCGTTCGCGTTAGGCGTAGCGCGTTCGGCG GACGCGGTTTTTCGGGCGAAAGTTAGGAGGGGTCG |
| 74 | LOX_23395 | 4015 | LOX | NM_002317 | GTTAGATTGATTCGTTCGAGGAGGACGTGGTTTAT AGAAAATAAAAACGGGGTTTAAATTACGTGAGGGAA GGAGAAATTTTTAATTAAGGAGGCGAGCGGAGTACG GGTATTTTAGTT |

TABLE 2-continued

Amplicon details (converted sequences issuing from the methylated version of the DNA)

| Row Nr | Assay Name | Gene ID | Official Gene Symbol | Refseq | Amplicon Sequence (converted) (5'-3') SEQ ID NO's 265-396 |
|---|---|---|---|---|---|
| 75 | LTB4R_31250 | 1241 | LTB4R | NM_181657 | TAGTAGATTTTTAGCGGTGAAGACGTAGAGTATCGG GTTGACGTTAGAATTGAAGAAGGTTAAGGTCGTAGT TTTCGTTCGCGTCGTTTGGTCGGTTTCGTTTAGTTTC GTTAAGGTTTT |
| 76 | MAL | 4118 | MAL | NM_002371 | TTCGGGTTTTTTGTTTTAATTCGCGCGCGGGGGC GTTTAGGTTATTGGGTTTCGCGGAGTTAGCGAGAGG TTTCGCGGAGTTTGAGCGGCGTTCGTTTCGTTTTA AGGTCGACGTTAGTACGTCGTTATGGTTTTC |
| 77 | MTAP_24628 | 4507 | MTAP | NM_002451 | GTAAGTGAGTTTCGAGTGTCGCGTTTTAGTTTTTTTT CGCGGCGGTAAGGGACGTACGGGTCGGGCGTATG GTTTTCGGAG |
| 78 | MYO18B_24620 | 84700 | MYO18B | NM_032608 | GAAAGGTCGGATTTGTTTTTCGAGGGTCGAGTTAGT TTTTGTAGATGGTTGTAGTTTTAGTTATGAGTGTTAT TTTTTTTTGTTTTTATAGGGCGAGGCGTGATGAGAT GGT |
| 79 | NDRG2_56603 | 57447 | NDRG2 | NM_201540, NM_201539, NM_201535, NM_201537 | AGATTTTGTGGTTTCGTCGTTAATTTTTTTTAGTTCG GTTTAGAATAGGAGATTAGTTTAGGTTCGTTGAATCG TAATGTTCGGGGGAT |
| 80 | NID2_9091 | 22795 | NID2 | NM_007361 | GCGGTTTTTAAGGAGTTTTATTTTCGGGATTAAATGG TTCGTAAGGTTTGGGGTAGCGGCGTTGTAGGAGAT GAGTTTAGCGTAAAGGGAATTTCGTAG |
| 81 | NOL4_19645 | 8715 | NOL4 | NM_003787 | GAGAGATTCGGGATTCGTGTGTTTTTCGGGGTTTAA AGGCGTTGGGCGGCGGTTGTTTTCGGGAGAGGC GTAGTTTTTATTTTTGGATTAC |
| 82 | NPTX1_2 | 4884 | NPTX1 | NM_002522 | AGTACGTTGTTTCGGAGTTTTTCGGCGTCGTCGGCG GTTACGGACGCGGCGTATATGTCGGCGTTTACGGG TATCGAGGTGTAGATGAAG |
| 83 | NPTX2_57779 | 4885 | NPTX2 | NM_002523 | GCGTCGTTTTGTATGGGTATCGCGGGTAGCGGGTA GTCGGCGTGTATCGTTTTTGGGGGTAGTGTCGTGTA TACGAAGCGGTTATCGGG |
| 84 | OGFOD2_23131 | 79676 | OGFOD2 | NM_024623 | CGAGTAGTAGTTGCGTCGGGATTACGGTTCGGTGA GTGGTCGTTGTCGTTTTTACGGAGTAGTGGGTAGAG AGGGGTAGTGGAGGAGGGAAGTTCGTTTTTAGGGT CGTTTGT |
| 85 | PAK3_1 | 5063 | PAK3 | NM_002578 | TGTATGATTTTAGTTCGCGGATAAGTGGGTGTGTTA GGGTCGTTTTTAGAGGGTCGGGGTTTTTTCGTTTGG TTAAATTTTAGATTCGTTTATTGGGGTTTGGGTCGTT TGAGGTAAAATTCGT |
| 86 | PAK3_3 | 5063 | PAK3 | NM_002578 | GCGGATTTATTTGTTACGGATTTAGTTATTTCGTTA AGATTTTTTTTTATTTTCGAGCGTTTTAGTTGGCGG GGTTGGGGAGTCGTAGTTTCGCGGTCGTAGTCGTA GTTTCGGGTT |
| 87 | PAX1_27210 | 5075 | PAX1 | NM_006192 | ATTGCGTCGGGTTTAGTTTCGGTTATTTCGGTTATTT CGGCGTTAGGTAGTGGTCGGTTCGTTCGTTATGGG TAAGGGGC |
| 88 | PAX1_27211 | 5075 | PAX1 | NM_006192 | GTTTAGGGAAAGCGGACGAGAGGGAAGGGAGGTA GGCGGATTCGATTTATTTTATTAGTTTTTTCGAGTTTT GTTTGTCGTTC |
| 89 | PDCD4_11827 | 27250 | PDCD4 | NM_145341, NM_014456 | GTTCGTAGTTCGGGGCGTTGGGAGGGCGCGGTTG GATTTGCGGGGTTATAAGAAGGTAGTCGGATTTTCG TATCGTAGGTTCGGATTTGATAGGATCGC |
| 90 | PHACTR3_11692 | 116154 | PHACTR3 | NM_080672 NM_183244 NM_183246 | TTATTTTGCGAGCGGTTTCGCGATACGAGGTAGTCG TTTTCGTTTTTCGACGCGGTTATGGGTTCGGTTCGGC GCGGGGGTAAGTTAGAGCGAGTCGCGTGGAATTAG AGTATTC |

TABLE 2-continued

Amplicon details (converted sequences issuing from the methylated version of the DNA)

| Row Nr | Assay Name | Official Gene ID | Gene Symbol | Refseq | Amplicon Sequence (converted) (5'-3') SEQ ID NO's 265-396 |
|---|---|---|---|---|---|
| 91 | POMC | 5443 | POMC | NM_000939 | GATTTGGGCGTTTTGGTTTTTCGCGGTTTCGAGTTTT TCGATAAATTTTTTGCGTCGATTGCGGTATGAGAAGTC |
| 92 | PRKCE_24134 | 5581 | PRKCE | NM_005400 | GTGGGTTTTAAGTTTACGGTTTCGTAGATTTTGATTT TAAGAAGGTTATTGAATATTATTATGGTCGGGGCGG GGAGTGGGGTCGGGGTTATTTCGTTTGTTTCGAG GGTAGG |
| 93 | RAD23B_1 | 5887 | RAD23B | NM_002874 | GGCGGAGTTTGTATAGAGGCGGAGTCGCGGTAGTC GGAGAGAACGTTTTAGTAATAGTCGTTAGGAGGAAG TTTTAGGAGTTTTTGTCGTTTACGGAACGCGTTTGC GTAATTCGGGTT |
| 94 | RALY_19607 | 22913 | RALY | NM_007367 | TTTTTGGGTTTCGTTGTTTCGAGTTGGCGTCGTTCG CGCGTTTCGTCGTATTGATAGCGGCGCGAGTTTCGT AATCGCGAGTTTTGTTTTCGGTCGGTATTATTGAGG CG |
| 95 | RARA_24121 | 5914 | RARA | NM_001024809 | TTCGTTTCGTTTAGGTATCGTTTTTGGTTTAATTTATT TTCGGCGCGTTCGGTTGTAGCGGGAGAAACGTAGG GAATCGAGAGG |
| 96 | RARA_24129 | 5914 | RARA | NM_000964, NM_001033603 | TTTAGGATTATAGTGAGCGACGGGAGAGGAGGGAT GGGGAAAGTTAGAATTGGCGAGAAGGAAATGGTTA GATTAGAAGTAGAGGTCGGGGTTAAAGGCGGTTA |
| 97 | RASSF1A | 11186 | RASSF1 | NM_007182 NM_170712 NM_170714 | GCGTTGAAGTCGGGGTTCGTTTTGTGGTTTCGTTCG GTTCGCGTTTGTTAGCGTTTAAAGTTAGCGAAGTAC GGG |
| 98 | RBP4_24106 | 5950 | RBP4 | NM_006744 | GGTCGTTTCGTTGTTTTATAGCGTCGGGGGGAGGG GGTCGCGTTTTCGTAATCGCGCGGGGTGAAAGATC GAAGGGGAGGCGTCGGGGGTATTTGTATAACGC |
| 99 | RECK_18940 | 8434 | RECK | NM_021111 | TTACGGTTAGTAGAAGGAGTAGCGTATTTCGTAGAG AGGTTCGGACGGTCGTTATGTTCGGGTCGGCGGT TTTAGAGTCGCGGGATGTTCGGATTTAGTTTGGTCG TAG |
| 100 | RPRM_2 | 56475 | RPRM | NM_019845 | TCGAGGAAGAAGATGTCGAAGATTACGGTGAGTGA GAGTACGTATATGATCGCGATTTGTATTACGCGTATT ATGTATAGGTTACGTTCGTTCGGGTTTTT |
| 101 | SALL4_12833 | 57167 | SALL4 | NM_020436 | GAGGCGTAAGTAGGCGAAATTTTAGTATATTAATTC GGAGGAGGATTAGGGCGAGTAGTAGTCGTAGTAGT AGATTTCGGAGTTTGTAGATGCG |
| 102 | SEMA3F_23485 | 6405 | SEMA3F | NM_004186 | GATTAGAGCGAGCGAACGAATCGCGGCGGTTCGGA GAGTTTCGAGCGTAGCGTAGGATTTGGGTACGTCG CGAGGAATCGTGTAGTTTAGCGCGGTCGTTCGGTTC GGGTTTAGTAGTTA |
| 103 | SLC5A8_24598 | 160728 | SLC5A8 | NM_145913 | GGTTTGTTGGTCGTTTTTAGCGAAGGCGTAGTAGAT GTCGATGGCGGTCGAGATGATTAGTATGTTCGCGAA TATTACGTAGTTTTATATTACGAAGGTGTCGATGTTT CG |
| 104 | SLC5A8_24601 | 160728 | SLC5A8 | NM_145913 | GTATTTAGGGTAGCGGGTCGATTTTTCGAGGTTTTA TATTTGGTTTGAGGGGCGCGGTTCGTAGCGGCGG GTGTAGGGGCGATTGTTAGTTTTTATTTCG |
| 105 | SLIT1_23651 | 6585 | SLIT1 | NM_003061 | GCGTTATGGTGTTTTTATAGCGTTTCGTTCGCGGAGTT AGACGGTAGTAGTCGTTGATTATTTTCGTTCGGGGT CGTTTTTAGGTGTAGTTTCGGGGTAGAGTTATCGAA GA |
| 106 | SLIT1_23653 | 6585 | SLIT1 | NM_003061 | TTGTAGGCGGTTTGTAGTCGTTGAGTGGTCGTCGG GAGAGGGGGGTTGCGGCGGGGAGGGCGGGGAG GAGTTTGGTTTTGGATGTGTGTTTTTCGATTGATGGA TGATTGTC |

TABLE 2-continued

Amplicon details (converted sequences issuing from the methylated version of the DNA)

| Row Nr | Assay Name | Gene ID | Official Gene Symbol | Refseq | Amplicon Sequence (converted) (5'-3') SEQ ID NO's 265-396 |
|---|---|---|---|---|---|
| 107 | SLIT2_23672 | 9353 | SLIT2 | NM_004787 | GAGGATCGGTTTAGGTTGCGGCGGAGTCGAGGGCG AGGGAGAGGTCGCGTGAGTGAGTAGAGTTTAGAGT CGTGCGTTTTTAGAATTG |
| 108 | SLIT2_23676 | 9353 | SLIT2 | NM_004787 | AGGGGAAGACGAAGAGCGTATATTTATAGTTTTTCG GTGTTGCGGGGGATATTTTTGGGTACGTTGCGTAGC GTTAGTTCGTG |
| 109 | SLIT2_23681 | 9353 | SLIT2 | NM_004787 | TAGCGGAGAGGAGATTACGCGTTTTTTGTTTTTTAAG GATGAATTTGGCGGTAAAAGAGTTGGGGTTTTTAAC GGTTGTTAAGATGTAGGGGTC |
| 110 | SLIT3_23619 | 6586 | SLIT3 | NM_003062 | AGGGGTATTTATAGGCGTTTAGCGTTGCGGGGAT GTTTCGAGGAATCGCGCGGAGGTTTAGTTCGTGGTA GTTTACGTTGGTAGCGGAGTAGGTA |
| 111 | SMPD1_24061 | 6609 | SMPD1 | NM_000543 | GAAGGGTAATCGGGTGTTTTCGGCGTCGTTCGGGG TTTTGAGGGTTGGTTAGGGTTTAGGTCGGGGGGGA CGGGATAGACGAATTAG |
| 112 | SOCS1_23595 | 8651 | SOCS1 | NM_003745 | GATAGGGTTTTGTTTTCGGCGGGTGTGGAGATAGTT GGGGCGGAGGAGGGTGTGTTAGGGCGCGTTTTAAG AGGGTTTGGCGGTAGAAAGTGGAATTCGAGGTAGC GGGGTAAAAT |
| 113 | SOX1_27153 | 6656 | SOX1 | NM_005986 | TTGTAGTTTTCGAGTTGGAGGTCGTTGAGGATCGAG CGTAGGAGGAAGGAGATAGCGCGTAGCGGCGGTC GGCGAGGAGATAGTATATTTCGGGTCGGGTTTAGC GTATCGTTTT |
| 114 | SOX1_27159 | 6656 | SOX1 | NM_005986 | GTTAGGAGTTCGTCGGTTAGCGAGTATTTGTTTTTTT TGAGTAGCGTTTTGGTTTTGCGGCGCGGTCGGTATT TGTAATTCGGGTG |
| 115 | SOX17_66072 | 64321 | SOX17 | NM_22454 | GAGATGTTTCGAGGGTTGCGCGGGTTTTTCGGTTCG AAGTCGTCGTTCGTGTTTTGGTTTGTCGCGGTTTGG TTTATAGCGTATTTAGGGTTTTTAGTCGGTTTAGTGA TATTGCGG |
| 116 | SPARC_Wis | 6678 | SPARC | NM_003118 | TTTCGCGGTTTTTTAGATTGTTCGGAGAGCGCGTTTT GTTTGTCGTTTGTTTGTTTGTTATTGAGGTATG |
| 117 | SPN_24052 | 6693 | SPN | NM_003123, NM_001030288 | ATCGTAGGTTGGGTTTGGTCGTTGGTAGGGAAGTG GGTAGAGGGGAGGTTCGGTTAGGTTTTTCGGTAATT TTCGCGTGTTTTGTTTTT |
| 118 | SST_23808 | 6750 | SST | NM_001048 | TGGTTGCGTTGTTTATCGTTTTGGTTTTGGGTTGTGT TATCGGCGTTTTTTCGGATTTTAGATTTCGTTAGTTT TTGTAGAAGTTTTTGGTTGTTGTCGCGGGGAAGTAG GTAA |
| 119 | TAC1_56187 | 6863 | TAC1 | NM_003182 | GGGTATTTATTGCGACGGATAGTTTCGCGGGGTGTT GAGTTTTTTGGTTTTTTCGAGCGTACGTTGGTCGTT TCGTATTTTCGGTAGTTGTCGTCGG |
| 120 | TERT_23702 | 7015 | TERT | NM_003219, NM_198255 | GGTTTCGATAGCGTAGTTGTTTCGGGCGGATTCGG GGGTTTGGGTCGCGTTTTTTCGTTCGCGCGTCGTTC GCGTTTTTAGGGTGTAG |
| 121 | TFPI-2 | 7980 | TFPI2 | NM_006528 | GTTCGTTGGGTAAGGCGTTCGAGAAAGCGTTTGGC GGGAGGAGGTGCGCGGTTTTTTGTTTTAGGCGGTT CGGGTGTTCGTTTTATG |
| 122 | TLL1_24051 | 7092 | TLL1 | NM_012464 | TAAGGAATTTTGTATTCGGAGGCGGGGAGGGCGTA GGTAAATTCGGTTTTGGCGGCGTTGGCGTTCGTAGT TTGTTAGGT |
| 123 | TNFAIP1_23212 | 7126 | TNFAIP1 | NM_021137 | GTGGTTAGCGGATTTCGAGTCGTTTTTAGTTTGTAGT CGTTTGTTTTTTAGTAGTTTTAAGTTGTGAGTTTATAT TTTCGTTCGTCGATTTCGTTCGGAGTGTTGTTTAGTT |

TABLE 2-continued

Amplicon details (converted sequences issuing from the methylated version of the DNA)

| Row Nr | Assay Name | Official Gene ID | Gene Symbol | Refseq | Amplicon Sequence (converted) (5'-3') SEQ ID NO's 265-396 |
|---|---|---|---|---|---|
| 124 | TRMT1_19794 | 55621 | TRMT1 | NM_017722 | TTTCGTAGGGTTCGGTGTCGTTTTTTATCGTTGTTGT ATTCGGTAGTTTTGGAGATTGTTATTCGAAAAATCGG GTTTTAGAGAGTATTCGG |
| 125 | TWIST1_3 | 7291 | TWIST1 | NM_000474 | GTTAGGGTTCGGGGGCGTTGTTCGTACGTTTCGGC GGGGAAGGAAATCGTTTCGCGTTCGTCGGAGGAAG GCGACGG |
| 126 | TWIST1_9329 | 7291 | TWIST1 | NM_000474 | TTTAGTTCGTTAGTTTCGTCGGTCGACGATAGTTTGA GTAATAGCGAGGAAGAGTTAGATCGGTAGTAGTCGT CGAGCGGTAAGCGCGGGGGACGTAAGCGGCGTAG TAGTA |
| 127 | UGT1A1_22912 | 54658 | UGT1A1 | NM_007120 | TTTTGTGGTTAGTCGCGGTAGGGGAATTTGGAGTTT TTTGGTTATTTTAGTAGAAGTTATCGATAGTTGATTG TTTATTTTACGT |
| 128 | WIF1_9096 | 11197 | WIF1 | NM_007191 | GCGTCGTTAGATATTTTGTTCGTTGTAGTTTTTTTA GTTAGGGTTGTTTTCGTTTAGACGGTTGGGCGCGTC GTTTTTCGGTTTGGGTGTTA |
| 129 | WIT1_24567 | 51352 | WIT1 | NM_015855 | GTATGGAGCGTTTTGCGATTGTAGGAGTACGTTAGT TTTTTAGCGTTGGTTTAGTGTCGTTTGGGTTTTCGGG TATGTGGATTCGTT |
| 130 | WT1_1 | 7490 | WT1 | NM_024426, NM_024424 | TGTGTTATATCGGTTAGTTGAGAGCGCGTGTTGGGT TGAAGAGGAGGGTGTTTTCGAGAGGGACGTTTTTTC GGATTCGTTTTTATTTTAGTTGCGAGGGCGTTTTTAA GGAGTAGCG |
| 131 | XRCC3_9322 | 7517 | XRCC3 | NM_005432 | CGTTTGTTTTTATAGGTTCGGGTAATGGAGATTCGC GGTCGTTTTCGTTTTTTGATTTTGTTTTATTTTTTACG TTCGTTGTCGTTTACGATTTTCGATTTCGTTGT |
| 132 | ZGPAT_23961 | 84619 | ZGPAT | NM_032527 NM_181484 NM_181485 | TGTATGCGGAGAGGTCGTAGTTATTGTTGTGAGTAG GATATAGTGGCGGTTGATTTGGGAGAAGTTATAGAG GGACGGGGTGGGAGAGGGACGAGGAGTCGGGAAT GGT |

TABLE 3 qMSP Molecular Beacon sequences

| Row Nr | Assay Name | Gene ID | Official Gene Symbol | Refseq | Molecular beacon sequence (5'-3') (modification beacons: 5' FAM, 3' DABCYL) SEQ ID NO's 397-425 |
|---|---|---|---|---|---|
| 1 | ALX3_25180 | 257 | ALX3 | NM_006492 | CGACATGCGCGGTTGATTCGTTTTCGGTTTGCG GGCATGTCG |
| 2 | C13orf18_Gron | 80183 | C13orf18 | NM_025113 | CGACATGCCGTCGTAGGTATCGAGACGTCGTTTA GATGGGCATGTCG |
| 3 | GATA4 | 2626 | GATA4 | NM_002052 | CGACATGCGTAGTCGGGGTCGCGTATTTTCGTTT CGGCATGTCG |
| 4 | HOXA11_23844 | 3207 | HOXA11 | NM_005523 | CGACATGCGATAAAAACTCAACTCTCGTCCCCAC CGCATGTCG |
| 5 | JAM3 | 83700 | JAM3 | NM_032801 | CGACACGATATGGCGTTGAGGCGGTTATCGTGTCG |
| 6 | JPH3_12611 | 57338 | JPH3 | NM_020655 | CGTCTGCAACCGCCGACGACCGCGACGCAGACG |

TABLE 3-continued qMSP Molecular Beacon sequences

| Row Nr | Assay Name | Gene ID | Official Gene Symbol | Refseq | Molecular beacon sequence (5'-3') (modification beacons: 5' FAM, 3' DABCYL) SEQ ID NO's 397-425 |
|---|---|---|---|---|---|
| 7 | LMX1A_9513 | 4009 | LMX1A | NM_177398, NM_177399, NM_001033507 | CGACATGCCCGATCGCCCCCCAATACCGCATGTCG |
| 8 | NOL4_19645 | 8715 | NOL4 | NM_003787 | CGACATGCGGCGTTGGGCGGGCGGTTGCATGTCG |
| 9 | PAK3_1 | 5063 | PAK3 | NM_002578 | ACATGCCGTTTTTAGAGGGTCGGGGTTTTTTCGGCATGT |
| 10 | TERT_23702 | 7015 | TERT | NM_003219, NM_198255 | CGACATGCGACCCAAACCCCCGAATCCGCGCATGTCG |
| 11 | TFPI2 | 7980 | TFPI2 | NM_006528 | CGACATGCACCGCGCACCTCCTCCCGCCAAGCATGTCG |
| 12 | TWIST1_3 | 7291 | TWIST1 | NM_000474 | CGACATGCCGGCGGGGAAGGAAATCGTTTCGCATGTCG |
| 13 | CCNA1_Gron | 8900 | CCNA1 | NM_003914 | CGACATGCACGACGCCCCCGAACCTAACGCATGTCG |
| 14 | CDO1_55929 | 1036 | CDO1 | NM_001801 | CGACATGCCCGACTTCCCCGAACTCCGCATGTCG |
| 15 | CDO1_55928 | 1036 | CDO1 | NM_001801 | CGACATGCGCGATTTCGGATTTATTGCGTTGTTAGGCATGTCG |
| 16 | GREM1_29777 | 26585 | GREM1 | NM_013372 | CGACATGCGGGATTAACGTAGGCGATGTCGGGCATGTCG |
| 17 | GPNMB_52607 | 10457 | GPNMB | NM_001005340 | CGACATGCGGTTTTTTGGGTCGGGGCGCGGCATGTCG |
| 18 | HIN1_3 | 92304 | SCGB3A1 | NM_052863 | CGACATGCAGGGTTTTTTTAGGAGCGCGGGCGAGG-GCATGTCG |
| 19 | HOXD1(2) | 3231 | HOXD1 | NM_024501 | CGACATGCGGGTCGGGTTCGTCGAAGGTCGGCATGTCG |
| 20 | LAMA1_63431 | 284217 | LAMA1 | NM_005559 | CGACATGCCAAAAACACGCCCCCGCGCATGTCG |
| 21 | LTB4R_31250 | 1241 | LTB4R | NM_181657 | CGACATGCGTAGTTTTCGTTCGCGTCGTTTGGTCGGCATGTCG |
| 22 | MAL | 4118 | MAL | NM_002371 | CGACATGCAAACGAACGCCGCTCAAACTCCGCGCGCATGTCG |
| 23 | NDRG2_56603 | 57447 | NDRG2 | NM_201540 NM_201539 NM_201535 NM_201537 | CGACATGCGTTCGGTTTAGAATAGGAGATTAGTTTAGGTTCGTTGCATGTCG |
| 24 | NID2_9091 | 22795 | NID2 | NM_007361 | CGACATGGGTTCGTAAGGTTTGGGGTAGCGGCCATGTCG |
| 25 | NPTX2_57779 | 4885 | NPTX2 | NM_002523 | CGACATGCGCGGGTAGTCGGCGTGTATCGCATGTCG |
| 26 | RASSF1A | 11186 | RASSF1 | NM_007182 NM_170712 NM_170714 | CGTCTGCGTGGTTTCGTTCGGTTCGCGTTTGTTAGGCAGACG |
| 27 | SALL4_12833 | 57167 | SALL4 | NM_020436 | CGACATGCGGAGGATTAGGGCGAGTAGTAGTCGTAGCATGTCG |
| 28 | SOX17_66072 | 64321 | SOX17 | NM_22454 | CGACATGCGTTCGTGTTTTGGTTTGTCGCGGTTTGGCATGTCG |
| 29 | TAC1_56187 | 6863 | TAC1 | NM_003182 | CGACATGCGGTTTTTTCGAGCGTACGTTGGTCGCATGTCG |

EXAMPLES

Example 1

Discovery of Methylation Markers in Cervical Cancer, Using Relaxation Ranking To identify genes that are downregulated in cervical cancer due to promoter hypermethylation and to enrich for those genes that are most frequently involved in cervical cancer, a multistep approach was used combining Affymetrix expression microarray analysis on a panel of frozen tissue samples from 39 human primary cervical cancers to identify cancer-specific down-regulated genes.

Affymetrix expression microarray analysis on a panel of 4 different cervical cancer cell lines in which the expression of (hyper)methylated genes was re-activated upon treatment with 5-aza-2'deoxycytidine (DAC) (blocking DNA methylation), and/or trichostatin A (TSA) (inhibiting histone deacetylase—HDAC).

Data from both approaches were combined, and a novel non-parametrical ranking and selection method was applied to identify and rank candidate genes. Using in silico promoter analysis we restricted the analysis to those candidate genes that carry CpG-islands. The new approach resulted in a significant enrichment of hypermethylated genes: we compared the first 3000 high-ranking candidate probes with lists of imprinted genes, X-chromosome located genes and known methylation markers. In addition, we determined the hypermethylation status of the 10 highest ranking candidate genes in both cervical cancers and normal cervices using COBRA (COmbined Bisulfite Restriction Analysis).

Material and Methods

Primary Cervical Tissue Samples:

For the expression microarray analysis, tissues from 39 early stage frozen cervical cancer samples were used from a collection of primary tumors surgically removed between 1993 and 2003 (University Medical Center Groningen, Groningen, The Netherlands). All cervical cancer patients underwent gynecological examination for staging in accordance with the International Federation of Gynecology and Obstetrics (FIGO) criteria (Finan et al., 1996). Tumor samples were collected after surgery and stored at −80° C. The stage of cervical cancer patients included 33 FIGO stage 1B (85%) and 6 FIGO stage IIA (15%). The median age of the cervical cancer patients was 46 years (IQ range 35-52 yr.).

For COBRA and BSP (Bisulfite Sequencing PCR), 10 (of the 39) primary cervical cancers and 5 controls (normal cervix) were used. The age-matched normal cervical controls were women without a history of abnormal PAP smears or any form of cancer and planned to undergo a hysterectomy for benign reasons during the same period. Normal cervices were collected after surgery and histologically confirmed.

Informed consent was obtained from all patients participating in this study.

Cervical Cancer Cell Lines:

Four cervical carcinoma cell lines were used: HeLa (cervical adenocarcinoma, HPV18), SiHa (cervical squamous cell carcinoma, HPV16), CSCC-7 (non-keratinizing large cell cervical squamous cell carcinoma, HPV16) and CC-8 (cervical adenosquamous carcinoma, HPV45). HeLa and SiHa were obtained from the American Tissue Type Collection. CSCC-7 and CC-8 (Koopman et al., 1999) were a kind gift of Prof. GJ Fleuren (Leiden University Medical Center, Leiden, The Netherlands). All cell lines were cultured in DMEM/Ham's F12 supplemented with 10% fetal calf serum.

Cell lines were treated for 3 days with low to high dose (200 nM, 1 µM or 5 µM) 5-aza-2'deoxycytidine (DAC), 200 nM DAC with 300 nM trichostatin A (TSA) after 48 hours, or left untreated. Cells were split to low density 24 hours before treatment. Every 24 hours DAC was refreshed. After 72 hours cells were collected for RNA isolation.

RNA and DNA Isolation:

From the frozen biopsies, four 10-µm-thick sections were cut and used for standard RNA and DNA isolation. After cutting, a 3-µm-thick section was stained with haematoxylin/eosin for histological examination and only tissues with >80% tumor cells were included. Macrodissection was performed to enrich for epithelial cells in all normal cervices.

For DNA isolation, cells and tissue sections were dissolved in lysis buffer and incubated overnight at 55° C. DNA was extracted using standard salt-chloroform extraction and ethanol precipitation for high molecular DNA and dissolved in 250 µl TE-4 buffer (10 mM Tris; 1 mM EDTA (pH 8.0)). For quality control, genomic DNA was amplified in a multiplex PCR containing a control gene primer set resulting in products of 100, 200, 300, 400 and 600 bp according to the BIOMED-2 protocol (van Dongen et al., 2003).

RNA was isolated with TRIzol reagent (Invitrogen, Breda, The Netherlands) according to manufacturer's protocol. RNA was treated with DNAse and purified using the RNeasy mini-kit (Qiagen, Westburg, Leusden, The Netherlands). The quality and quantity of the RNA was determined by Agilent Lab-on-Chip analysis (ServiceXS, Leiden, The Netherlands, www.serviceXS.com).

Expression Data:

Gene expression for 39 primary cancers and 20 cell line samples was performed using the Affymetrix HGU 133 Plus 2.0 array with 54,675 probes for analysis of over 47,000 human transcripts. The labeling of the RNA, the quality control, the microarray hybridization and scanning were performed by ServiceXS according to Affymetrix standards. For labeling, ten microgram of total RNA was amplified by in vitro transcription using T7 RNA polymerase.

Quality of the microarray data was checked using histograms, boxplots and a RNA degradation plot. One cell line sample was omitted because of poor quality. Using BioConductor (Gentleman et al., 2004), present (P), absent (A) or marginal (M) calls were determined with the MASS algorithm. MASS uses a non-parametric statistical test (Wilcoxon signed rank test) that assesses whether significantly more perfect matches show more hybridization signal than their corresponding mismatches to produce the detection call for each probe set (Liu et al., 2002). The relaxation ranking approach only relied on P-calls. Some samples were analyzed in duplicate, and the profile of P-calls is highly similar (93-95% of the probesets have an identical P/M/A call).

Relaxation Ranking Algorithm:

In order to identify the most promising markers that are methylated in cervical cancer, we assumed that such markers should be silenced in cancer cells and upregulated upon re-activation after DAC/TSA treatment; therefore, the best methylation markers will be genes represented by probes with:

no expression in primary cervical cancers: P-calls=0 out of 39 cancers no expression in (untreated) cervical cancer cell lines: P-calls=0 out of 4 cell lines expression in cervical cancer cell lines treated with DAC (or DAC in combination with TSA): P-calls=15 out of 15 treated cell lines To select for those gene probes that would be the best candidate hypermethylated genes in cervical cancer, we present the relaxation ranking algorithm. Probe sets were ranked, not primarily based on the number of P-calls and thus explicitly setting thresholds, but primarily driven by the number of probe sets that would be picked up, based on selection criteria (the number of P-calls in primary cancers, untreated and treated cell lines). The stricter (e.g. P-calls: 0-0-15) these selection criteria, the lower the number of probes that meet with these criteria; while if the conditions become more and more relaxed (higher number of P-calls in primary cancers and untreated cell lines, and lower number of P-calls in treated cell lines), the more probes will comply. In the end, using P-calls: 39-4-0 as criteria, all probe sets were returned. This way, there was no need to define a 'prior' threshold for the number of P-calls.

The following sorting method was applied:

(1) All possible conditions were generated and the number of probes that were picked up under these conditions was calculated:
   a. the number of samples with expression (P) of a certain probe in
      i. primary cervical cancer samples is called $x_{sample}$
      ii. cervical cancer cell lines is called $y_{sample}$
      iii. treated cervical cancer cell lines is called $z_{sample}$
   b. all combinations of x, y and z are made
      i. x (the number of P-calls in primary cancers) varies from 0 to 39
      ii. y (the number of P-calls in untreated cell lines) from 0 to 4
      iii. z (the number of P-calls in treated cell lines) from 0 to 15
      iv. In total, 3200 combinations of x, y and z can be made
   c. a probeset was found under each of these generated conditions x, y and z if:
      i. $x_{sample} \leq x$ (number of P-calls for probe in primary cancers smaller or equal compared to condition) AND
      ii. $y_{sample} \leq y$ (number of P-calls for probe in untreated cell lines smaller or equal compared to condition) AND
      iii. $z_{sample} \geq z$ (number of P-calls for probe in treated cell lines larger or equal compared to condition)
   d. under very strict conditions (x=0, y=0, z=15) no probes were found, while under the most relaxed conditions (x=39, y=4, z=0) all probes were returned. For all combinations of x, y and z, the number of probes that complied (w), was stored (2) The data was sorted with w as primary criterion (ascending), followed by x (ascending), y (ascending) and z (descending)

(3) This sorted dataset was analyzed row per row. In row i, the w, probes retrieved with criteria $x_i$ $y_i$ $z_i$ were compared with the list of probes, already picked up in rows 1 to i−1. If a probe did not occur in this list, it was added to the list (4) This process continued until there were m (user-defined) probes in the list DNA Methylation Analysis Using COBRA and Bisulphate Sequencing:

To validate the (hyper)methylated status of candidate gene probes, DNA extracted from 10 cervical cancers and 5 normal cervices were analyzed using BSP and COBRA. Bisulfite modification of genomic DNA was performed using the EZ DNA methylation kit (Zymogen, BaseClear, Leiden, The Netherlands). The 5' promoter region of the tested gene was amplified using bisulfate treated DNA. PCR primers for amplification of specific targets sequences are listed in Table 4. COBRA was performed directly on the BSP products as described by Xiong et al. (Xiong and Laird, 1997) using digestions with BstUI, Taql and/or Hinfl according the manufacture's protocol (New England Biolabs Inc., Beverly, Mass.). For sequence analysis, the BSP products were purified (Qiagen) and subjected to direct sequencing (BaseClear, Leiden, The Netherlands). Leukocyte DNA collected from anonymous healthy volunteers and in vitro CpG methylated DNA with SssI (CpG) methyltransferase (New England Biolabs Inc.) were used as negative and positive control, respectively.

TABLE 4 list of primers used for BSP ([1]: +1 is transcription start site (TSS); [2]: Several primer pairs were tested, however, none worked)

| Name | Forward primer (5'-3') | Reverse primer (5'-3') | Ta | Start position[1] | End position | RefSeq |
|---|---|---|---|---|---|---|
| DAZL | TTTGGGGGTGATGTGTGTGTTT | TCTCCCTCAACTCACCATAATA | 54 | −161 | 312 | NM_001351 |
| ADARB1[2] | | | | | | NM_015834 |
| SYCP3 | AAAATTTAAAAATTGGAAGGTATTAGG | ACCTCACTAATCAAAAACAACCTCT | 54 | −208 | +186 | NM_153694 |
| AUTS2 | TTTTAAAAGTGATAAAGTTGGTTATGG T | CCCTTTTCTTTCTCCTCTCTTTCT | 56 | +300 | −184 | NM_015570 |
| NNAT | GGTTAGGGATTGGGGAGAA | GCTAAACTTACCTACAACAACAC | 54 | −271 | 210 | NM_005386 |
| SST | GGGGTATGTGGAATTGTGTG | AAA TCT CCT TAC CTA CTT CCC C | 54 | −185 | +276 | NM_001048 |
| HTRA3 | GTYGGTTTTGTYGTTATGTAGGY | AAC TTC ACT TCC TCC CTA ACC | 57 | +190 | +622 | NM_053044 |
| ZFP42 | AGTAGGTGTTTGTTGAAGATAG | ACT CAT AAC ACA CAT AAC CAT C | 60 | +308 | +580 | NM_174900 |
| NPTX1 | GGTAGTGGGGGTTTGATAG | AAATAATCTCCTTCTACTACAACAC | 54 | −2 | +372 | NM_002522 |
| GDA | TATAGAAGGTGGAGGAAGTTGA | CACCTCCATAAAACAAATCCAAA | 54 | −239 | +194 | NM_004293 |
| CCNA1 | TATAGTTGGAGTTGGAGGGT | AAACAACTAACAAATACACTAAAA | 54 | −279 | +146 | NM_153694 |

Results

To identify novel markers that are methylated in cervical cancer, we applied a multistep approach that combines re-expression of silenced hypermethylated genes in cervical cancer cell lines (using DAC and DAC/TSA), downregulated expression in 39 cervical cancers expression, and selection of candidate markers using a relaxing ranking algorithm. The best profile of a candidate marker would be: no expression in any of the 39 cervical primary cancers and 4 untreated cancer cell lines, but re-activation of expression after demethylation and/or blocking of histone deacetylation in all 15 cell lines treated with various combinations of DAC/TSA (P-calls: 0-0-15). However, none of the probe sets showed this ideal profile. To generate a list of candidate genes, a relaxation ranking algorithm was applied.

Figure 1A:
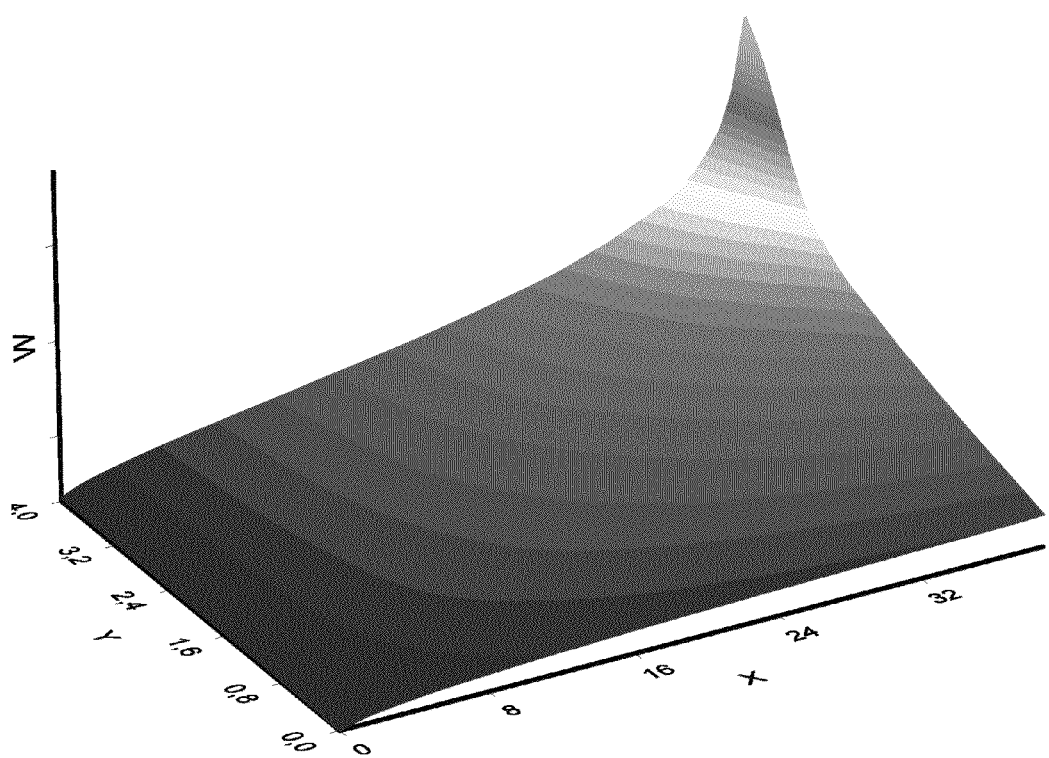
FIGS. 1A, B, and C: The number of probes (w) that is retrieved using parameters x (number of P-calls in primary cancers for probe), y (number of P-calls in untreated cell-lines for probe) and z (number of P-calls in treated cell-lines for probe).
Figure 1B:
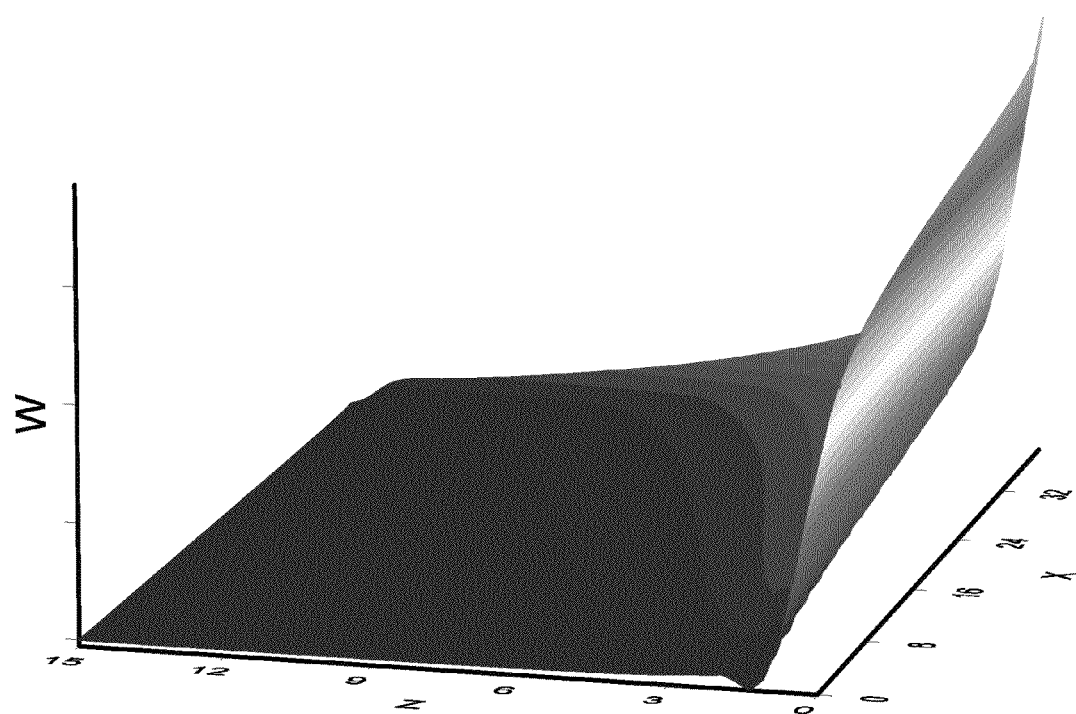
Figure 1C:
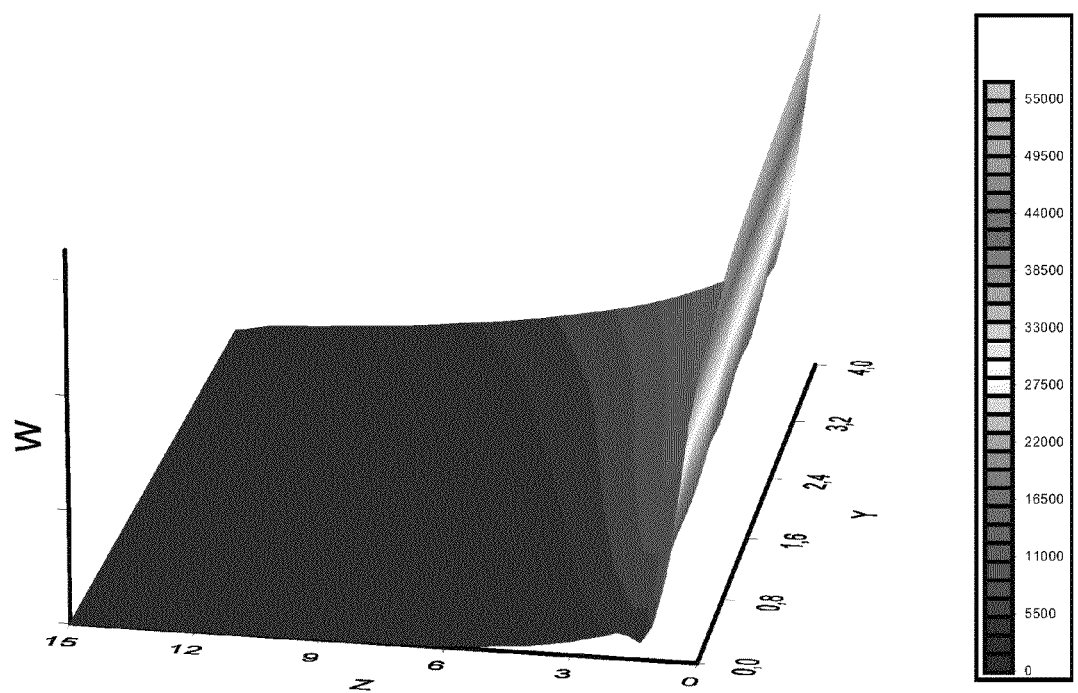

The only variable used in the relaxation ranking is the number of probes we would like to retrieve. As shown in FIG. 1, the number of probes retrieved (w) with parameters x, y and z (the number of P-calls in respectively primary tumor samples, untreated and treated cell lines) follows a complex profile which consists not only of additive elements, but also interactions between the parameters. In general, the number of P-calls in primary cancer samples (x) has the largest influence on w. The sorting methodology has the advantage that no cut-off values have to be chosen for x, y and z, and therefore there is no need to implicitly link a relative weight factor to the parameters.

Figure 2:
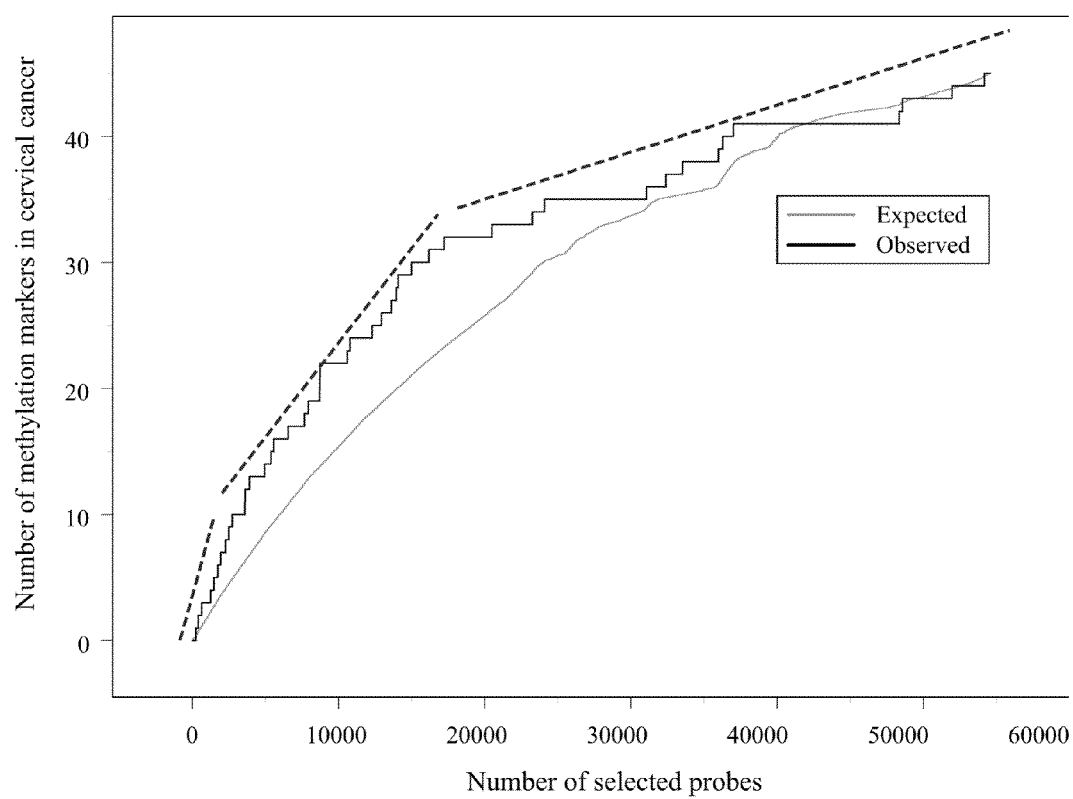
FIG. 2: Step-plot to determine optimal number of probes for further analysis. Step-plot of the number of retrieved known markers as a function of the position after relaxation ranking (this is the number of selected probes after ranking). The step plot shows the actual (observed) number of markers. If the markers were randomly distributed, one would expect the profile, marked with 'expected' (details in the text). The trend of the observed markers versus the number of selected probes is indicated with dashed lines.

To calculate the most optimal number of potentially hypermethylated candidate markers for further analysis, we estimated this number based on known (i.e. described in literature) methylation markers in cervical cancer. Forty-five known methylation markers were found using text-mining using GeneCards (Rebhan et al., 1997) for aliases/symbols to query PubMed through NCBI E-Utils. The position of the markers after ranking ("observed") was determined as shown in the step plot in FIG. 2. If the markers would be randomly distributed in the ranking, the profile would be similar to the curve, marked 'expected'. This 'expected' curve is not a straight line, but is calculated based on whether a probe could be assigned with a gene symbol and taking probes into account that are associated with a gene that is already associated with an earlier selected probe. The number of observed methylation markers has in general the same slope as expected. However, until about 3000 probes, the slope of the number observed markers versus the number of selected probes (in dashed lines) cannot be explained if the markers would be randomly distributed as its steepness is much higher. When selecting more than 3000 probes, the slope suddenly decreases to a level that is close to random distribution. This enrichment can also statistically be proven. Therefore, we selected the first 3000 probes, referred to as TOP3000, in the ranking for further analysis. In this TOP3000 list, 2135 probes are associated with a gene symbol, of which 1904 are unique.

Figure 3:
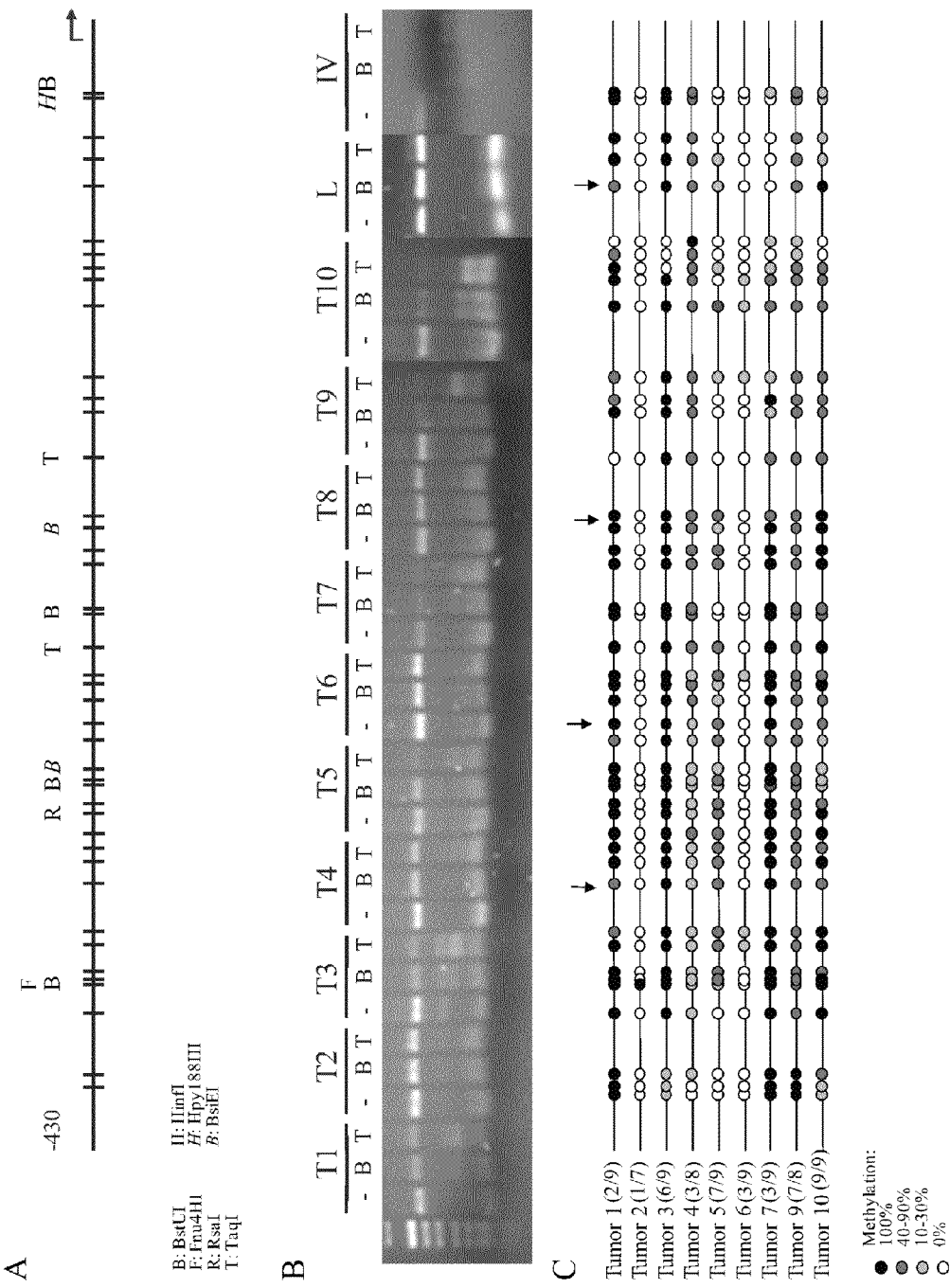
FIG. 3: (Hyper) methylation analysis of the promoter region (−430 to −5 of TSS) of the CCNA1 gene by COBRA and sequence analysis.

Validation of the 10 Highest-Ranking Candidate Genes Using COBRA:

In order to validate whether the highest ranking genes represent markers that are functionally hypermethylated in cervical cancer, we performed COBRA on bisulfite-treated DNA of 10 cervical cancers and 5 normal cervices. For this analysis we focused on those first 10 genes from the highest ranking probe-list (Table 5) that:
  represent a known gene (i.e. gene symbol)
  contain a CpG-island surrounding the TSS
  are located on any chromosome except chromosome X
  are expressed in less than 15 carcinomas BSP was used to amplify the CpG-islands of these candidate genes using bisulfite-treated DNA and COBRA to determine the methylation status. CCNA1 (at position 49) was included as a positive control for the highest listed, reported cervical cancer specific methylation gene promoter. BSP/COBRA of CCNA1 revealed that 6 of 10 carcinomas are methylated at the restriction enzyme sites (T1, T3, T5, T7, T9 and T10 in FIG. 3). Sequence analysis of the BSP-products (on average 7-9 independent clones for each carcinoma) of these 10 carcinomas revealed that in 6 carcinomas the promoter is hypermethylated in good agreement with the COBRA results (FIG. 3C).

TABLE 5

Methylation status using COBRA of the 10 highest ranking gene promoters. Gene selected for further validation after applying additional criteria. Included is CCNA1 on position 47 (original position 241) as the highest ranking cervical-cancer-associated hypermethylated gene. Methylation status was determined by BSP/COBRA (see FIG. 3 and FIG. 4).

| Rank | Gene symbol | Chromosomal location | Methylation in cancer | Methylation in normal |
|---|---|---|---|---|
| 1 | DAZL | 3p24.3 | 9/9 | 5/5 |
| 2 | ADARB1 | 21q22.3 | Nd | Nd |
| 3 | SYCP3 | 12q | 9/9 | 5/5 |
| 4 | AUTS2 | 7q11.22 | 0/9 | 0/5 |
| 5 | NNAT | 20q11.2 | 9/9 | 5/5 |
| 6 | SST | 3q28 | 7/9 | 0/5 |
| 7 | HTRA3 | 4p16.1 | 1/9 | 0/5 |
| 8 | ZFP42 | 4q35.2 | 9/9 | 5/5 |
| 9 | NPTX1 | 17q25.1 | 5/10 | 0/5 |
| 10 | GDA | 9q21.13 | 0/9 | 0/5 |
| 47 | CCNA1 | | 6/10 | 0/5 |

Table 5 summarizes the methylation status of the 10 highest ranking genes in 10 cervical cancer and 5 normal cervices using COBRA. One gene (ADARB1 at rank 2) could not be analyzed for methylation as no specific BSP products could be amplified using several combinations of primer pairs. Interestingly, using the BSP products of the other 9 listed genes, 7 (78%) showed methylation in carcinomas (Table 5). Four genes are hypermethylated in all 9 tested cancers, while for SST (7 of 9 carcinomas), HTRA3 (1 of 9 carcinomas) and NPTX1 (5 of 10 carcinomas) not all tested carcinomas are hypermethylated. FIG. 4 shows representative methylation analysis of 3 genes using COBRA. Three (NNAT, SST and NPTX1) of the 7 hypermethylated gene promoters have been reported to be methylated in tumors previously. Taken these data together, these findings showed that the relaxation ranking algorithm resulted in a very significant enrichment for genes with a positive methylation status.

A cervical-cancer-specific hypermethylated marker is only of relevance for the diagnosis of (pre-) malignant disease in case normal cervical epithelium is not methylated. COBRA analysis of 5 normal cervices for all 9 genes revealed that 4 genes (DAZL, SYCP3, ZFP42 and NNAT) are hypermethylated in all 5 samples (Table 5). On the other hand, of the 7 genes hypermethylated in cervical cancer specimens, 3 genes (SST, HTRA3 and NPTX1) did not show DNA methylation in any of the normal cervices of 5 independent individuals. We observed the same methylation profile for CCNA1 that was reported previously as a cervical cancer specific gene (Kitkumthorn et al., 2006) with hypermethylation in only 6 of 10 tumors but none of the 5 normals (Table 5; FIG. 3).

Example 2

BROAD Analysis: Genome-Wide Promoter Alignment

The "Database of Transcription Start Sites" (DBTSS) (Suzuki et al., 2004) mapped each transcript sequence on the human draft genome sequence to identify its transcriptional start site, providing more detailed information on distribution patterns of transcriptional start sites and adjacent regulatory regions. The promoters of the above identified TOP3000 genes were separately mapped on the genome-wide alignment of all promoter associated CpG islands. All the promoter sequences were subsequently aligned by clustalW algorithm (Li 2003; Thompson et al., 1994). Treeillustrator (Trooskens et al., 2005) was used to visualize the large guide tree in addition to indicating the location of the known markers. Some regions on the "circle" are denser in known markers than others, indicating that there might be a sequence mechanism located in the small region around the TSS which makes certain genes more methylation-prone. The genes were selected as candidates to be methylated if they were located in a cluster, i.e. less than 9 nodes (distance to the closest neighboring marker) away from a marker already described in the literature. These genes were assigned a score, calculated as follows: if the gene is a known literature marker, score +10, if a known marker is one node away, score +9, if there are markers two nodes away: addition to score=number of markers*8, etc. The genes were ranked according to this score.

A final gene selection was made based on the ranking, the opportunity to design primers, genes to be known as tumor suppressor genes and expert knowledge on their function, history and mutation status in other cancer types. Also known genes from literature and previous research were included for confirmation.

A final selection of markers resulting from the above set out approaches, were tested on tissue using the Base5 methylation profiling platform (Straub et al. 2007). Differential methylation of the particular genes was assessed using Base5 methylation profiling platform as follows: DNA was extracted from cervical samples, bisulfite converted, and selected regions of the particular genes were amplified using primers whose sequence represented converted or non-converted DNA sequences. Amplification was monitored in real-time set up using SYBRgreen. Data analyses designed to cope with inherent variance (i.e., noise) in measured Ct and Tm values were applied to withhold 112 different assays for detecting differential methylation of ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, Gst-Pi, HHIP, HOOK2, HOXA1, HOXA11, HOXA7, IGSF4, ISYNA1, JAM3, JPH3, KNDC1, KRAS, LMX1A, LOC285016, LOX, MTAP, MYO18B, NOL4, NPTX1, OGFOD2, PAK3, PAX1, PDCD4, PHACTR3, POMC, PRKCE, RAD23B, RALY, RARA, RBP4, RECK, RPRM, SEMA3F, SLC5A8, SLIT1, SLIT2, SLIT3, SMPD1, SOCS1, SOX1, SPARC, SPN, SST, TERT, TFPI-2, TLL1, TNFAIP1, TRMT1, TWIST1, UGT1A1, WIF1, WIT1, WT1, XRCC3, and ZGPAT in cervical cancer tissue samples.

Material and Methods

Samples:

A total of 201 frozen tissue samples (87 cervical cancer samples, the majority derived from squamous cell carcinomas; and 114 normal tissues) were collected by UMC Groningen. If the tissue contained more than 20% stromal cells, the samples were macro-dissected to enrich for tumor cells.

DNA Isolation and Bisulphite Modification:

DNA was isolated using proteinase K digestion and phenol/chloroform extraction. DNA concentration was measured using NanoDrop Spectrophotometer. From each sample, up to 2 µg of genomic DNA was converted using a bisulphite based protocol (EZ DNA Methylation Kit™, ZYMO Research, Orange, Calif.).

Detection of Hypermethylation:

Methylation specific PCR (MSP) primers were designed for each of the genes assessed for (hyper)methylation. An example on primer design spanning a large region of the promoter is provided in FIGS. 5A and 5B for ALX4.

For some genes more primer pairs were designed giving a total of 424 different assays. These assays were applied on 8 sub-arrays of 2 OpenArray™ plates by BioTrove Inc. The beta-actin assay was applied on each sub-array as an internal control. Quality control was performed using an in vitro methylated DNA sample and a negative control sample. The selectivity and the reproducibility were checked. After DNA conversion and purification, beta-actin copy number was determined by qMSP. The equivalent of 1500 beta-actin copies per sample was applied per sub-array of an OpenArray™ plate on a real-time qPCR system (BioTrove Inc.) using the DNA double strand-specific dye SYBRgreen for signal detection.

The cycling conditions were: 90° C.-10 seconds, (43° C. 18 seconds, 49° C. 60 seconds, 77° C. 22 seconds, 72° C. 70 seconds, 95° C. 28 seconds) for 40 cycles, 70° C. for 200 seconds, 45° C. for 5 seconds. A melting curve was generated in a temperature range between 45° C. and 94° C.

Analysis of Methylation:

For each combination of assays and samples two parameters were collected using an algorithm which is part of the standard data analysis package offered by the supplier. The parameters were the Ct value (threshold cycle number) of the assessed amplicon and the melting temperature of the assessed amplicon. The following data analysis workflow was applied to the results created by the software which came with the system OpenArray™ system: Data was collected for each combination of assays and samples in the two sets of samples used. Results were filtered using the following approach. Read outs from not loaded reaction spaces were removed from analysis. Technical Control assays were removed from the data set. Assays known to not work for other than biological reasons were removed from the analysis. Per sub-array, signals were only interpreted if there was a positive beta-Actin call. Ct values >0 for each gene were normalized using the Ct values collected for the gene beta-Actin. This resulted in two files containing the results for each set of sample. 201 samples were tested of which 6 gave invalid results. In total 79,170 reactions were performed of which 74,110 were valid. For the data analysis, 2 boundaries were defined: an upper bound on beta-Actin-normalized-Ct (banCt) and a lower bound on Melting Temperature (Tm). Samples below the banCt boundary and above the Tm boundary are considered to be "methylated", others (including all samples with no signal, i.e. Ct>40) are classified as "unmethylated". In both dimensions the set of candidate boundaries consists of all values in between 2 measurements, plus infinity (the equivalent of no boundary). The set of candidate models for "methylated" then consists of all combinations of candidate Tm lower bound and a banCt upperbound. A score is computed for each of these candidate models, as follows. Count: cancers inside boundaries=true positives (TP), cancers outside boundaries=false negatives (FN), normals inside boundaries=false positives (FP), normals outside boundaries=true negatives (TN). A binomial test was applied to find out how unusual it is to have at least TP successes in (TP+FP) trials where the probability of success is (TP+FN). The lower this probability value is the better. Then quality control data were taken into account to determine the most robust boundaries. Using the standard deviations (StDevQC) observed in the QC, a series of increasingly "noisy" datasets were generated. The measurements are replaced by a value randomly selected from a normal distribution with average equal to the observed measurement and standard deviation equal to StDevQC multiplied by a value that gradually (10 noise levels) increases from 0 to 2. Each time the score of the candidate model is computed by applying the 2 steps above (i.e., count and binomial test). All these scores (11 in total: 1 for "no noise" and 10 for noise levels 0.2, 0.4, . . . , 2) are added up to obtain the ultimate accumulated score. The candidate model with the best (i.e. lowest) accumulated score is retained. This same score of the best candidate model for each marker is also used for ranking the markers.

Results

A high throughput, real-time methylation specific detection platform was applied on two groups of samples isolated from cervical cancer tissue and from corresponding normal cervical tissue. In this study it was shown that a number of genes are differentially methylated in cervical cancer. We identified 112 different assays for detecting 96 different genes being differentially methylated in human cervical cancer tissue and normal cervical tissue control samples. The genes identified are ALX3, ALX4, AR, ARID4A, ATM, AURKA, B4GALT1, BMP2, BMP6, BNIP3, C13orf18, C16orf48, C9orf19, CALCA, CAMK4, CCNA1, CCND2, CDH1, CDH4, CDK6, CDKN1B, CDKN2B, CLSTN2, CLU, COL1A1, CPT1C, CTDSPL, CYCLIND2, DAPK1, DBC1, DDX19B, DKK2, EGFR, EGR4, EPB41L3, FOS, FOXE1, GADD45A, GATA4, GDAP1L1, GNB4, Gst-Pi, HHIP, HOOK2, HOXA1, HOXA11, HOXA7, IGSF4, ISYNA1, JAM3, JPH3, KNDC1, KRAS, LMX1A, LOC285016, LOX, MTAP, MYO18B, NOL4, NPTX1, OGFOD2, PAK3, PAX1, PDCD4, PHACTR3, POMC, PRKCE, RAD23B, RALY, RARA, RBP4, RECK, RPRM, SEMA3F, SLC5A8, SLIT1, SLIT2, SLIT3, SMPD1, SOCS1, SOX1, SPARC, SPN, SST, TERT, TFPI-2, TLL1, TNFAIP1, TRMT1, TWIST1, UGT1A1, WIF1, WIT1, WT1, XRCC3, and ZGPAT The resulting assays have the assay details provided in Table 1, Table 2, and FIG. 5B.

Example 3

Further Assay Selection: Base 5—Lightcycler Platform

Of the different assays listed in Table 1 previously identified using the Base5 methylation platform, the top 63 ranked assays plus β-actin (ACTB) were transferred to the Lightcycler platform in order to further fine-tune the selection of the best cervical cancer methylation markers. This platform allows the assessment of markers in a system which is closer to, and provides information valuable for the subsequent development of, a final, scaled up MSP assay. The 64 assays (Table 6) were applied on a 384 well plate by Sigma. Six repeats of the assay set fitted on a 384 well plate. The samples were randomized per plate.

The sample set selected for the Lightcycler analysis was also previously used in the Base 5 analysis in order to make a compared analysis: a total of 27 cervical tumor samples and 20 controls (frozen tissue) were collected by UMC Groningen.

TABLE 6

The 64 selected assays which were applied on the Lightcycler platform

| N° | Assays | Base 5 ranking |
|---|---|---|
| 1 | LMX1A_9513 | 1 |
| 2 | SLIT2_23681 | 2 |
| 3 | ISYNA1_19726 | 3 |
| 4 | EPB41L3_19071 | 4 |
| 5 | WT1_1 | 5 |
| 6 | DKK2_23973 | 6 |
| 7 | ALX3_25180 | 7 |
| 8 | JAM3 | 8 |
| 9 | JPH3_12611 | 9 |
| 10 | SLIT2_23672 | 10 |
| 11 | SOX1_27153 | 11 |
| 12 | SOX1_27159 | 12 |
| 13 | RALY_19607 | 13 |
| 14 | RPRM_2 | 14 |
| 15 | CDH4_24735 | 15 |
| 16 | CPT1C_23912 | 16 |
| 17 | SLIT2_23676 | 17 |
| 18 | PAX1_27211 | 18 |
| 19 | DKK2_23970 | 19 |
| 20 | TERT_23702 | 20 |
| 21 | NOL4_19645 | 21 |
| 22 | HOXA11_23844 | 22 |
| 23 | CALCA_2 | 23 |
| 24 | C13orf18_19885 | 24 |
| 25 | PAX1_27210 | 25 |
| 26 | WIT1_24567 | 26 |
| 27 | GATA4_13295 | 27 |
| 28 | SLIT1_23651 | 28 |
| 29 | LOC285016_22940 | 29 |
| 30 | POMC | 30 |
| 31 | Gst-Pi_New3 | 32 |
| 32 | DAPK1 | 34 |
| 33 | GDAP1L1_19773 | 35 |
| 34 | TFPI-2 | 36 |
| 35 | TWIST1_9329 | 37 |
| 36 | SST_23808 | 38 |
| 37 | EGR4_24277 | 39 |
| 38 | C16orf48_22922 | 45 |
| 39 | DBC1_23879 | 46 |
| 40 | GDAP1L1_19775 | 47 |
| 41 | OGFOD2_23131 | 48 |
| 42 | ALX4_25062 | 49 |
| 43 | TLL1_24051 | 51 |
| 44 | CTDSPL_23795 | 52 |
| 45 | CYCLIND2_1 | 58 |
| 46 | COL1A1_23253 | 65 |
| 47 | CDK6_9703 | 71 |
| 48 | CDH1_17968 | 76 |
| 49 | SOCS1_23595 | 78 |
| 50 | FOXE1_13314 | 91 |
| 51 | BMP2_17901 | 94 |
| 52 | AURKA_24802 | 110 |
| 53 | SEMA3F_23485 | 120 |
| 54 | PAK3_3 | 121 |
| 55 | HOXA7_2 | 125 |
| 56 | CTDSPL_23804 | 127 |
| 57 | NPTX1_2 | 136 |
| 58 | SLIT1_23653 | 164 |
| 59 | SMPD1_24061 | 174 |
| 60 | GADD45A_24463 | 250 |
| 61 | KRAS_24235 | 281 |
| 62 | RECK_18940 | 321 |
| 63 | UGT1A1_22912 | 341 |
| 64 | Beta_Actin | Internal control |

Tissue slides were deparaffinized using 100% xylene followed by 100% ethanol. Pellet was resuspended in a buffer containing SDS-proteinase K, and DNA was extracted with phenol-chloroform followed by ethanol precipitation. DNA concentration was measured using NanoDrop Spectrophotometer. From each sample, up to 3 μg of genomic DNA was converted using a bisulphite based protocol (EZ DNA Methylation Kit™, ZYMO Research). After DNA conversion and purification, equivalent of 20 ng of gDNA was used per reaction. All the samples were tested on Lightcycler using Sybergreen as detector and the amplicon size was determined by capillary electrophoresis.

Quality control was performed using in vitro methylated DNA sample, unmethylated DNA sample (Chemicon International, CA, USA; Cat.#57821 and Cat.#57822) and no template control sample ($H_2O$). From the Lightcycler platform, the Ct values (cycle number at which the amplification curves cross the threshold value, set automatically by the software) and melting curves (Tm) were generated. From the capillary electrophoresis platform, size of the amplicon and intensity of the signal detected were generated. For each assay, Tm and amplicon size parameters were determined in in vitro methylated DNA sample, unmethylated DNA sample and no template control sample. The measured Tm and amplicon size values were compared to the calculated values. If the Tm or amplicon size values were out of the range of the calculated ones, the assay was considered as non specific and disqualified. All the 64 assays were specific.

A sample is considered methylated if Ct is under 40 and if Tm and amplicon size are within the boundaries of Tm+/−2 degrees and amplicon size+/−10 bp. The intensity of the band detected by capillary electrophoresis had to be higher than 20. Those evaluation criteria have been developed based on concordance with existing Molecular Beacon based qMSP assays, to ensure that the conclusions drawn from these data would be predictive of MSP assays developed subsequently.

DNA methylation calls were compared between cervical cancer and control patients. An assay ranking with the set of samples was generated and the results are summarized in the methylation table of FIG. 6. A one-tailed Fisher's exact test was used as a scoring function to rank the candidate markers. The calculation of Fisher's exact test was based on a formula as described by Haseeb Ahmad Khan in "A visual basic software for computing Fisher's exact probability" (*Journal of Statistical Software*, vol. 08, issue i21, 2003).

A comparison between the results coming from the Base 5 (Biotrove) and the Lightcycler platforms has been performed. Most of the interesting assays discovered on the Base 5 platform were confirmed on the Lightcycler platform.

Example 4

QMSP

Seventeen assays (ALX3, C13ORF18, DBC1, EPB41L3, GATA4, HOXA11, JAM3, JPH3, LMX1A, NOL4, PAK3, SLIT2_23672, SLIT2_23676, SOX1, TERT, TFPI2 and TWIST1_3) were further selected based on their performance on the Biotrove and Lightcycler platforms and on complementarity analysis to maximize discriminatory power. For these assays, qMSPs using Molecular Beacon as detection system were designed (3 designs, if possible, were evaluated per assay) and tested on control samples. For this selection, assays were judged on several criteria, including background fluorescence, dynamic of the curve, and level of fluorescence generated. PCR material was used for generating standard curves for quantification of the results.

Five assays did not meet the desired specifications (EPB41L3, SOX1, SLIT2_23672, DBC1, and SLIT2_23676) and may be redesigned in a later phase or can be used on another detection platform. The remaining 12 assays were further tested on converted DNA of cervix cancer cell lines.

All these results were taken into account to decide which assays should be further verified on cervical tissue samples collected by Ulg (normal PE tissue samples #13, cancer PE tissue samples #17) and/or UMCG (normal frozen tissue samples #20, cancer frozen tissue samples #27).

Seventeen (CCNA1, CDO1_55928, CDO1_55929, GREM1, GPNMB, HIN1, HOXD1, LAMA1, LTB4R, MAL, NDRG2, NID2, NPTX2, RASSF1A, SALL4, SOX17, and TAC1) additional good performing assays were also selected for further verification on the cervix tissue samples. These candidates were taken from other in-house cancer projects, and were not tested on the Biotrove/Lightcycler platform as described above.

DNA was isolated from the cervix tissue samples using a phenol-chloroform procedure, quantified using the picogreen method and 1.5 μg of DNA was bisulphite treated using the ZYMO kit.

qMSPs were carried out in a total volume of 12 μl in 384 well plates in an ABI PRISM 7900HT instrument (Applied Biosystems). The final reaction mixture consisted of in-house qMSP buffer (including 80.4 nmol of MgCl2), 60 nmol of each dNTP, 0.5 U of Jump Start Taq polymerase (SIGMA), 72 ng of forward primer, 216 ng of reverse primer, 1.92 pmol of Molecular Beacon detection probe, 6.0 pmol of ROX (passive reference dye) and 72 ng of bisulphite converted genomic DNA. Thermal cycling was initiated with an incubation step of 5 minutes at 95° C., followed by 45 cycles (95° C. for 30 seconds, 57° C. for 30 seconds, 72° C. for 30 seconds). A finalizing step was performed at 72° C. for 5 minutes to conclude cycling. These conditions were similar for all the test genes as well as for ACTB. Cell lines [in vitro methylated DNA sample and unmethylated DNA sample (Chemicon International, CA, USA; Cat.#57821 and Cat.# S7822)] were included in each run as positive and negative controls, and entered the procedure at the DNA extraction step. Primers and molecular beacon sequences used for the different qMSPs are summarized in Table 1 and Table 3. Corresponding amplicons are summarized in Table 2.

Ct values were determined using the SDS software (version 2.2.2.) supplied by Applied Biosystems with automatic baseline settings and threshold. The slopes and $R^2$ values for the different standard curves were determined after exporting data into MS Excel.

Figure 7:
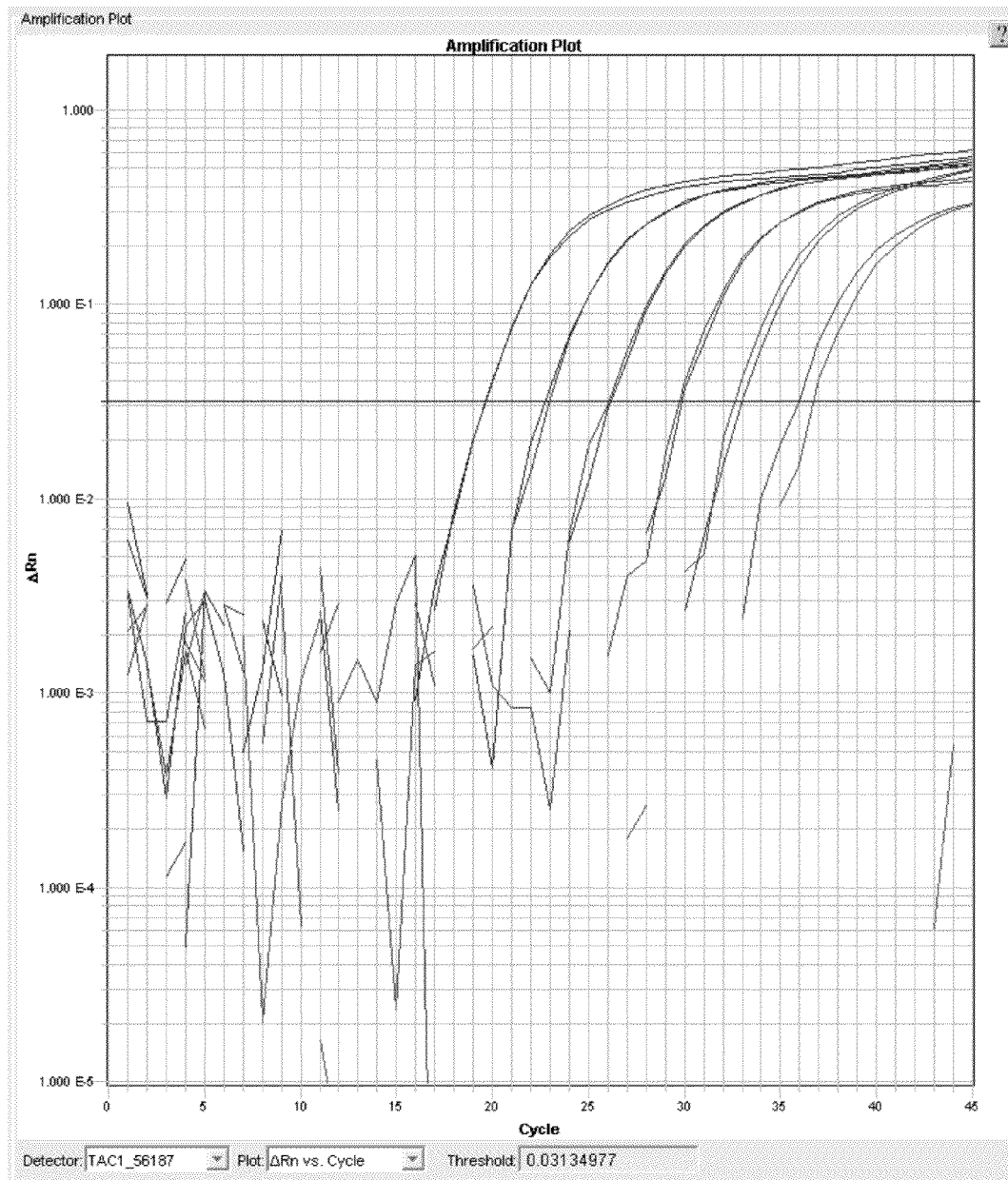

As an example, FIG. 7 shows the amplification plot obtained for the standard curve for TAC1_56187 (960000 copies to 9.6 copies of the gene) and FIG. 8 shows the amplification plot obtained for the standard curve and for all samples for TAC1_56187. The Ct values plotted against the Log Copies of TAC1_56187 (FIG. 9) give a $R^2$ of 0.9995 and the efficiency of the reaction is 99.35%.

In addition to the test genes, the independent reference gene β-actin (ACTB) was also measured. The ratios between the test genes and ACTB were calculated to generate the test result. The samples were classified as methylated, unmethylated, or invalid based on the decision tree shown in FIG. 10.

A provisional cut-off was defined for each gene, chosen based on the greater of either the highest value seen among the controls or a value 3 times the standard deviation of the values from control samples.

The one-tailed Fisher's exact test as described above was used as a scoring function to rank the candidate markers (*Journal of Statistical Software*, vol. 08, issue i21, 2003).

Table 7 summarizes the results obtained for TAC1_56187. Table 8 summarizes the results obtained for all the tested markers on tissue samples. The individual performances of the assays are shown in FIG. 11 and the assays are ranked according their p-value (Fisher's exact test). The best performing markers were further tested on clinical samples (scrapings).

TABLE 7

Summary of the test results for TAC1_56187 on cervix tissue samples. In column "methylation status", the black boxes indicate the methylated results; white boxes indicate the unmethylated results.

| Sample | TAC1_56187_Ratio | Methylation Status |
|---|---|---|
| normal | 5.0 | 0 |
| normal | 0.0 | 0 |
| normal | 0.0 | 0 |
| normal | 0.0 | 0 |
| normal | 4.3 | 0 |
| normal | 0.0 | 0 |
| normal | 1.4 | 0 |
| normal | 13.2 | 0 |
| normal | 3.5 | 0 |
| normal | 0.8 | 0 |
| normal | 0.0 | 0 |
| normal | 0.0 | 0 |
| normal | 3.0 | 0 |
| normal | 6.1 | 0 |
| normal | 2.5 | 0 |
| normal | 0.0 | 0 |
| normal | 2.2 | 0 |
| normal | 5.2 | 0 |
| normal | 0.8 | 0 |
| normal | 20.0 | 0 |
| normal | 0.0 | 0 |
| normal | 0.0 | 0 |
| normal | 0.0 | 0 |
| normal | 0.0 | 0 |
| normal | 0.0 | 0 |
| normal | 13.7 | 0 |
| normal | 0.0 | 0 |
| normal | 0.0 | 0 |
| normal | 0.0 | 0 |
| normal | 0.0 | 0 |
| normal | 0.0 | 0 |
| normal | 0.0 | 0 |
| normal | 10.8 | 0 |
| normal | 9.8 | 0 |
| normal | 21.9 | 0 |
| normal | 15.8 | 0 |
| normal | 0.0 | 0 |
| normal | 0.0 | 0 |
| cancer | 19.1 | 0 |
| cancer | 0.0 | 0 |
| cancer | 330.7 | 1 |
| cancer | 92.6 | 1 |
| cancer | 7.3 | 0 |
| cancer | 784.9 | 1 |
| cancer | 23.5 | 0 |
| cancer | 245.2 | 1 |
| cancer | 1235.0 | 1 |
| cancer | 0.0 | 0 |
| cancer | 1256.1 | 1 |
| cancer | 570.0 | 1 |
| cancer | 3.3 | 0 |
| cancer | 30.0 | 1 |
| cancer | 191.0 | 1 |
| cancer | 11.6 | 0 |
| cancer | 110.0 | 1 |
| cancer | 777.1 | 1 |
| cancer | 2944.3 | 1 |
| cancer | 66.5 | 1 |
| cancer | 843.7 | 1 |
| cancer | 208.7 | 1 |
| cancer | 257.0 | 1 |
| cancer | 750.0 | 1 |
| cancer | 542.5 | 1 |
| cancer | 378.5 | 1 |
| cancer | 720.5 | 1 |
| cancer | 323.6 | 1 |
| cancer | 937.3 | 1 |
| cancer | 657.8 | 1 |
| cancer | 482.7 | 1 |
| cancer | 772.8 | 1 |
| cancer | 781.5 | 1 |
| cancer | 67.5 | 1 |
| cancer | 742.9 | 1 |
| cancer | 797.1 | 1 |
| cancer | 304.9 | 1 |
| cancer | 765.0 | 1 |
| cancer | 331.0 | 1 |
| cancer | 1111.0 | 1 |
| cancer | 383.5 | 1 |
| cancer | 703.7 | 1 |
| cancer | 237.6 | 1 |
| cancer | 718.2 | 1 |
| cancer | 541.1 | 1 |
| cancer | 348.3 | 1 |

| | |
|---|---|
| N Normals | 38 |
| N Cancers | 46 |
| Sensitivity | 85 |
| Specificity | 100 |
| Cut off | 25 |
| STDEV (Normals) *3 | 18.0 |
| Cncr Meth + | 39 |
| Cncr Meth - | 7 |
| Cntrl Meth + | 0 |
| Cntrl Meth - | 38 |
| p-value (Fisher test) | 3.94E-17 |

TABLE 8

Summary of the performance results of all the tested markers on tissue samples.

| Assays | NID2_9091_Gron | LMX1A_9513 | TAC1_56187 | NOL4_19645 | JAM3 | CDO1_55929 | CDO1_55928 | SOX17_66072 | GATA4 | TERT_23702 | JPH3 | HOXA11_23844 | LAMA1_63431 | CCNA1_Gron |
|---|---|---|---|---|---|---|---|---|---|---|---|---|---|---|
| Ranking Lightcycler | NA | 12 | NA | 3 | 1 | NA | NA | NA | 21 | 8 | 7 | 10 | NA | NA |
| Ranking Base5 | NA | 1 | NA | 21 | 8 | 6 | 7 | 8 | 27 | 20 | 9 | 22 | NA | NA |
| Ranking qMSP tissue | 1 | 2 | 3 | 4 | 5 | 6 | 7 | 8 | 9 | 10 | 11 | 12 | 13 | 14 |
| Sensitivity | 95 | 85 | 85 | 91 | 83 | 88 | 81 | 80 | 71 | 65 | 72 | 65 | 59 | 60 |
| Specificity | 97 | 100 | 100 | 95 | 100 | 100 | 97 | 97 | 97 | 100 | 97 | 100 | 100 | 97 |
| Cut off | 2 | 10 | 25 | 2 | 5 | 0 | 20 | 35 | 2 | 1 | 1 | 20 | 5 | 15 |
| RatioMax (Normals) | 2 | 10 | 22 | 2 | 5 | 0 | 28 | 51 | 2 | 1 | 1 | 20 | 3 | 15 |
| STDEV (Normals) *3 | 1.5 | 6.5 | 18.0 | 1.9 | 3.5 | 0.0 | 17.7 | 32.0 | 1.3 | 0.5 | 0.6 | 14.2 | 2.2 | 11.6 |
| Cncr Meth+ | 41 | 39 | 39 | 42 | 38 | 38 | 38 | 37 | 42 | 39 | 33 | 28 | 27 | 36 |
| Cncr Meth− | 2 | 7 | 7 | 4 | 8 | 5 | 9 | 9 | 17 | 21 | 13 | 15 | 19 | 24 |
| Cntrl Meth+ | 1 | 0 | 0 | 2 | 0 | 0 | 1 | 1 | 1 | 0 | 1 | 0 | 0 | 1 |
| Cntrl Meth− | 31 | 38 | 38 | 36 | 38 | 32 | 37 | 37 | 38 | 38 | 37 | 32 | 38 | 37 |
| p-value (Fisher test) | 1.42E-17 | 3.94E-17 | 3.94E-17 | 7.55E-17 | 2.27E-16 | 2.79E-16 | 2.08E-14 | 3.66E-14 | 8.90E-13 | 2.40E-12 | 1.06E-11 | 4.82E-10 | 5.53E-10 | 1.03E-09 |

| Assays | C13ORF18_Gron | MAL | GREM1_29777 | TFPI2 | GPNMB_52607 | NDRG2_56603 | NPTX2_57779 | CDO1_55928 | ALX3_25180 | HIN1_3 | SALL4_12833 | PAK3_1 | HOXD1_(2) | LTB4R_31250 | RASSF1a |
|---|---|---|---|---|---|---|---|---|---|---|---|---|---|---|---|
| Ranking Lightcycler | 15 | NA | NA | 16 | NA | NA | NA | 25 | NA | NA | NA | 6 | NA | NA | NA |
| Ranking Biotrove | 24 | NA | NA | 36 | NA | NA | NA | 7 | NA | NA | NA | 121 | NA | NA | NA |
| Ranking qMSP tissue | 15 | 16 | 17 | 18 | 19 | 20 | 21 | 22 | 22 | 23 | 24 | 25 | 26 | 27 | 28 |
| Sensitivity | 65 | 53 | 51 | 60 | 50 | 59 | 55 | 55 | 55 | 50 | 33 | 30 | 30 | 60 | 45 |
| Specificity | 97 | 100 | 97 | 100 | 100 | 95 | 100 | 100 | 100 | 100 | 97 | 100 | 95 | 68 | 74 |
| Cut off | 2 | 1 | 2 | 5 | 5 | 5 | 30 | 5 | 5 | 1 | 1 | 10 | 50 | 20 | 0 |
| RatioMax (Normals) | 3 | 0 | 3 | 5 | 4 | 6 | 29 | 3 | 3 | 0 | 35 | 6 | 59 | 28 | 0 |
| STDEV (Normals) *3 | 1.8 | 0.3 | 1.8 | 3.1 | 2.7 | 4.5 | 24.3 | 2.0 | 2.0 | 0.2 | 18.5 | 4.2 | 45.2 | 17.9 | 0.2 |

TABLE 8-continued

Summary of the performance results of all the tested markers on tissue samples.

| | | | | | | | | | | | |
|---|---|---|---|---|---|---|---|---|---|---|---|
| Cncr Meth+ | 28 | 23 | 22 | 12 | 17 | 20 | 11 | 11 | 10 | 14 | 6 | 6 | 12 | 9 |
| Cncr Meth− | 15 | 20 | 21 | 8 | 17 | 14 | 9 | 9 | 10 | 29 | 14 | 14 | 8 | 11 |
| Cntrl Meth+ | 1 | 0 | 1 | 0 | 0 | 1 | 0 | 0 | 0 | 1 | 0 | 1 | 6 | 5 |
| Cntrl Meth− | 31 | 32 | 31 | 19 | 19 | 18 | 19 | 19 | 19 | 32 | 19 | 18 | 13 | 14 |
| p-value (Fisher test) | 9.66E-09 | 8.07E-08 | 2.91E-06 | 3.22E-05 | 7.22E-05 | 8.61E-05 | 1.00E-04 | 1.00E-04 | 2.91E-04 | 9.64E-04 | 1.19E-02 | 5.29E-02 | 7.19E-02 | 1.89E-01 |

Example 5
Best Performing Markers Tested on Clinical Cervical Scraping Samples Cervical scraping samples were collected under the Cervical Cancer Clinical Collaborative Research Agreement study of ONCO with the Gynecology Department of the UMCG hospital. The scraping samples were taken from patients who were referred to the hospital with an abnormal PAP smear or because they were suspected for cervical carcinoma. Gynecological examination under general anesthesia was performed in all cervical cancer patients for staging in accordance with the International Federation of Gynecology and Obstetrics (FIGO) criteria. Control scraping samples were taken from women who visited the hospital for a non-malignant condition, e.g. fibroids, prolaps uteri or hypermenorrhea, and who were scheduled to undergo a hysterectomy. While the patient was under general anesthesia, the cervix was scraped with an Ayres spatula and brush. The scraped cells were suspended in 5-ml PBS. Cytospins for cytomorphological assessment were made (⅕ volume). Cytospins were Papanicolaou stained and routinely classified according to a modified Papanicolaou system (Hanselaar AG. Kwaliteit van cytopathologisch onderzoek in het herziene bevolkingsonderzoek naar baarmoederhalskanker. Nederlands Tijdschrift voor Obstetrie en Gynaecologie 1996; 109:207-210) without knowledge of the clinical data. The remaining 4-ml of the scraped cells was centrifuged, washed, aliquoted, snap-frozen in liquid nitrogen and stored at −80° C. DNA was extracted using standard salt-chloroform extraction and ethanol precipitation. DNA of the pellet was used for qMSP of a panel of good performing markers for cervical cancer and also for HPV typing.

DNA was extracted from the scraped cells using standard salt-chloroform extraction and ethanol precipitation for high molecular DNA, dissolved in 250 μL TE-4 buffer (10 mM Tris; 1 mM EDTA, pH 8.0) and kept at −20° C. until tested.

Presence of high risk HPV was analyzed by PCR using HPV16 and HPV18 specific primers on DNA of the scraping samples. On all HPV16- or HPV18-negative cases, general primer-mediated PCR was performed using two HPV consensus primer sets, CPI/CPIIG and GPS+/6+, with subsequent nucleotide sequence analysis, as described previously [by Wisman et al Int j cancer 2006].

qMSP was performed after bisulphite treatment on denatured genomic DNA. The assays were carried out as described above. The samples were classified as methylated, unmethylated, or invalid as described above. The results obtained for all the tested markers on scraping samples from cervical cancer patients and from control patients were ranked according their p-value (Fisher's exact test) (Table 9). Some markers have a higher sensitivity for squamous cell carcinoma than for adenocarcinoma (NID2, JPH3, CCNA1) and some markers have a higher sensitivity for adenocarcinoma than for squamous cell carcinoma (JAMS, CDO1, HOXA11).

Various combinations of markers were evaluated to see if such a combination could increase the sensitivity while still maintaining a high level of specificity. In all cases, if any marker of a combination panel was positive, the sample was classified as methylated. Examples of the performance of combination of markers are summarized in Table 10. It can be seen that several combinations provided a sensitivity and specificity greater than 90%.

TABLE 9

Summary of the results obtained for all the tested markers on scraping samples from cervical cancer patients and from control patients (Sens: sensitivity; SCC: squamous cell carcinoma; Ade: adenocarcinoma; cncr: cancer; ctrl: control).

|  | JAM3 | NID2_ 9091 | CDO1_ 55928 | CDO1_ 55929 | LMX1A_ 9513 | TAC1_ 56187 | GREM1_ 29777 | HOXA11_ 23844 | JPH3 |
|---|---|---|---|---|---|---|---|---|---|
| Sensitivity | 81.0% | 78.5% | 82.3% | 78.5% | 75.9% | 72.2% | 72.2% | 62.0% | 64.6% |
| Specificity | 98.6% | 98.6% | 95.7% | 97.1% | 97.1% | 98.6% | 97.1% | 100.0% | 98.6% |
| Sens SCC | 80.3% | 83.3% | 81.8% | 77.3% | 77.3% | 72.7% | 72.7% | 59.1% | 69.7% |
| Sens Ade | 84.6% | 53.8% | 84.6% | 84.6% | 69.2% | 69.2% | 69.2% | 76.9% | 38.5% |
| cncr test+ | 64 | 62 | 65 | 62 | 60 | 57 | 57 | 49 | 51 |
| cncr test− | 15 | 17 | 14 | 17 | 19 | 22 | 22 | 30 | 28 |
| ctrl test+ | 1 | 1 | 3 | 2 | 2 | 1 | 2 | 0 | 1 |
| ctrl test− | 68 | 68 | 66 | 67 | 67 | 68 | 67 | 69 | 68 |
| SCC test+ | 53 | 55 | 54 | 51 | 51 | 48 | 48 | 39 | 46 |
| SCC test− | 13 | 11 | 12 | 15 | 15 | 18 | 18 | 27 | 20 |
| Ade test+ | 11 | 7 | 11 | 11 | 9 | 9 | 9 | 10 | 5 |
| Ade test− | 2 | 6 | 2 | 2 | 4 | 4 | 4 | 3 | 8 |
| cncr/ctrl p-val | 4.75E−26 | 1.21E−24 | 4.57E−24 | 3.11E−23 | 6.24E−22 | 1.86E−21 | 4.17E−20 | 1.23E−18 | 4.12E−18 |
| Ade/SCC p-val | 5.32E−01 | 2.31E−02 | 5.84E−01 | 4.33E−01 | 3.37E−01 | 4.79E−01 | 4.79E−01 | 1.86E−01 | 3.53E−02 |
| Cut off | 2 | 5 | 5 | 35 | 15 | 15 | 10 | 1 | 5 |

|  | GATA-4 | C13orf18_ Gron | CCNA1_ Gron | TERT_ 23702 | NDRG2_ 56603 | NOL4_ 19645 | LAMA1_ 63431 |
|---|---|---|---|---|---|---|---|
| Sensitivity | 62.0% | 53.2% | 51.9% | 58.2% | 49.4% | 43.0% | 51.9% |
| Specificity | 97.1% | 100.0% | 100.0% | 97.1% | 98.6% | 98.6% | 94.2% |
| Sens SCC | 62.1% | 54.5% | 57.6% | 60.6% | 48.5% | 43.9% | 50.0% |
| Sens Ade | 61.5% | 46.2% | 23.1% | 46.2% | 53.8% | 38.5% | 61.5% |
| cncr test+ | 49 | 42 | 41 | 46 | 39 | 34 | 41 |
| cncr test− | 30 | 37 | 38 | 33 | 40 | 45 | 38 |
| ctrl test+ | 2 | 0 | 0 | 2 | 1 | 1 | 4 |
| ctrl test− | 67 | 69 | 69 | 67 | 68 | 68 | 65 |
| SCC test+ | 41 | 36 | 38 | 40 | 32 | 29 | 33 |
| SCC test− | 25 | 30 | 28 | 26 | 34 | 37 | 33 |
| Ade test+ | 8 | 6 | 3 | 6 | 7 | 5 | 8 |
| Ade test− | 5 | 7 | 10 | 7 | 6 | 8 | 5 |
| cncr/ctrl p-val | 7.73E−16 | 2.91E−15 | 8.21E−15 | 2.03E−14 | 1.59E−12 | 1.61E−10 | 2.17E−10 |
| Ade/SCC p-val | 6.43E−01 | 4.00E−01 | 2.33E−02 | 2.54E−01 | 4.80E−01 | 4.81E−01 | 3.25E−01 |
| Cut off | 2 | 0 | 1 | 5 | 150 | 5 | 10 |

TABLE 10

Examples of the performance of combination of markers on scraping samples from cervical cancer patients and from control patients (Sens: sensitivity; SCC: squamous cell carcinoma; Ade: adenocarcinoma; cncr: cancer; ctrl: control).

| | NID2_9091\ HOXA11_23844 | JAM3\ CDO1_55929\ HOXA11_23844\ CCNA1_Gron | JAM3\ HOXA11_23844 | JAM3\ HOXA11_23844\ GREM1_29777 | JAM3\ NID2_9091\ HOXA11_23844\ CDO1_55929 | JAM3\ TAC1_56187\ HOXA11_23844\ CDO1_55929 |
|---|---|---|---|---|---|---|
| Sensitivity | 89.9% | 92.4% | 88.6% | 91.1% | 92.4% | 92.4% |
| Specificity | 98.6% | 95.7% | 98.6% | 95.7% | 94.2% | 94.2% |
| Sens SCC | 92.4% | 92.4% | 89.4% | 92.4% | 92.4% | 92.4% |
| Sens Ade | 76.9% | 92.3% | 84.6% | 84.6% | 92.3% | 92.3% |
| cncr test+ | 71 | 73 | 70 | 72 | 73 | 73 |
| cncr test− | 8 | 6 | 9 | 7 | 6 | 6 |
| ctrl test+ | 1 | 3 | 1 | 3 | 4 | 4 |
| ctrl test− | 68 | 66 | 68 | 66 | 65 | 65 |
| SCC test+ | 61 | 61 | 59 | 61 | 61 | 61 |
| SCC test− | 5 | 5 | 7 | 5 | 5 | 5 |
| Ade test+ | 10 | 12 | 11 | 11 | 12 | 12 |
| Ade test− | 3 | 1 | 2 | 2 | 1 | 1 |
| p-val cncr/ctrl | 8.14E−32 | 6.60E−31 | 6.87E−31 | 6.62E−30 | 1.17E−29 | 1.17E−29 |

| | JAM3\ HOXA11_23844\ CDO1_55929 | JAM3\ CDO1_55928 | JAM3\ NID2_9091 | NID2_9091\ CDO1_55928 |
|---|---|---|---|---|
| Sensitivity | 92.4% | 89.9% | 86.1% | 88.6% |
| Specificity | 94.2% | 94.2% | 97.1% | 94.2% |
| Sens SCC | 92.4% | 89.4% | 86.4% | 89.4% |
| Sens Ade | 92.3% | 92.3% | 84.6% | 84.6% |
| cncr test+ | 73 | 71 | 68 | 70 |
| cncr test− | 6 | 8 | 11 | 9 |
| ctrl test+ | 4 | 4 | 2 | 4 |
| ctrl test− | 65 | 65 | 67 | 65 |
| SCC test+ | 61 | 59 | 57 | 59 |
| SCC test− | 5 | 7 | 9 | 7 |
| Ade test+ | 12 | 12 | 11 | 11 |
| Ade test− | 1 | 1 | 2 | 2 |
| p-val cncr/ctrl | 1.17E−29 | 9.85E−28 | 1.13E−27 | 7.67E−27 |

HPV testing will certainly continue to occupy a significant position in the diagnosis of cervical cancer. With this in mind, the best performing methylation markers were tested on scraping samples from patients who were referred to the hospital with an abnormal Pap smear and these samples were also tested for hr HPV and HPV16. The provisional cut off as defined above was reduced in order to obtain the highest possible sensitivity and specificity compared to the performance of hrHPV. The results of these tests are shown in Table 11. For these testing, the classification of pre-cancerous (CIN) conditions were used. Sensitivity was calculated for samples indicating cancer, CIN 2 and CIN 3, while specificity was calculated for those samples from controls, and those indicating CIN 1 or CIN 0 after cytological examination. Overall the specificity of the methylation markers was higher compared to hr-HPV or HPV16 testing but with a lower sensitivity. Combinations of methylation markers (where at least one of the markers scores positive) showed a comparable sensitivity and specificity for cancers and controls, but a much higher specificity for CIN0 and CIN1. The sensitivity for CIN3 and CIN2 is however somewhat lower. In order to increase the sensitivity for CIN3 and CIN2 detection, an analysis was made of combining the results of methylation markers and HPV16 (Table 12). The sensitivity as well as the specificity increased if HPV16 was combined with the methylation markers.

TABLE 11

Overall summary of the methylation marker(s) results on scraping samples from patients who were referred to the hospital with an abnormal Pap smear, and from cervical cancer and control patients. (Sens: sensitivity; Spec: specificity; CIN0, CIN1, CIN2, CIN3: cervical intraepithelial neoplasia grade 0, 1, 2, and 3; cncr: cancer; ctrl: control; NA: not applicable).

| | hr-HPV | HPV16 | JAM3 | NID2_9091 | LMX1A_9513 | CDO1_55928 | TAC1_56187 | C13ORF18_Gron |
|---|---|---|---|---|---|---|---|---|
| Sens Cncr | 90% | 77% | 83% | 80% | 82% | 83% | 73% | 54% |
| Sens CIN3 | 95% | 83% | 38% | 40% | 60% | 43% | 17% | 24% |
| Sens CIN2 | 74% | 45% | 21% | 29% | 29% | 24% | 7% | 5% |
| Spec Cntrl | 96% | 99% | 99% | 93% | 94% | 91% | 93% | 100% |
| Spec CIN0 | 51% | 91% | 98% | 95% | 91% | 98% | 100% | 100% |
| Spec CIN1 | 34% | 78% | 98% | 93% | 85% | 88% | 100% | 98% |
| Overall sens | 87% | 70% | 56% | 57% | 63% | 58% | 42% | 34% |
| Overall spec | 67% | 91% | 98% | 93% | 91% | 92% | 97% | 99% |
| Cut off | NA | NA | 1 | 2 | 10 | 3 | 10 | 0 |

TABLE 11-continued

Overall summary of the methylation marker(s) results on scraping samples from patients who were referred to the hospital with an abnormal Pap smear, and from cervical cancer and control patients. (Sens: sensitivity; Spec: specificity; CIN0, CIN1, CIN2, CIN3: cervical intraepithelial neoplasia grade 0, 1, 2, and 3; cncr: cancer; ctrl: control, NA: not applicable).

| | | | | | | | | |
|---|---|---|---|---|---|---|---|---|
| cncr test+ | 74 | 63 | 68 | 66 | 67 | 68 | 60 | 44 |
| cncr test− | 8 | 19 | 14 | 16 | 15 | 14 | 22 | 38 |
| CIN3 test+ | 40 | 35 | 16 | 17 | 25 | 18 | 7 | 10 |
| CIN3 test− | 2 | 7 | 26 | 25 | 17 | 24 | 35 | 32 |
| CIN2 test+ | 31 | 19 | 9 | 12 | 12 | 10 | 3 | 2 |
| CIN2 test− | 11 | 23 | 33 | 30 | 30 | 32 | 39 | 40 |
| ctrl test+ | 3 | 1 | 1 | 5 | 4 | 6 | 5 | 0 |
| ctrl test− | 66 | 68 | 68 | 64 | 65 | 63 | 64 | 69 |
| CIN0 test+ | 21 | 4 | 1 | 2 | 4 | 1 | 0 | 0 |
| CIN0 test− | 22 | 39 | 42 | 41 | 39 | 42 | 43 | 43 |
| CIN1 test+ | 27 | 9 | 1 | 3 | 6 | 5 | 0 | 1 |
| CIN1 test− | 14 | 32 | 40 | 38 | 35 | 36 | 41 | 40 |

| | JAM3\NID2_9091 | JAM3\LMX1A_9513 | JAM3\CDO1_55928 | JAM3\CDO1_55928\NID2_9091 | NID2\LMX1A_9513 |
|---|---|---|---|---|---|
| Sens Cncr | 88% | 87% | 90% | 91% | 88% |
| Sens CIN3 | 45% | 62% | 52% | 57% | 67% |
| Sens CIN2 | 33% | 36% | 31% | 38% | 43% |
| Spec Cntrl | 93% | 93% | 90% | 84% | 88% |
| Spec CIN0 | 95% | 93% | 98% | 95% | 91% |
| Spec CIN1 | 93% | 83% | 88% | 83% | 83% |
| Overall sens | 63% | 67% | 66% | 69% | 71% |
| Overall spec | 93% | 90% | 92% | 87% | 88% |
| Cut off | NA | NA | NA | NA | NA |
| cncr test+ | 72 | 71 | 74 | 75 | 72 |
| cncr test− | 10 | 11 | 8 | 7 | 10 |
| CIN3 test+ | 19 | 26 | 22 | 24 | 28 |
| CIN3 test− | 23 | 16 | 20 | 18 | 14 |
| CIN2 test+ | 14 | 15 | 13 | 16 | 18 |
| CIN2 test− | 28 | 27 | 29 | 26 | 24 |
| ctrl test+ | 5 | 5 | 7 | 11 | 8 |
| ctrl test− | 64 | 64 | 62 | 58 | 61 |
| CIN0 test+ | 2 | 3 | 1 | 2 | 4 |
| CIN0 test− | 41 | 40 | 42 | 41 | 39 |
| CIN1 test+ | 3 | 7 | 5 | 7 | 7 |
| CIN1 test− | 38 | 34 | 36 | 34 | 34 |

TABLE 12

Overall summary results of methylation marker(s) in combination with HPV16 on scraping samples from patients who were referred to the hospital with an abnormal Pap smear, and from cervical cancer and control patients. (Sens: sensitivity; Spec: specificity; CIN0, CIN1, CIN2, CIN3: cervical intraepithelial neoplasia grade 0, 1, 2, and 3; cncr: cancer; ctrl: control).

| | hr-HPV | HPV16 | JAM3\HPV16 | NID2_9091\HPV16 | LMX1A_9513\HPV16 | CDO1_55928\HPV16 | PAC1_56187\HPV16 | C13ORF18_Gron\HPV16 |
|---|---|---|---|---|---|---|---|---|
| Sens Cncr | 90% | 77% | 95% | 93% | 94% | 99% | 93% | 83% |
| Sens CIN3 | 95% | 83% | 88% | 90% | 88% | 88% | 83% | 86% |
| Sens CIN2 | 74% | 45% | 60% | 62% | 60% | 60% | 50% | 45% |
| Spec Cntrl | 96% | 99% | 97% | 93% | 93% | 90% | 91% | 99% |
| Spec CIN0 | 51% | 91% | 88% | 86% | 84% | 88% | 91% | 91% |
| Spec CIN1 | 34% | 78% | 78% | 73% | 66% | 73% | 78% | 76% |
| CIN0 test− | 22 | 39 | 38 | 37 | 36 | 38 | 39 | 39 |
| CIN0 test+ | 21 | 4 | 5 | 6 | 7 | 5 | 4 | 4 |
| CIN1 test− | 14 | 32 | 32 | 30 | 27 | 30 | 32 | 31 |
| CIN1 test+ | 27 | 9 | 9 | 11 | 14 | 11 | 9 | 10 |
| CIN2 test− | 11 | 23 | 17 | 16 | 17 | 17 | 21 | 23 |
| CIN2 test+ | 31 | 19 | 25 | 26 | 25 | 25 | 21 | 19 |
| CIN3 test− | 2 | 7 | 5 | 4 | 5 | 5 | 7 | 6 |
| CIN3 test+ | 40 | 35 | 37 | 38 | 37 | 37 | 35 | 36 |
| cncr test− | 8 | 19 | 4 | 6 | 5 | 1 | 6 | 14 |
| cncr test+ | 74 | 63 | 78 | 76 | 77 | 81 | 76 | 68 |
| ctrl test− | 66 | 68 | 67 | 64 | 64 | 62 | 63 | 68 |
| ctrl test+ | 3 | 1 | 2 | 5 | 5 | 7 | 6 | 1 |
| Overall sens | 87% | 70% | 84% | 84% | 84% | 86% | 80% | 74% |
| Overall spec | 67% | 91% | 90% | 86% | 83% | 85% | 88% | 90% |

TABLE 12-continued

Overall summary results of methylation marker(s) in combination with HPV16 on scraping samples from patients who were referred to the hospital with an abnormal Pap smear, and from cervical cancer and control patients. (Sens: sensitivity; Spec: specificity; CIN0, CIN1, CIN2, CIN3: cervical intraepithelial neoplasia grade 0, 1, 2, and 3; cncr: cancer; ctrl: control).

|  | JAM3\NID2_9091\HPV16 | JAM3\LMX1A_9513\HPV16 | JAM3\CDO1_55928\HPV16 | JAM3\CDO1_55928\NID2_9091\HPV16 | NID2\LMX1A_9513\HPV16 |
|---|---|---|---|---|---|
| Sens Cncr | 98% | 96% | 100% | 100% | 96% |
| Sens CIN3 | 90% | 88% | 88% | 90% | 90% |
| Sens CIN2 | 67% | 64% | 64% | 67% | 67% |
| Spec Cntrl | 93% | 91% | 88% | 84% | 88% |
| Spec CIN0 | 86% | 84% | 88% | 86% | 81% |
| Spec CIN1 | 73% | 66% | 73% | 68% | 66% |
| CIN0 test− | 37 | 36 | 38 | 37 | 35 |
| CIN0 test+ | 6 | 7 | 5 | 6 | 8 |
| CIN1 test− | 30 | 27 | 30 | 28 | 27 |
| CIN1 test+ | 11 | 14 | 11 | 13 | 14 |
| CIN2 test− | 14 | 15 | 15 | 14 | 14 |
| CIN2 test+ | 28 | 27 | 27 | 28 | 28 |
| CIN3 test− | 4 | 5 | 5 | 4 | 4 |
| CIN3 test+ | 38 | 37 | 37 | 38 | 38 |
| cncr test− | 2 | 3 | 0 | 0 | 3 |
| cncr test+ | 80 | 79 | 82 | 82 | 79 |
| ctrl test− | 64 | 63 | 61 | 58 | 61 |
| ctrl test+ | 5 | 6 | 8 | 11 | 8 |
| Overall sens | 88% | 86% | 88% | 89% | 87% |
| Overall spec | 86% | 82% | 84% | 80% | 80% |

As cytology is currently been used and hr-HPV testing has been suggested as primary screening tool in population-based cervical screening, we simulated the effect on the performances of the methylation tests if only cytology (Table 13) or hr-HPV (Table 14) positive patients were selected. The triage simulations were based on the performance results obtained in Table 11 and Table 12. The performance of cytology and hr-HPV testing were based on data from literature.

The performances of the triage tests showed much higher specificity resulting in fewer referrals for colposcopy than did cytology or hr-HPV testing alone but were less sensitive. Testing for hr-HPV types has a higher sensitivity for detecting CIN2+ than cytology. The NPV is close to 100% thus allowing for less frequent screening and longer screening intervals without jeopardizing patients' safety. But, the enthusiasm for using HPV testing in primary screening has been tempered by its somewhat poorer PPV (19%) in comparison with cytological analysis (27%). Using methylation as triage test, the PPVs were much higher.

Taking the limitations of cytology and the decreased disease prevalence due to the introduction of HPV vaccination programs into account, it is proposed to use a highly sensitive and objective screening test such as HPV DNA testing to identify the rare cases of cancer precursors and to combine it, when positive, with another test which has a high degree of specificity, such as methylation testing. Moreover, methylation is measuring changes in the host cells, as precursor of cervix cancer, while HPV is detecting the causative agent. This is an ideal methodology for a screening and a triage assay because they should measure different but complementary biological signals.

TABLE 13

The simulation of the performance of Cytology test as a first-line screening test on 70000 women and the methylation marker test(s) in-or excluding HPV16 as triage test. (Sens: sensitivity; Spec: specificity; CIN0/1, CIN2+: cervical intraepithelial neoplasia grade 0 and 1, and grade 2 and 3 and cancers; PPV: positive predictive value; NPV: negative predictive value).

|  | Cytology | Cytology, Triage hr-HPV | Cytology, Triage HPV16 | Cytology, Triage JAM3\NID2 | Cytology, Triage JAM3\NID2\HPV16 | Cytology, Triage NID2\LMX1A | Cytology, Triage NID2\LMX1A\HPV16 |
|---|---|---|---|---|---|---|---|
| CIN2+ Test+ | 540 | 449 | 334 | 213 | 417 | 290 | 417 |
| CIN2+ Test− | 230 | 321 | 436 | 557 | 353 | 480 | 353 |
| CIN0/1 Test+ | 1460 | 825 | 219 | 85 | 288 | 187 | 374 |
| CIN0/1 Test− | 67770 | 68405 | 69011 | 69145 | 68942 | 69043 | 68856 |
| Sens | 70.1% | 58.3% | 43.4% | 27.6% | 54.2% | 37.7% | 54.2% |
| Spec | 97.9% | 98.8% | 99.7% | 99.9% | 99.6% | 99.7% | 99.5% |
| NPV | 99.7% | 99.9% | 99.7% | 99.5% | 99.8% | 99.6% | 99.8% |
| PPV | 27.0% | 35.2% | 60.4% | 71.4% | 59.1% | 60.8% | 52.7% |
| Colposcopy referrals | 2000 | 1274 | 553 | 298 | 706 | 477 | 791 |

TABLE 14

The simulation of the performance of hr-HPV test as a first-line screening test on 70000 women and the methylation marker test(s) in-or excluding HPV16 as triage test. (Sens: sensitivity; Spec: specificity; CIN0/1, CIN2+: cervical intraepithelial neoplasia grade 0 and 1, and grade 2 and 3 and cancers; PPV: positive predictive value; NPV: negative predictive value).

|  | hr-HPV | hr-HPV, Triage Cytology | hr-HPV, Triage HPV16 | hr-HPV, Triage JAM3\NID2 | hr-HPV, Triage JAM3\NID2\HPV16 | hr-HPV, Triage NID2\LMX1A | hr-HPV, Triage NID2\LMX1A\HPV16 |
|---|---|---|---|---|---|---|---|
| CIN2+ Test+ | 665 | 532 | 433 | 276 | 541 | 376 | 541 |
| CIN2+ Test− | 67 | 285 | 333 | 491 | 226 | 390 | 226 |
| CIN0/1 Test+ | 2835 | 553 | 420 | 164 | 553 | 358 | 717 |
| CIN0/1 Test− | 66433 | 68631 | 68814 | 69070 | 68681 | 68875 | 68517 |
| Sens | 90.8% | 65.1% | 56.5% | 36.0% | 70.6% | 49.1% | 70.6% |
| Spec | 95.9% | 99.2% | 99.4% | 99.8% | 99.2% | 99.5% | 99.0% |
| NPV | 99.9% | 99.6% | 99.6% | 99.4% | 99.8% | 99.5% | 99.8% |
| PPV | 19.0% | 49.0% | 50.8% | 62.7% | 49.5% | 51.2% | 43.0% |
| Colposcopy referrals | 3500 | 1085 | 853 | 440 | 1094 | 735 | 1258 |

REFERENCES

The disclosure of each reference cited in this disclosure is expressly incorporated herein.

Badal et al, The human papillomavirus-18 genome is efficiently targeted by cellular DNA methylation, Virology 324 (2004) 483-492.

Barringer K J, Orgel L, Wahl G, Gingeras T R. Gene. 1990 Apr. 30; 89(1):117-22.

Brink et al, HPV detection methods, Disease Markers 23 (2007) 273-281.

Cottrell, S E et al. A real-time PCR assay for DNA-methylation using methylation-specific blockers. Nuc Acids Res 2004, 32, 1.

Cross, S H et al. Nature Genetics 1994, 6, 236-244.

Deng, D. et al. Simultaneous detection of CpG methylation and single nucleotide polymorphism by denaturing high performance liquid chromatography. 2002 Nuc. Acid Res, 30, 3.

Ehrich, M. et al. 2005. Introduction to DNA methylation analysis using the MassARRAY system. SEQUENOM™ product preview note.

Finan, M. A. et al. (1996) Radical hysterectomy for stage 1B1 vs IB2 carcinoma of the cervix: does the new staging system predict morbidity and survival? *Gynecol Oncol.*, 2, 139-147.

Galm et al. Enzymatic Regional Methylation Assay: A Novel Method to Quantify Regional CpG Methylation Density. Genome Research, Vol. 12, Issue 1, 153-157, January 2002.

Gentleman R C, Carey V J, Bates D M, Bolstad B, Dettling M, et al. (2004) Bioconductor: open software development for computational biology and bioinformatics. Genome Biol 5: R80.

Gitan R S et al. Methylation-specific oligonucleotide microarray: a new potential for high-throughput methylation analysis. 2006 Genome Research 12:158-164.

Gonzalgo and Jones, Rapid quantitation of methylation differences at specific sites using methylation-sensitive single nuclear primer extension. 1997 Nuc Acid Res, 25, 12.

Kalantari et al, Conserved Methylation Patterns of Human Papillomavirus Type 16 DNA in Asymptomatic Infection and Cervical Neoplasia, Journal of virology, December 2004, p. 12762-12772.

Kang et al, Inverse correlation between RASSF1A hypermethylation, KRAS and BRAF mutations in cervical adenocarcinoma, Gynecol Oncol 2007 June; 105(3):662-6. Epub 2007 Mar. 13.

Keating et al, Ki-67, Cyclin E and p16 (INK4A) are complementary surrogate biomarkers for human papillomavirus-related cervical neoplasia. Am J Surg Pathol 25, 884-891 (2001).

Kitkumthorn, N. et al. (2006) Cyclin A1 promoter hypermethylation in human papillomavirus-associated cervical cancer. *Bmc Cancer,* 6.

Koopman, L. A. et al. (1999) Recurrent integration of human papillomaviruses 16, 45, and 67 near translocation breakpoints in new cervical cancer cell lines. *Cancer Research,* 59, 5615-5624.

Kwoh D Y, Davis G R, Whitfield K M, Chappelle H L, DiMichele U, Gingeras T R. Transcription-based amplification system and detection of amplified human immunodeficiency virus type 1 with a bead-based sandwich hybridization format. Proc Natl Acad Sci USA. 1989 February; 86(4):1173-7.

Li K B. ClustalW-MPI: ClustalW analysis using distributed and parallel computing. Bioinformatics 2003; 19(12):1585-6.

Liu, G. et al. (2003) NetAffx: Affymetrix probesets and annotations. *Nucleic Acids Res.,* 31, 82-86.

Malinowski D. (2007) Multiple biomarkers in molecular oncology. Molecular diagnostics application in cervical cancer detection. *Expert Rev. Mol. Diagn.* 7(2), 117-131.

Rao et al., Chromosomal amplifications, 3q gain and deletions of 2q33-q37 are the frequent genetic changes in cervical carcinoma. BMC Cancer 4(1), 5 (2004).

Rebhan, M. et al. (1997) GeneCards: Integrating information about genes, proteins and diseases. *Trends in Genetics,* 13, 163.

Shiraisi, M. et al. Biol Chem. 1999, 380(9):1127-1131.

Straub, J. et al., A64-AACRMD (2007): Base5, a versatile, highly integrated high-throughput methylation profiling platform for Methylation-Specific PCR based marker identification applied to CRC.

Suzuki Y, Yamashita R, Sugano S, Nakai K. DBTSS, DataBase of Transcriptional Start Sites: progress report 2004. Nucleic Acids Res 2004; 32 (Database issue):D78-81.

Thomassin H. et al. MethylQuant: a sensitive method for quantifying methylation of specific cytosines within the genome. 2004. Nuc Acid Res 32, 21.

Thompson J D, Higgins D G, Gibson T J. CLUSTAL W: improving the sensitivity of progressive multiple sequence alignment through sequence weighting, position-specific gap penalties and weight matrix choice. Nucleic Acids Res 1994; 22(22):4673-80.

Tost, J. et al. Analysis and accurate quantification of CpG methylation by MALDI mass spectrometry. Nuc. Acid Res, 2003, 31(9): e50.

Trinh B. et al. DNA methylation analysis by MethyLight technology. Methods. 2001 December; 25(4).

Trooskens G, De Beule D, Decouttere F, Van Criekinge W. Phylogenetic trees: visualizing, customizing and detecting incongruence. Bioinformatics 2005; 21(19):3801-2.

van Dongen, J. J. et al. (2003) Design and standardization of PCR primers and protocols for detection of clonal immunoglobulin and T-cell receptor gene recombinations in suspect lymphoproliferations: report of the BIOMED-2 Concerted Action BMH4-CT98-3936. *Leukemia,* 17, 2257-2317.

Virmani et al. (2001) Aberrant methylation during cervical carcinogenesis. *Clin Cancer Research,* March; 7(3):584-9.

Xiong, Z. G. and Laird, P. W. (1997) COBRA: A sensitive and quantitative DNA methylation assay. *Nucleic Acids Research,* 25, 2532-2534.

Zeschnigk M. et al. A novel real-time PCR assay for quantitative analysis of methylated alleles (QAMA): analysis of the retinoblastoma locus. 2004. Nuc Acid Res 32, 16.

---

The invention claimed is:

1. A method for identifying, in a test sample, cervical cancer or its precursor, or predisposition to cervical cancer and performing screening or treating, said method comprising: providing a test sample comprising cervical cells or nucleic acids from cervical cells; detecting in said test sample methylation of at least one gene selected from the group consisting of EPB41L3, JAM3, and TERT by contacting at least a portion of the gene or promoter region thereof of the test sample with a chemical reagent that selectively modifies a non-methylated cytosine residue relative to a methylated cytosine residue, or selectively modifies a methylated cytosine residue relative to a non-methylated cytosine residue; and detecting a product generated due to said contacting, the product obtained by contacting at least a portion of the TERT gene or promoter region thereof comprising SEQ ID NO:384; wherein methylation in said test sample indicates the presence of cells that are neoplastic, precursor to neoplastic, or predisposed to neoplasia, or the presence of nucleic acids from cells that are neoplastic, precursor to neoplastic, or predisposed to neoplasia, wherein
   if the at least one gene is methylated, refer the woman for colposcopy; or
   if the at least one gene is unmethylated, refer the woman to screening for the presence of hr-HPV; or
   if the at least one gene is methylated, refer the woman for cervical resection.

2. The method of claim 1, further comprising detecting in said test sample the methylation of C13orf18.

3. The method according to claim 1, wherein the test sample comprises squamous cells, nucleic acids from squamous cells, adenocarcinoma cells, nucleic acids from adenocarcinoma cells, adenosquamous cell carcinoma cells, nucleic acids from adenosquamous carcinoma cells, or any combination thereof.

4. The method according to claim 1, wherein the test sample is from a specimen selected from the group consisting of a tissue specimen, a biopsy specimen, a surgical specimen, a cytological specimen, cervical scrapings, cervical smear, cervical washing, vaginal excretions, and blood.

5. The method of claim 4, wherein the test sample is from a biopsy specimen and surgical removal of neoplastic tissue is recommended to the patient.

6. The method of claim 4, wherein the specimen is a surgical specimen and adjuvant chemotherapy or adjuvant radiation therapy is recommended to the patient.

7. The method according to claim 1, wherein epigenetic modification of at least two genes is detected.

8. The method according to claim 1, wherein said methylation is at a CpG dinucleotide motif in the gene, or a promoter region thereof.

9. The method of claim 1, wherein the step of detecting a product employs amplification with at least one primer that hybridizes to a sequence comprising a modified non-methylated CpG dinucleotide motif but not to a sequence comprising an unmodified methylated CpG dinucleotide motif thereby forming amplification products.

10. The method of claim 1, wherein the step of detecting a product comprises amplification with at least one primer that hybridizes to a sequence comprising an unmodified methylated CpG dinucleotide motif but not to a sequence comprising a modified non-methylated CpG dinucleotide motif thereby forming amplification products.

11. The method of claim 1, wherein the product is detected by a method selected from the group consisting of electrophoresis, hybridization, amplification, sequencing, ligase chain reaction, chromatography, mass spectrometry, and combinations thereof.

12. The method of claim 1, wherein the chemical reagent comprises bisulfite ions.

13. The method of claim 12, further comprising treating the bisulfite ion-contacted, at least a portion of the gene with alkali.

14. The method according to claim 1, wherein the step of detecting employs amplification of at least a portion of the at least one gene using an oligonucleotide primer that specifically hybridizes under amplification conditions to a region of a gene selected from the group consisting of EPB41L3, JAM3, and TERT; wherein the region is within about 10 kb of said gene's transcription start site.

15. The method according to claim 1, wherein the step of detecting employs amplification of at least a portion of the at least one gene using at least one pair of oligonucleotide primers that specifically hybridizes under amplification conditions to a region of a gene selected from the group consisting of genes according to EPB41L3, JAM3, and TERT; wherein the region is within about 10 kb of said gene's transcription start site.

16. The method of claim 15, further comprising one pair of oligonucleotide primers that specifically hybridize under amplification conditions to C13orf18.

17. A method for identifying, in a test sample, cervical cancer or its precursor, or predisposition to cervical cancer and performing screening or treating, said method comprising: providing a test sample comprising cervical cells or nucleic acids from cervical cells; detecting in said test sample methylation of at least one gene selected from the group consisting of EPB41L3, JAM3, and TERT by contacting at least a portion of the gene or promoter region thereof of the test sample with a chemical reagent that selectively modifies a non-methylated cytosine residue relative to a methylated cytosine residue, or selectively modifies a methylated cytosine residue relative to a non-methylated cytosine residue; and detecting a product generated due to said contacting, the product comprising at least one of SEQ ID NO:309, SEQ ID NO:310, SEQ ID NO:331, and SEQ ID NO:384; wherein methylation in said test sample indicates the presence of cells that are neoplastic, precursor to neoplastic, or predisposed to neoplasia, or the presence of nucleic acids from cells that are neoplastic, precursor to neoplastic, or predisposed to neoplasia, wherein
   if the at least one gene is methylated, refer the woman for colposcopy; or
   if the at least one gene is unmethylated, refer the woman to screening for the presence of hr-HPV; or
   if the at least one gene is methylated, refer the woman for cervical resection.

18. The method of claim 17, further comprising detecting in said test sample the methylation of C13orf18.

19. The method of claim 17, wherein the test sample is from a biopsy specimen and surgical removal of neoplastic tissue is recommended to the patient.

20. The method of claim 17, wherein the specimen is a surgical specimen and adjuvant chemotherapy or adjuvant radiation therapy is recommended to the patient.

21. A method for identifying, in a test sample, cervical cancer or its precursor, or predisposition to cervical cancer and performing screening or treating, said method comprising: providing a test sample comprising cervical cells or nucleic acids from cervical cells; detecting in said test sample methylation of at least one gene selected from the group consisting of EPB41L3, JAM3, and TERT by contacting at least a portion of the gene or promoter region thereof of the test sample with a chemical reagent that selectively modifies a non-methylated cytosine residue relative to a methylated cytosine residue, or selectively modifies a methylated cytosine residue relative to a non-methylated cytosine residue; and detecting a product generated due to said contacting by amplifying the contacted portion and detecting an amplification product, the amplification product comprising at least one of SEQ ID NO:309, SEQ ID NO:310, SEQ ID NO:331, and SEQ ID NO:384; wherein methylation in said test sample indicates the presence of cells that are neoplastic, precursor to neoplastic, or predisposed to neoplasia, or the presence of nucleic acids from cells that are neoplastic, precursor to neoplastic, or predisposed to neoplasia, wherein
- if the at least one gene is methylated, refer the woman for colposcopy; or
- if the at least one gene is unmethylated, refer the woman to screening for the presence of hr-HPV; or
- if the at least one gene is methylated, refer the woman for cervical resection.

22. The method of claim 21, wherein the step of detecting a product comprises amplifying the contacted portion with at least one primer that hybridizes to a sequence comprising a modified non-methylated CpG dinucleotide motif but not to a sequence comprising an unmodified methylated CpG dinucleotide motif thereby forming amplification products.

23. The method of claim 21, wherein the step of detecting a product comprises amplifying the contacted portion with at least one primer that hybridizes to a sequence comprising an unmodified methylated CpG dinucleotide motif but not to a sequence comprising a modified non-methylated CpG dinucleotide motif thereby forming amplification products.

* * * * *

SEQUENCE LISTING

<160> NUMBER OF SEQ ID NOS: 449

<210> SEQ ID NO 1
<211> LENGTH: 19
<212> TYPE: DNA
<213> ORGANISM: artificial
<220> FEATURE:
<223> OTHER INFORMATION: primer

<400> SEQUENCE: 1
gtttggttcg ggttagcgt                                              19

<210> SEQ ID NO 2
<211> LENGTH: 22
<212> TYPE: DNA
<213> ORGANISM: artificial
<220> FEATURE:
<223> OTHER INFORMATION: primer

<400> SEQUENCE: 2
ttgcgtttta tttgtatttc gc                                          22

<210> SEQ ID NO 3
<211> LENGTH: 21
<212> TYPE: DNA
<213> ORGANISM: artificial
<220> FEATURE:
<223> OTHER INFORMATION: primer

<400> SEQUENCE: 3
ttttattgcg agtcgtcggt c                                           21

<210> SEQ ID NO 4
<211> LENGTH: 23
<212> TYPE: DNA
<213> ORGANISM: artificial
<220> FEATURE:
<223> OTHER INFORMATION: primer

<400> SEQUENCE: 4
tgtataggag tcgaagggac gta                                         23

<210> SEQ ID NO 5
<211> LENGTH: 21
<212> TYPE: DNA
<213> ORGANISM: artificial
<220> FEATURE:
<223> OTHER INFORMATION: primer

<400> SEQUENCE: 5
gttaggtaag tggtacggcg a                                           21

```
<210> SEQ ID NO 6
<211> LENGTH: 23
<212> TYPE: DNA
<213> ORGANISM: artificial
<220> FEATURE:
<223> OTHER INFORMATION: primer

<400> SEQUENCE: 6
atttaatgag acggtaggt agc                                            23

<210> SEQ ID NO 7
<211> LENGTH: 25
<212> TYPE: DNA
<213> ORGANISM: artificial
<220> FEATURE:
<223> OTHER INFORMATION: primer

<400> SEQUENCE: 7
tttaatataa gtcgggttac gttcg                                         25

<210> SEQ ID NO 8
<211> LENGTH: 21
<212> TYPE: DNA
<213> ORGANISM: artificial
<220> FEATURE:
<223> OTHER INFORMATION: primer

<400> SEQUENCE: 8
ttagggagta agtgcgtttg c                                             21

<210> SEQ ID NO 9
<211> LENGTH: 23
<212> TYPE: DNA
<213> ORGANISM: artificial
<220> FEATURE:
<223> OTHER INFORMATION: primer

<400> SEQUENCE: 9
tagacggtta cgagtaggcg gta                                           23

<210> SEQ ID NO 10
<211> LENGTH: 23
<212> TYPE: DNA
<213> ORGANISM: artificial
<220> FEATURE:
<223> OTHER INFORMATION: primer

<400> SEQUENCE: 10
tttttcgtat tttaggaagt ggc                                           23

<210> SEQ ID NO 11
<211> LENGTH: 21
<212> TYPE: DNA
<213> ORGANISM: artificial
<220> FEATURE:
<223> OTHER INFORMATION: primer

<400> SEQUENCE: 11
tttggggttc gattatattt c                                             21

<210> SEQ ID NO 12
<211> LENGTH: 19
<212> TYPE: DNA
<213> ORGANISM: artificial
<220> FEATURE:
```

```
<223> OTHER INFORMATION: primer

<400> SEQUENCE: 12
gttatttttc ggcgggttc                                                19

<210> SEQ ID NO 13
<211> LENGTH: 21
<212> TYPE: DNA
<213> ORGANISM: artificial
<220> FEATURE:
<223> OTHER INFORMATION: primer

<400> SEQUENCE: 13
tacgcgtagg ttttaagtcg c                                             21

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
tttgattttt gaaagcgtcg t                                             21

<210> SEQ ID NO 15
<211> LENGTH: 22
<212> TYPE: DNA
<213> ORGANISM: artificial
<220> FEATURE:
<223> OTHER INFORMATION: primer

<400> SEQUENCE: 15
tttttaggga agtaaagcgt cg                                            22

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
tagtttggta gttagcgggt c                                             21

<210> SEQ ID NO 17
<211> LENGTH: 19
<212> TYPE: DNA
<213> ORGANISM: artificial
<220> FEATURE:
<223> OTHER INFORMATION: primer

<400> SEQUENCE: 17 ataggggag ttcggtacg                                                 19

<210> SEQ ID NO 18
<211> LENGTH: 25
<212> TYPE: DNA
<213> ORGANISM: artificial
<220> FEATURE:
<223> OTHER INFORMATION: primer

<400> SEQUENCE: 18
cgtttttata gggttttggt tggac                                         25
```

```
<210> SEQ ID NO 19
<211> LENGTH: 23
<212> TYPE: DNA
<213> ORGANISM: artificial
<220> FEATURE:
<223> OTHER INFORMATION: primer

<400> SEQUENCE: 19
tagttgtatc ggtttaggcg ttt                                           23

<210> SEQ ID NO 20
<211> LENGTH: 19
<212> TYPE: DNA
<213> ORGANISM: artificial
<220> FEATURE:
<223> OTHER INFORMATION: primer

<400> SEQUENCE: 20
gttatggcga tgcggtttc                                                19

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
gaaggtagcg ttttcgatg                                                20

<210> SEQ ID NO 22
<211> LENGTH: 24
<212> TYPE: DNA
<213> ORGANISM: artificial
<220> FEATURE:
<223> OTHER INFORMATION: primer

<400> SEQUENCE: 22
aattttaggt tagagggtta tcgc                                          24

<210> SEQ ID NO 23
<211> LENGTH: 19
<212> TYPE: DNA
<213> ORGANISM: artificial
<220> FEATURE:
<223> OTHER INFORMATION: primer

<400> SEQUENCE: 23 gaggggtag gaaagtcgc                                                 19

<210> SEQ ID NO 24
<211> LENGTH: 20
<212> TYPE: DNA
<213> ORGANISM: artificial
<220> FEATURE:
<223> OTHER INFORMATION: primer

<400> SEQUENCE: 24
gggacgattt ttcgttgttc                                               20

<210> SEQ ID NO 25
<211> LENGTH: 23
<212> TYPE: DNA
<213> ORGANISM: artificial
<220> FEATURE:
<223> OTHER INFORMATION: primer
```

```
<400> SEQUENCE: 25
aatttcgttt gtagagtcgt cgt                                              23

<210> SEQ ID NO 26
<211> LENGTH: 20
<212> TYPE: DNA
<213> ORGANISM: artificial
<220> FEATURE:
<223> OTHER INFORMATION: primer

<400> SEQUENCE: 26
gtcggtaagg tttggagagc                                                  20

<210> SEQ ID NO 27
<211> LENGTH: 23
<212> TYPE: DNA
<213> ORGANISM: artificial
<220> FEATURE:
<223> OTHER INFORMATION: primer

<400> SEQUENCE: 27
ttagaagtaa tttaggcgcg ttc                                              23

<210> SEQ ID NO 28
<211> LENGTH: 23
<212> TYPE: DNA
<213> ORGANISM: artificial
<220> FEATURE:
<223> OTHER INFORMATION: primer

<400> SEQUENCE: 28
aatttgattt gtgtgtgtat cgc                                              23

<210> SEQ ID NO 29
<211> LENGTH: 20
<212> TYPE: DNA
<213> ORGANISM: artificial
<220> FEATURE:
<223> OTHER INFORMATION: primer

<400> SEQUENCE: 29
gtttacgcga tttttgggac                                                  20

<210> SEQ ID NO 30
<211> LENGTH: 19
<212> TYPE: DNA
<213> ORGANISM: artificial
<220> FEATURE:
<223> OTHER INFORMATION: primer

<400> SEQUENCE: 30
agggtttttc ggagtcgtt                                                   19

<210> SEQ ID NO 31
<211> LENGTH: 22
<212> TYPE: DNA
<213> ORGANISM: artificial
<220> FEATURE:
<223> OTHER INFORMATION: primer

<400> SEQUENCE: 31
aggcgtcgta tttatagcgt tt                                               22

<210> SEQ ID NO 32
<211> LENGTH: 20
```

```
<212> TYPE: DNA
<213> ORGANISM: artificial
<220> FEATURE:
<223> OTHER INFORMATION: primer

<400> SEQUENCE: 32 gtggggtcg gtgtagtatc                                              20

<210> SEQ ID NO 33
<211> LENGTH: 23
<212> TYPE: DNA
<213> ORGANISM: artificial
<220> FEATURE:
<223> OTHER INFORMATION: primer

<400> SEQUENCE: 33
tataaaaggg gttcgggtta gtc                                         23

<210> SEQ ID NO 34
<211> LENGTH: 25
<212> TYPE: DNA
<213> ORGANISM: artificial
<220> FEATURE:
<223> OTHER INFORMATION: primer

<400> SEQUENCE: 34
aggaagtatt tattgcgtat gtttc                                       25

<210> SEQ ID NO 35
<211> LENGTH: 23
<212> TYPE: DNA
<213> ORGANISM: artificial
<220> FEATURE:
<223> OTHER INFORMATION: primer

<400> SEQUENCE: 35
taattttaag gaggacgagg gtc                                         23

<210> SEQ ID NO 36
<211> LENGTH: 19
<212> TYPE: DNA
<213> ORGANISM: artificial
<220> FEATURE:
<223> OTHER INFORMATION: primer

<400> SEQUENCE: 36
gttttgggag aggcggttc                                              19

<210> SEQ ID NO 37
<211> LENGTH: 21
<212> TYPE: DNA
<213> ORGANISM: artificial
<220> FEATURE:
<223> OTHER INFORMATION: primer

<400> SEQUENCE: 37
ggtgtagcgt ttagggtcgt c                                           21

<210> SEQ ID NO 38
<211> LENGTH: 24
<212> TYPE: DNA
<213> ORGANISM: artificial
<220> FEATURE:
<223> OTHER INFORMATION: primer

<400> SEQUENCE: 38
```

```
ggatagtcgg atcgagttaa cgtc                                          24

<210> SEQ ID NO 39
<211> LENGTH: 24
<212> TYPE: DNA
<213> ORGANISM: artificial
<220> FEATURE:
<223> OTHER INFORMATION: primer

<400> SEQUENCE: 39
aggataggta tgaatttcgg tttc                                          24

<210> SEQ ID NO 40
<211> LENGTH: 23
<212> TYPE: DNA
<213> ORGANISM: artificial
<220> FEATURE:
<223> OTHER INFORMATION: primer

<400> SEQUENCE: 40
cgggtttgag ggtaatagaa tcg                                           23

<210> SEQ ID NO 41
<211> LENGTH: 19
<212> TYPE: DNA
<213> ORGANISM: artificial
<220> FEATURE:
<223> OTHER INFORMATION: primer

<400> SEQUENCE: 41
gtgcggggta agaaggaac                                                19

<210> SEQ ID NO 42
<211> LENGTH: 20
<212> TYPE: DNA
<213> ORGANISM: artificial
<220> FEATURE:
<223> OTHER INFORMATION: primer

<400> SEQUENCE: 42
gagagagaaa gcgggagttc                                               20

<210> SEQ ID NO 43
<211> LENGTH: 19
<212> TYPE: DNA
<213> ORGANISM: artificial
<220> FEATURE:
<223> OTHER INFORMATION: primer

<400> SEQUENCE: 43
taggagcgtt gtttcggtc                                                19

<210> SEQ ID NO 44
<211> LENGTH: 23
<212> TYPE: DNA
<213> ORGANISM: artificial
<220> FEATURE:
<223> OTHER INFORMATION: primer

<400> SEQUENCE: 44
tttaggtggg aagcgtattt atc                                           23

<210> SEQ ID NO 45
<211> LENGTH: 19
<212> TYPE: DNA
<213> ORGANISM: artificial
```

-continued

```
<220> FEATURE:
<223> OTHER INFORMATION: primer

<400> SEQUENCE: 45
gggatagtgg ggttgacgc                                              19

<210> SEQ ID NO 46
<211> LENGTH: 19
<212> TYPE: DNA
<213> ORGANISM: artificial
<220> FEATURE:
<223> OTHER INFORMATION: primer

<400> SEQUENCE: 46
gcgtgggttt tcgtcgtag                                              19

<210> SEQ ID NO 47
<211> LENGTH: 22
<212> TYPE: DNA
<213> ORGANISM: artificial
<220> FEATURE:
<223> OTHER INFORMATION: primer

<400> SEQUENCE: 47
cgggttgtag ttaatatcga gg                                          22

<210> SEQ ID NO 48
<211> LENGTH: 22
<212> TYPE: DNA
<213> ORGANISM: artificial
<220> FEATURE:
<223> OTHER INFORMATION: primer

<400> SEQUENCE: 48
tttgttcgtt tttcgattgt tc                                          22

<210> SEQ ID NO 49
<211> LENGTH: 21
<212> TYPE: DNA
<213> ORGANISM: artificial
<220> FEATURE:
<223> OTHER INFORMATION: primer

<400> SEQUENCE: 49
cgttaatcgg ataagagtgc g                                           21

<210> SEQ ID NO 50
<211> LENGTH: 26
<212> TYPE: DNA
<213> ORGANISM: artificial
<220> FEATURE:
<223> OTHER INFORMATION: primer

<400> SEQUENCE: 50
gtatagtttc gtagtttgcg tttagc                                      26

<210> SEQ ID NO 51
<211> LENGTH: 22
<212> TYPE: DNA
<213> ORGANISM: artificial
<220> FEATURE:
<223> OTHER INFORMATION: primer

<400> SEQUENCE: 51
ggtattgtta ttttgcgttt tc                                          22
```

```
<210> SEQ ID NO 52
<211> LENGTH: 19
<212> TYPE: DNA
<213> ORGANISM: artificial
<220> FEATURE:
<223> OTHER INFORMATION: primer

<400> SEQUENCE: 52
gatttcgggt tgttatggc                                                19

<210> SEQ ID NO 53
<211> LENGTH: 19
<212> TYPE: DNA
<213> ORGANISM: artificial
<220> FEATURE:
<223> OTHER INFORMATION: primer

<400> SEQUENCE: 53
gaaagaagga ggtttcggc                                                19

<210> SEQ ID NO 54
<211> LENGTH: 24
<212> TYPE: DNA
<213> ORGANISM: artificial
<220> FEATURE:
<223> OTHER INFORMATION: primer

<400> SEQUENCE: 54
gttgtgagtt gcgttttta cgtc                                           24

<210> SEQ ID NO 55
<211> LENGTH: 19
<212> TYPE: DNA
<213> ORGANISM: artificial
<220> FEATURE:
<223> OTHER INFORMATION: primer

<400> SEQUENCE: 55
ggtcgtagtc gtagtcggg                                                19

<210> SEQ ID NO 56
<211> LENGTH: 23
<212> TYPE: DNA
<213> ORGANISM: artificial
<220> FEATURE:
<223> OTHER INFORMATION: primer

<400> SEQUENCE: 56
gaatttggta cgattttacg gag                                           23

<210> SEQ ID NO 57
<211> LENGTH: 20
<212> TYPE: DNA
<213> ORGANISM: artificial
<220> FEATURE:
<223> OTHER INFORMATION: primer

<400> SEQUENCE: 57
atttagtatt ggggcggagc                                               20

<210> SEQ ID NO 58
<211> LENGTH: 23
<212> TYPE: DNA
<213> ORGANISM: artificial
<220> FEATURE:
<223> OTHER INFORMATION: primer
```

```
<400> SEQUENCE: 58
agtagtagga atagaaacgg cga                                          23

<210> SEQ ID NO 59
<211> LENGTH: 21
<212> TYPE: DNA
<213> ORGANISM: artificial
<220> FEATURE:
<223> OTHER INFORMATION: primer

<400> SEQUENCE: 59
gaagttggtt agggtacggt c                                            21

<210> SEQ ID NO 60
<211> LENGTH: 20
<212> TYPE: DNA
<213> ORGANISM: artificial
<220> FEATURE:
<223> OTHER INFORMATION: primer

<400> SEQUENCE: 60
ggatcgttgg attttggttc                                              20

<210> SEQ ID NO 61
<211> LENGTH: 23
<212> TYPE: DNA
<213> ORGANISM: artificial
<220> FEATURE:
<223> OTHER INFORMATION: primer

<400> SEQUENCE: 61
tttttagagt aaatagcggg agc                                          23

<210> SEQ ID NO 62
<211> LENGTH: 22
<212> TYPE: DNA
<213> ORGANISM: artificial
<220> FEATURE:
<223> OTHER INFORMATION: primer

<400> SEQUENCE: 62
ttttatttat tcggggagtt gc                                           22

<210> SEQ ID NO 63
<211> LENGTH: 21
<212> TYPE: DNA
<213> ORGANISM: artificial
<220> FEATURE:
<223> OTHER INFORMATION: primer

<400> SEQUENCE: 63
tcgtagggtt cgtagtcgtt t                                            21

<210> SEQ ID NO 64
<211> LENGTH: 25
<212> TYPE: DNA
<213> ORGANISM: artificial
<220> FEATURE:
<223> OTHER INFORMATION: primer

<400> SEQUENCE: 64
gtcggttgac gttttgagat aagtc                                        25

<210> SEQ ID NO 65
```

```
<211> LENGTH: 22
<212> TYPE: DNA
<213> ORGANISM: artificial
<220> FEATURE:
<223> OTHER INFORMATION: primer

<400> SEQUENCE: 65
tcggatttcg tttttagcgt at                                              22

<210> SEQ ID NO 66
<211> LENGTH: 21
<212> TYPE: DNA
<213> ORGANISM: artificial
<220> FEATURE:
<223> OTHER INFORMATION: primer

<400> SEQUENCE: 66
taggttggtt tggtttcggt c                                               21

<210> SEQ ID NO 67
<211> LENGTH: 20
<212> TYPE: DNA
<213> ORGANISM: artificial
<220> FEATURE:
<223> OTHER INFORMATION: primer

<400> SEQUENCE: 67
gggattataa gtcgcgtcgc                                                 20

<210> SEQ ID NO 68
<211> LENGTH: 24
<212> TYPE: DNA
<213> ORGANISM: artificial
<220> FEATURE:
<223> OTHER INFORMATION: primer

<400> SEQUENCE: 68
ttagatttcg taaacggtga aaac                                            24

<210> SEQ ID NO 69
<211> LENGTH: 25
<212> TYPE: DNA
<213> ORGANISM: artificial
<220> FEATURE:
<223> OTHER INFORMATION: primer

<400> SEQUENCE: 69
tggatggagt ttaggttata tcgtc                                           25

<210> SEQ ID NO 70
<211> LENGTH: 21
<212> TYPE: DNA
<213> ORGANISM: artificial
<220> FEATURE:
<223> OTHER INFORMATION: primer

<400> SEQUENCE: 70
aggagggatt gtcggattta c                                               21

<210> SEQ ID NO 71
<211> LENGTH: 22
<212> TYPE: DNA
<213> ORGANISM: artificial
<220> FEATURE:
<223> OTHER INFORMATION: primer

<400> SEQUENCE: 71
```

```
tttttagatt tatcgagtgg cg                                    22

<210> SEQ ID NO 72
<211> LENGTH: 21
<212> TYPE: DNA
<213> ORGANISM: artificial
<220> FEATURE:
<223> OTHER INFORMATION: primer

<400> SEQUENCE: 72
cggtatcgtt gtttaggagg c                                     21

<210> SEQ ID NO 73
<211> LENGTH: 20
<212> TYPE: DNA
<213> ORGANISM: artificial
<220> FEATURE:
<223> OTHER INFORMATION: primer

<400> SEQUENCE: 73
agttgtttgg tattcgcggt                                       20

<210> SEQ ID NO 74
<211> LENGTH: 22
<212> TYPE: DNA
<213> ORGANISM: artificial
<220> FEATURE:
<223> OTHER INFORMATION: primer

<400> SEQUENCE: 74
gttagattga tttcgttcga gg                                    22

<210> SEQ ID NO 75
<211> LENGTH: 25
<212> TYPE: DNA
<213> ORGANISM: artificial
<220> FEATURE:
<223> OTHER INFORMATION: primer

<400> SEQUENCE: 75
tagtagattt ttagcggtga agacg                                 25

<210> SEQ ID NO 76
<211> LENGTH: 24
<212> TYPE: DNA
<213> ORGANISM: artificial
<220> FEATURE:
<223> OTHER INFORMATION: primer

<400> SEQUENCE: 76
ttcgggtttt tttgttttta attc                                  24

<210> SEQ ID NO 77
<211> LENGTH: 22
<212> TYPE: DNA
<213> ORGANISM: artificial
<220> FEATURE:
<223> OTHER INFORMATION: primer

<400> SEQUENCE: 77
gtaagtgagt ttcgagtgtc gc                                    22

<210> SEQ ID NO 78
<211> LENGTH: 21
<212> TYPE: DNA
```

<213> ORGANISM: artificial
<220> FEATURE:
<223> OTHER INFORMATION: primer

<400> SEQUENCE: 78
gaaaggtcgg atttgttttt c                                              21

<210> SEQ ID NO 79
<211> LENGTH: 21
<212> TYPE: DNA
<213> ORGANISM: artificial
<220> FEATURE:
<223> OTHER INFORMATION: primer

<400> SEQUENCE: 79
agattttgtg gtttcgtcgt t                                              21

<210> SEQ ID NO 80
<211> LENGTH: 25
<212> TYPE: DNA
<213> ORGANISM: artificial
<220> FEATURE:
<223> OTHER INFORMATION: primer

<400> SEQUENCE: 80
gcggttttta aggagtttta ttttc                                          25

<210> SEQ ID NO 81
<211> LENGTH: 19
<212> TYPE: DNA
<213> ORGANISM: artificial
<220> FEATURE:
<223> OTHER INFORMATION: primer

<400> SEQUENCE: 81
gagagattcg ggattcgtg                                                 19

<210> SEQ ID NO 82
<211> LENGTH: 23
<212> TYPE: DNA
<213> ORGANISM: artificial
<220> FEATURE:
<223> OTHER INFORMATION: primer

<400> SEQUENCE: 82
agtacgttgt ttcggagttt ttc                                            23

<210> SEQ ID NO 83
<211> LENGTH: 21
<212> TYPE: DNA
<213> ORGANISM: artificial
<220> FEATURE:
<223> OTHER INFORMATION: primer

<400> SEQUENCE: 83
gcgtcgtttt gtatgggtat c                                              21

<210> SEQ ID NO 84
<211> LENGTH: 20
<212> TYPE: DNA
<213> ORGANISM: artificial
<220> FEATURE:
<223> OTHER INFORMATION: primer

<400> SEQUENCE: 84
cgagtagtag ttgcgtcggg                                                20

<210> SEQ ID NO 85
<211> LENGTH: 22
<212> TYPE: DNA
<213> ORGANISM: artificial
<220> FEATURE:
<223> OTHER INFORMATION: primer

<400> SEQUENCE: 85
tgtatgattt tagttcgcgg at                                            22

<210> SEQ ID NO 86
<211> LENGTH: 21
<212> TYPE: DNA
<213> ORGANISM: artificial
<220> FEATURE:
<223> OTHER INFORMATION: primer

<400> SEQUENCE: 86
gcgggattta tttgttacgg a                                             21

<210> SEQ ID NO 87
<211> LENGTH: 20
<212> TYPE: DNA
<213> ORGANISM: artificial
<220> FEATURE:
<223> OTHER INFORMATION: primer

<400> SEQUENCE: 87
attgcgtcgg gtttagtttc                                               20

<210> SEQ ID NO 88
<211> LENGTH: 19
<212> TYPE: DNA
<213> ORGANISM: artificial
<220> FEATURE:
<223> OTHER INFORMATION: primer

<400> SEQUENCE: 88
gtttagggaa agcggacga                                                19

<210> SEQ ID NO 89
<211> LENGTH: 19
<212> TYPE: DNA
<213> ORGANISM: artificial
<220> FEATURE:
<223> OTHER INFORMATION: primer

<400> SEQUENCE: 89
gttcgtagtt cggggcgtt                                                19

<210> SEQ ID NO 90
<211> LENGTH: 19
<212> TYPE: DNA
<213> ORGANISM: artificial
<220> FEATURE:
<223> OTHER INFORMATION: primer

<400> SEQUENCE: 90
ttattttgcg agcggtttc                                                19

<210> SEQ ID NO 91
<211> LENGTH: 25
<212> TYPE: DNA
<213> ORGANISM: artificial
<220> FEATURE:

<223> OTHER INFORMATION: primer

<400> SEQUENCE: 91
gatttgggcg tttttggttt ttcgc                                              25

<210> SEQ ID NO 92
<211> LENGTH: 23
<212> TYPE: DNA
<213> ORGANISM: artificial
<220> FEATURE:
<223> OTHER INFORMATION: primer

<400> SEQUENCE: 92
gtgggtttta agtttacggt ttc                                                23

<210> SEQ ID NO 93
<211> LENGTH: 20
<212> TYPE: DNA
<213> ORGANISM: artificial
<220> FEATURE:
<223> OTHER INFORMATION: primer

<400> SEQUENCE: 93
ggcggagttt gtatagaggc                                                    20

<210> SEQ ID NO 94
<211> LENGTH: 20
<212> TYPE: DNA
<213> ORGANISM: artificial
<220> FEATURE:
<223> OTHER INFORMATION: primer

<400> SEQUENCE: 94
tttttgggtt tcgttgtttc                                                    20

<210> SEQ ID NO 95
<211> LENGTH: 23
<212> TYPE: DNA
<213> ORGANISM: artificial
<220> FEATURE:
<223> OTHER INFORMATION: primer

<400> SEQUENCE: 95
ttcgtttcgt ttaggtatcg ttt                                                23

<210> SEQ ID NO 96
<211> LENGTH: 23
<212> TYPE: DNA
<213> ORGANISM: artificial
<220> FEATURE:
<223> OTHER INFORMATION: primer

<400> SEQUENCE: 96
tttaggatta tagtgagcga cgg                                                23

<210> SEQ ID NO 97
<211> LENGTH: 18
<212> TYPE: DNA
<213> ORGANISM: artificial
<220> FEATURE:
<223> OTHER INFORMATION: primer

<400> SEQUENCE: 97
gcgttgaagt cggggttc                                                      18

```
<210> SEQ ID NO 98
<211> LENGTH: 22
<212> TYPE: DNA
<213> ORGANISM: artificial
<220> FEATURE:
<223> OTHER INFORMATION: primer

<400> SEQUENCE: 98
ggtcgtttcg ttgtttttata gc                                           22

<210> SEQ ID NO 99
<211> LENGTH: 25
<212> TYPE: DNA
<213> ORGANISM: artificial
<220> FEATURE:
<223> OTHER INFORMATION: primer

<400> SEQUENCE: 99
ttacggttag tagaaggagt agcgt                                         25

<210> SEQ ID NO 100
<211> LENGTH: 21
<212> TYPE: DNA
<213> ORGANISM: artificial
<220> FEATURE:
<223> OTHER INFORMATION: primer

<400> SEQUENCE: 100
tcgaggaaga agatgtcgaa g                                             21

<210> SEQ ID NO 101
<211> LENGTH: 19
<212> TYPE: DNA
<213> ORGANISM: artificial
<220> FEATURE:
<223> OTHER INFORMATION: primer

<400> SEQUENCE: 101
gaggcgtaag taggcgaaa                                                19

<210> SEQ ID NO 102
<211> LENGTH: 19
<212> TYPE: DNA
<213> ORGANISM: artificial
<220> FEATURE:
<223> OTHER INFORMATION: primer

<400> SEQUENCE: 102
gattagagcg agcgaacga                                                19

<210> SEQ ID NO 103
<211> LENGTH: 21
<212> TYPE: DNA
<213> ORGANISM: artificial
<220> FEATURE:
<223> OTHER INFORMATION: primer

<400> SEQUENCE: 103
ggtttgttgg tcgttttag c                                              21

<210> SEQ ID NO 104
<211> LENGTH: 20
<212> TYPE: DNA
<213> ORGANISM: artificial
<220> FEATURE:
<223> OTHER INFORMATION: primer
```

<400> SEQUENCE: 104
gtatttaggg tagcgggtcg                                                    20

<210> SEQ ID NO 105
<211> LENGTH: 23
<212> TYPE: DNA
<213> ORGANISM: artificial
<220> FEATURE:
<223> OTHER INFORMATION: primer

<400> SEQUENCE: 105
gcgttatggt gtttttatag cgt                                                23

<210> SEQ ID NO 106
<211> LENGTH: 21
<212> TYPE: DNA
<213> ORGANISM: artificial
<220> FEATURE:
<223> OTHER INFORMATION: primer

<400> SEQUENCE: 106
ttgtaggcgg tttgtagtcg t                                                  21

<210> SEQ ID NO 107
<211> LENGTH: 19
<212> TYPE: DNA
<213> ORGANISM: artificial
<220> FEATURE:
<223> OTHER INFORMATION: primer

<400> SEQUENCE: 107
gaggatcggt ttaggttgc                                                     19

<210> SEQ ID NO 108
<211> LENGTH: 19
<212> TYPE: DNA
<213> ORGANISM: artificial
<220> FEATURE:
<223> OTHER INFORMATION: primer

<400> SEQUENCE: 108
aggggaagac gaagagcgt                                                     19

<210> SEQ ID NO 109
<211> LENGTH: 20
<212> TYPE: DNA
<213> ORGANISM: artificial
<220> FEATURE:
<223> OTHER INFORMATION: primer

<400> SEQUENCE: 109
tagcggagag gagattacgc                                                    20

<210> SEQ ID NO 110
<211> LENGTH: 23
<212> TYPE: DNA
<213> ORGANISM: artificial
<220> FEATURE:
<223> OTHER INFORMATION: primer

<400> SEQUENCE: 110
aggggtattt ataggcgttt agc                                                23

<210> SEQ ID NO 111
<211> LENGTH: 21

```
<212> TYPE: DNA
<213> ORGANISM: artificial
<220> FEATURE:
<223> OTHER INFORMATION: primer

<400> SEQUENCE: 111
gaagggtaat cgggtgtttt c                                         21

<210> SEQ ID NO 112
<211> LENGTH: 20
<212> TYPE: DNA
<213> ORGANISM: artificial
<220> FEATURE:
<223> OTHER INFORMATION: primer

<400> SEQUENCE: 112
gatagggttt tgttttcggc                                           20

<210> SEQ ID NO 113
<211> LENGTH: 23
<212> TYPE: DNA
<213> ORGANISM: artificial
<220> FEATURE:
<223> OTHER INFORMATION: primer

<400> SEQUENCE: 113
ttgtagtttt cgagttggag gtc                                       23

<210> SEQ ID NO 114
<211> LENGTH: 21
<212> TYPE: DNA
<213> ORGANISM: artificial
<220> FEATURE:
<223> OTHER INFORMATION: primer

<400> SEQUENCE: 114
gttaggagtt cgtcggttag c                                         21

<210> SEQ ID NO 115
<211> LENGTH: 19
<212> TYPE: DNA
<213> ORGANISM: artificial
<220> FEATURE:
<223> OTHER INFORMATION: primer

<400> SEQUENCE: 115
gagatgtttc gagggttgc                                            19

<210> SEQ ID NO 116
<211> LENGTH: 23
<212> TYPE: DNA
<213> ORGANISM: artificial
<220> FEATURE:
<223> OTHER INFORMATION: primer

<400> SEQUENCE: 116
tttcgcggtt ttttagattg ttc                                       23

<210> SEQ ID NO 117
<211> LENGTH: 20
<212> TYPE: DNA
<213> ORGANISM: artificial
<220> FEATURE:
<223> OTHER INFORMATION: primer

<400> SEQUENCE: 117
```

```
atcgtaggtt gggtttggtc                                           20

<210> SEQ ID NO 118
<211> LENGTH: 21
<212> TYPE: DNA
<213> ORGANISM: artificial
<220> FEATURE:
<223> OTHER INFORMATION: primer

<400> SEQUENCE: 118
tggttgcgtt gtttatcgtt t                                         21

<210> SEQ ID NO 119
<211> LENGTH: 20
<212> TYPE: DNA
<213> ORGANISM: artificial
<220> FEATURE:
<223> OTHER INFORMATION: primer

<400> SEQUENCE: 119
gggtatttat tgcgacggat                                           20

<210> SEQ ID NO 120
<211> LENGTH: 23
<212> TYPE: DNA
<213> ORGANISM: artificial
<220> FEATURE:
<223> OTHER INFORMATION: primer

<400> SEQUENCE: 120
ggtttcgata gcgtagttgt ttc                                       23

<210> SEQ ID NO 121
<211> LENGTH: 20
<212> TYPE: DNA
<213> ORGANISM: artificial
<220> FEATURE:
<223> OTHER INFORMATION: primer

<400> SEQUENCE: 121
gttcgttggg taaggcgttc                                           20

<210> SEQ ID NO 122
<211> LENGTH: 23
<212> TYPE: DNA
<213> ORGANISM: artificial
<220> FEATURE:
<223> OTHER INFORMATION: primer

<400> SEQUENCE: 122
taaggaattt tgtattcgga ggc                                       23

<210> SEQ ID NO 123
<211> LENGTH: 20
<212> TYPE: DNA
<213> ORGANISM: artificial
<220> FEATURE:
<223> OTHER INFORMATION: primer

<400> SEQUENCE: 123
gtggttagcg gatttcgagt                                           20

<210> SEQ ID NO 124
<211> LENGTH: 19
<212> TYPE: DNA
<213> ORGANISM: artificial
```

```
<220> FEATURE:
<223> OTHER INFORMATION: primer

<400> SEQUENCE: 124
tttcgtaggg ttcggtgtc                                                19

<210> SEQ ID NO 125
<211> LENGTH: 22
<212> TYPE: DNA
<213> ORGANISM: artificial
<220> FEATURE:
<223> OTHER INFORMATION: primer

<400> SEQUENCE: 125
gttagggttc gggggcgttg tt                                            22

<210> SEQ ID NO 126
<211> LENGTH: 23
<212> TYPE: DNA
<213> ORGANISM: artificial
<220> FEATURE:
<223> OTHER INFORMATION: primer

<400> SEQUENCE: 126
tttagttcgt tagtttcgtc ggt                                           23

<210> SEQ ID NO 127
<211> LENGTH: 19
<212> TYPE: DNA
<213> ORGANISM: artificial
<220> FEATURE:
<223> OTHER INFORMATION: primer

<400> SEQUENCE: 127
ttttgtggtt agtcgcggt                                                19

<210> SEQ ID NO 128
<211> LENGTH: 22
<212> TYPE: DNA
<213> ORGANISM: artificial
<220> FEATURE:
<223> OTHER INFORMATION: primer

<400> SEQUENCE: 128
gcgtcgttag atattttgtt gc                                            22

<210> SEQ ID NO 129
<211> LENGTH: 19
<212> TYPE: DNA
<213> ORGANISM: artificial
<220> FEATURE:
<223> OTHER INFORMATION: primer

<400> SEQUENCE: 129
gtatggagcg ttttgcgat                                                19

<210> SEQ ID NO 130
<211> LENGTH: 25
<212> TYPE: DNA
<213> ORGANISM: artificial
<220> FEATURE:
<223> OTHER INFORMATION: primer

<400> SEQUENCE: 130
tgtgttatat cggttagttg agagc                                         25
```

<210> SEQ ID NO 131
<211> LENGTH: 22
<212> TYPE: DNA
<213> ORGANISM: artificial
<220> FEATURE:
<223> OTHER INFORMATION: primer

<400> SEQUENCE: 131
cgtttgtttt tataggttcg gg                                              22

<210> SEQ ID NO 132
<211> LENGTH: 20
<212> TYPE: DNA
<213> ORGANISM: artificial
<220> FEATURE:
<223> OTHER INFORMATION: primer

<400> SEQUENCE: 132
tgtatgcgga gaggtcgtag                                                 20

<210> SEQ ID NO 133
<211> LENGTH: 21
<212> TYPE: DNA
<213> ORGANISM: artificial
<220> FEATURE:
<223> OTHER INFORMATION: primer

<400> SEQUENCE: 133
cctacttatc tctcccgctc g                                               21

<210> SEQ ID NO 134
<211> LENGTH: 23
<212> TYPE: DNA
<213> ORGANISM: artificial
<220> FEATURE:
<223> OTHER INFORMATION: primer

<400> SEQUENCE: 134
cttaacgaac gacttaaccg act                                             23

<210> SEQ ID NO 135
<211> LENGTH: 22
<212> TYPE: DNA
<213> ORGANISM: artificial
<220> FEATURE:
<223> OTHER INFORMATION: primer

<400> SEQUENCE: 135
tataccgaac ttatcgcctc cg                                              22

<210> SEQ ID NO 136
<211> LENGTH: 19
<212> TYPE: DNA
<213> ORGANISM: artificial
<220> FEATURE:
<223> OTHER INFORMATION: primer

<400> SEQUENCE: 136
aaacaactcc gaacgacga                                                  19

<210> SEQ ID NO 137
<211> LENGTH: 23
<212> TYPE: DNA
<213> ORGANISM: artificial
<220> FEATURE:
<223> OTHER INFORMATION: primer

```
<400> SEQUENCE: 137
aaaaacgact acaactacga cga                                          23

<210> SEQ ID NO 138
<211> LENGTH: 22
<212> TYPE: DNA
<213> ORGANISM: artificial
<220> FEATURE:
<223> OTHER INFORMATION: primer

<400> SEQUENCE: 138
aacaaactcg cttctacacg aa                                           22

<210> SEQ ID NO 139
<211> LENGTH: 21
<212> TYPE: DNA
<213> ORGANISM: artificial
<220> FEATURE:
<223> OTHER INFORMATION: primer

<400> SEQUENCE: 139
atacgacgca aaaactatcg c                                            21

<210> SEQ ID NO 140
<211> LENGTH: 22
<212> TYPE: DNA
<213> ORGANISM: artificial
<220> FEATURE:
<223> OTHER INFORMATION: primer

<400> SEQUENCE: 140
aaaaaccgat taacctacgc tc                                           22

<210> SEQ ID NO 141
<211> LENGTH: 21
<212> TYPE: DNA
<213> ORGANISM: artificial
<220> FEATURE:
<223> OTHER INFORMATION: primer

<400> SEQUENCE: 141
ccttcttaaa acgacgacga a                                            21

<210> SEQ ID NO 142
<211> LENGTH: 20
<212> TYPE: DNA
<213> ORGANISM: artificial
<220> FEATURE:
<223> OTHER INFORMATION: primer

<400> SEQUENCE: 142
ttcctcccga acctttacga                                              20

<210> SEQ ID NO 143
<211> LENGTH: 19
<212> TYPE: DNA
<213> ORGANISM: artificial
<220> FEATURE:
<223> OTHER INFORMATION: primer

<400> SEQUENCE: 143
cgaaaactcc gaaaccgat                                               19

<210> SEQ ID NO 144
```

```
<211> LENGTH: 19
<212> TYPE: DNA
<213> ORGANISM: artificial
<220> FEATURE:
<223> OTHER INFORMATION: primer

<400> SEQUENCE: 144
ctaataatcg cccttcgc                                                       19

<210> SEQ ID NO 145
<211> LENGTH: 22
<212> TYPE: DNA
<213> ORGANISM: artificial
<220> FEATURE:
<223> OTHER INFORMATION: primer

<400> SEQUENCE: 145
tcccgaacta aacgaaaccc cg                                                  22

<210> SEQ ID NO 146
<211> LENGTH: 19
<212> TYPE: DNA
<213> ORGANISM: artificial
<220> FEATURE:
<223> OTHER INFORMATION: primer

<400> SEQUENCE: 146
acaccacgca cctatacgc                                                      19

<210> SEQ ID NO 147
<211> LENGTH: 22
<212> TYPE: DNA
<213> ORGANISM: artificial
<220> FEATURE:
<223> OTHER INFORMATION: primer

<400> SEQUENCE: 147
acgtaatact aaacccgaac gc                                                  22

<210> SEQ ID NO 148
<211> LENGTH: 20
<212> TYPE: DNA
<213> ORGANISM: artificial
<220> FEATURE:
<223> OTHER INFORMATION: primer

<400> SEQUENCE: 148
aaacctccga aataaccgtc                                                     20

<210> SEQ ID NO 149
<211> LENGTH: 20
<212> TYPE: DNA
<213> ORGANISM: artificial
<220> FEATURE:
<223> OTHER INFORMATION: primer

<400> SEQUENCE: 149
acaatttacc ccgctcgact                                                     20

<210> SEQ ID NO 150
<211> LENGTH: 23
<212> TYPE: DNA
<213> ORGANISM: artificial
<220> FEATURE:
<223> OTHER INFORMATION: primer

<400> SEQUENCE: 150
```
aaatctcgaa actcacctaa cga                                            23

<210> SEQ ID NO 151
<211> LENGTH: 21
<212> TYPE: DNA
<213> ORGANISM: artificial
<220> FEATURE:
<223> OTHER INFORMATION: primer

<400> SEQUENCE: 151
ctaccttcgt acccttcgat t                                              21

<210> SEQ ID NO 152
<211> LENGTH: 20
<212> TYPE: DNA
<213> ORGANISM: artificial
<220> FEATURE:
<223> OTHER INFORMATION: primer

<400> SEQUENCE: 152
ccaacctaaa aaacgaccga                                                20

<210> SEQ ID NO 153
<211> LENGTH: 19
<212> TYPE: DNA
<213> ORGANISM: artificial
<220> FEATURE:
<223> OTHER INFORMATION: primer

<400> SEQUENCE: 153
aaataaaccc gatccgcaa                                                 19

<210> SEQ ID NO 154
<211> LENGTH: 19
<212> TYPE: DNA
<213> ORGANISM: artificial
<220> FEATURE:
<223> OTHER INFORMATION: primer

<400> SEQUENCE: 154
accaatcaac aacgcgaac                                                 19

<210> SEQ ID NO 155
<211> LENGTH: 21
<212> TYPE: DNA
<213> ORGANISM: artificial
<220> FEATURE:
<223> OTHER INFORMATION: primer

<400> SEQUENCE: 155
cgaaacgacc taaaaacctc g                                              21

<210> SEQ ID NO 156
<211> LENGTH: 23
<212> TYPE: DNA
<213> ORGANISM: artificial
<220> FEATURE:
<223> OTHER INFORMATION: primer

<400> SEQUENCE: 156
ttctactact ctcgctctcc gac                                            23

<210> SEQ ID NO 157
<211> LENGTH: 23
<212> TYPE: DNA

```
<213> ORGANISM: artificial
<220> FEATURE:
<223> OTHER INFORMATION: primer

<400> SEQUENCE: 157
tctatattaa aaacttcgct tcg                                             23

<210> SEQ ID NO 158
<211> LENGTH: 20
<212> TYPE: DNA
<213> ORGANISM: artificial
<220> FEATURE:
<223> OTHER INFORMATION: primer

<400> SEQUENCE: 158
aaaataacaa aacccgtccg                                                 20

<210> SEQ ID NO 159
<211> LENGTH: 20
<212> TYPE: DNA
<213> ORGANISM: artificial
<220> FEATURE:
<223> OTHER INFORMATION: primer

<400> SEQUENCE: 159
aaaccccgta caataaccga                                                 20

<210> SEQ ID NO 160
<211> LENGTH: 22
<212> TYPE: DNA
<213> ORGANISM: artificial
<220> FEATURE:
<223> OTHER INFORMATION: primer

<400> SEQUENCE: 160
gaaacgtaaa aatatcgtcg ca                                              22

<210> SEQ ID NO 161
<211> LENGTH: 21
<212> TYPE: DNA
<213> ORGANISM: artificial
<220> FEATURE:
<223> OTHER INFORMATION: primer

<400> SEQUENCE: 161 aaaaaccctca cgaacacgac t                                              21

<210> SEQ ID NO 162
<211> LENGTH: 19
<212> TYPE: DNA
<213> ORGANISM: artificial
<220> FEATURE:
<223> OTHER INFORMATION: primer

<400> SEQUENCE: 162
ttcctcaacc gtctccacg                                                  19

<210> SEQ ID NO 163
<211> LENGTH: 19
<212> TYPE: DNA
<213> ORGANISM: artificial
<220> FEATURE:
<223> OTHER INFORMATION: primer

<400> SEQUENCE: 163
tccccttact ttccgcgac                                                  19
```

```
<210> SEQ ID NO 164
<211> LENGTH: 20
<212> TYPE: DNA
<213> ORGANISM: artificial
<220> FEATURE:
<223> OTHER INFORMATION: primer

<400> SEQUENCE: 164
tccctactaa aaacgccgaa                                                   20

<210> SEQ ID NO 165
<211> LENGTH: 21
<212> TYPE: DNA
<213> ORGANISM: artificial
<220> FEATURE:
<223> OTHER INFORMATION: primer

<400> SEQUENCE: 165
aaattaacgt ccgctcatac g                                                 21

<210> SEQ ID NO 166
<211> LENGTH: 20
<212> TYPE: DNA
<213> ORGANISM: artificial
<220> FEATURE:
<223> OTHER INFORMATION: primer

<400> SEQUENCE: 166
ccatcactta tcctcgacgc                                                   20

<210> SEQ ID NO 167
<211> LENGTH: 21
<212> TYPE: DNA
<213> ORGANISM: artificial
<220> FEATURE:
<223> OTHER INFORMATION: primer

<400> SEQUENCE: 167
ataaactcca acgacgcgaa a                                                 21

<210> SEQ ID NO 168
<211> LENGTH: 22
<212> TYPE: DNA
<213> ORGANISM: artificial
<220> FEATURE:
<223> OTHER INFORMATION: primer

<400> SEQUENCE: 168
tcataataac gaaacgacga cc                                                22

<210> SEQ ID NO 169
<211> LENGTH: 21
<212> TYPE: DNA
<213> ORGANISM: artificial
<220> FEATURE:
<223> OTHER INFORMATION: primer

<400> SEQUENCE: 169
cgaatttttc ctacgtaacc g                                                 21

<210> SEQ ID NO 170
<211> LENGTH: 16
<212> TYPE: DNA
<213> ORGANISM: artificial
<220> FEATURE:
```

```
<223> OTHER INFORMATION: primer

<400> SEQUENCE: 170
ccctcccaaa cgccga                                                 16

<210> SEQ ID NO 171
<211> LENGTH: 20
<212> TYPE: DNA
<213> ORGANISM: artificial
<220> FEATURE:
<223> OTHER INFORMATION: primer

<400> SEQUENCE: 171
aaacgaacga acaacaacga                                             20

<210> SEQ ID NO 172
<211> LENGTH: 19
<212> TYPE: DNA
<213> ORGANISM: artificial
<220> FEATURE:
<223> OTHER INFORMATION: primer

<400> SEQUENCE: 172
cgccacaata acgtcgaaa                                              19

<210> SEQ ID NO 173
<211> LENGTH: 23
<212> TYPE: DNA
<213> ORGANISM: artificial
<220> FEATURE:
<223> OTHER INFORMATION: primer

<400> SEQUENCE: 173
aaaaacaatc aaatacgaaa cgc                                         23

<210> SEQ ID NO 174
<211> LENGTH: 19
<212> TYPE: DNA
<213> ORGANISM: artificial
<220> FEATURE:
<223> OTHER INFORMATION: primer

<400> SEQUENCE: 174
tcacaattac cccgaaacg                                              19

<210> SEQ ID NO 175
<211> LENGTH: 19
<212> TYPE: DNA
<213> ORGANISM: artificial
<220> FEATURE:
<223> OTHER INFORMATION: primer

<400> SEQUENCE: 175
cacgaccccc taactccgt                                              19

<210> SEQ ID NO 176
<211> LENGTH: 19
<212> TYPE: DNA
<213> ORGANISM: artificial
<220> FEATURE:
<223> OTHER INFORMATION: primer

<400> SEQUENCE: 176
aaacgctaaa accgcgaat                                              19
```

```
<210> SEQ ID NO 177
<211> LENGTH: 20
<212> TYPE: DNA
<213> ORGANISM: artificial
<220> FEATURE:
<223> OTHER INFORMATION: primer

<400> SEQUENCE: 177
ataaaaatcc cgacgaacga                                              20

<210> SEQ ID NO 178
<211> LENGTH: 19
<212> TYPE: DNA
<213> ORGANISM: artificial
<220> FEATURE:
<223> OTHER INFORMATION: primer

<400> SEQUENCE: 178
cccaaaacta ctcgccgct                                               19

<210> SEQ ID NO 179
<211> LENGTH: 21
<212> TYPE: DNA
<213> ORGANISM: artificial
<220> FEATURE:
<223> OTHER INFORMATION: primer

<400> SEQUENCE: 179
ctctctcatt ctacgccgtt c                                            21

<210> SEQ ID NO 180
<211> LENGTH: 23
<212> TYPE: DNA
<213> ORGANISM: artificial
<220> FEATURE:
<223> OTHER INFORMATION: primer

<400> SEQUENCE: 180
taacgctata aaactcctac cgc                                          23

<210> SEQ ID NO 181
<211> LENGTH: 19
<212> TYPE: DNA
<213> ORGANISM: artificial
<220> FEATURE:
<223> OTHER INFORMATION: primer

<400> SEQUENCE: 181
aaaaccacgc gaaaaacga                                               19

<210> SEQ ID NO 182
<211> LENGTH: 21
<212> TYPE: DNA
<213> ORGANISM: artificial
<220> FEATURE:
<223> OTHER INFORMATION: primer

<400> SEQUENCE: 182
aactcgcgac tcgaatcccc g                                            21

<210> SEQ ID NO 183
<211> LENGTH: 20
<212> TYPE: DNA
<213> ORGANISM: artificial
<220> FEATURE:
<223> OTHER INFORMATION: primer
```

<400> SEQUENCE: 183
cccgaaacaa actacacgac                                        20

<210> SEQ ID NO 184
<211> LENGTH: 20
<212> TYPE: DNA
<213> ORGANISM: artificial
<220> FEATURE:
<223> OTHER INFORMATION: primer

<400> SEQUENCE: 184
ctaacttaac cgcatcgctc                                        20

<210> SEQ ID NO 185
<211> LENGTH: 24
<212> TYPE: DNA
<213> ORGANISM: artificial
<220> FEATURE:
<223> OTHER INFORMATION: primer

<400> SEQUENCE: 185
cccgataaat aataacattc acga                                   24

<210> SEQ ID NO 186
<211> LENGTH: 22
<212> TYPE: DNA
<213> ORGANISM: artificial
<220> FEATURE:
<223> OTHER INFORMATION: primer

<400> SEQUENCE: 186
cgctaccgat atccgctaaa cg                                     22

<210> SEQ ID NO 187
<211> LENGTH: 21
<212> TYPE: DNA
<213> ORGANISM: artificial
<220> FEATURE:
<223> OTHER INFORMATION: primer

<400> SEQUENCE: 187
ccgcaaaaac ctaaaacgta a                                      21

<210> SEQ ID NO 188
<211> LENGTH: 23
<212> TYPE: DNA
<213> ORGANISM: artificial
<220> FEATURE:
<223> OTHER INFORMATION: primer

<400> SEQUENCE: 188
atctaaactt tccctatcga ccg                                    23

<210> SEQ ID NO 189
<211> LENGTH: 21
<212> TYPE: DNA
<213> ORGANISM: artificial
<220> FEATURE:
<223> OTHER INFORMATION: primer

<400> SEQUENCE: 189
taacgaaaac tacgacgacg a                                      21

<210> SEQ ID NO 190
<211> LENGTH: 19

```
<212> TYPE: DNA
<213> ORGANISM: artificial
<220> FEATURE:
<223> OTHER INFORMATION: primer

<400> SEQUENCE: 190
aaaactacaa ccgccgaca                                           19

<210> SEQ ID NO 191
<211> LENGTH: 22
<212> TYPE: DNA
<213> ORGANISM: artificial
<220> FEATURE:
<223> OTHER INFORMATION: primer

<400> SEQUENCE: 191
aacttcttat acccgatcct cg                                       22

<210> SEQ ID NO 192
<211> LENGTH: 20
<212> TYPE: DNA
<213> ORGANISM: artificial
<220> FEATURE:
<223> OTHER INFORMATION: primer

<400> SEQUENCE: 192
tatatcctcg ccccacgtaa                                          20

<210> SEQ ID NO 193
<211> LENGTH: 21
<212> TYPE: DNA
<213> ORGANISM: artificial
<220> FEATURE:
<223> OTHER INFORMATION: primer

<400> SEQUENCE: 193
atacgcctta caacccctac g                                        21

<210> SEQ ID NO 194
<211> LENGTH: 21
<212> TYPE: DNA
<213> ORGANISM: artificial
<220> FEATURE:
<223> OTHER INFORMATION: primer

<400> SEQUENCE: 194
acaaaatcct cgttctcgaa t                                        21

<210> SEQ ID NO 195
<211> LENGTH: 19
<212> TYPE: DNA
<213> ORGANISM: artificial
<220> FEATURE:
<223> OTHER INFORMATION: primer

<400> SEQUENCE: 195
tccaaatctt tttccgcga                                           19

<210> SEQ ID NO 196
<211> LENGTH: 19
<212> TYPE: DNA
<213> ORGANISM: artificial
<220> FEATURE:
<223> OTHER INFORMATION: primer

<400> SEQUENCE: 196
```

```
accgtcttct cgaacgacg                                              19

<210> SEQ ID NO 197
<211> LENGTH: 24
<212> TYPE: DNA
<213> ORGANISM: artificial
<220> FEATURE:
<223> OTHER INFORMATION: primer

<400> SEQUENCE: 197
gaacacctac ctcaaactaa cgac                                        24

<210> SEQ ID NO 198
<211> LENGTH: 19
<212> TYPE: DNA
<213> ORGANISM: artificial
<220> FEATURE:
<223> OTHER INFORMATION: primer

<400> SEQUENCE: 198
taaacgacga cctccatcg                                              19

<210> SEQ ID NO 199
<211> LENGTH: 20
<212> TYPE: DNA
<213> ORGANISM: artificial
<220> FEATURE:
<223> OTHER INFORMATION: primer

<400> SEQUENCE: 199
cgaacgcaaa accgaaatcg                                             20

<210> SEQ ID NO 200
<211> LENGTH: 19
<212> TYPE: DNA
<213> ORGANISM: artificial
<220> FEATURE:
<223> OTHER INFORMATION: primer

<400> SEQUENCE: 200
tctcctccga aaaacgctc                                              19

<210> SEQ ID NO 201
<211> LENGTH: 20
<212> TYPE: DNA
<213> ORGANISM: artificial
<220> FEATURE:
<223> OTHER INFORMATION: primer

<400> SEQUENCE: 201
aaaatactac gaaaccgccc                                             20

<210> SEQ ID NO 202
<211> LENGTH: 21
<212> TYPE: DNA
<213> ORGANISM: artificial
<220> FEATURE:
<223> OTHER INFORMATION: primer

<400> SEQUENCE: 202
gctccgaatc aaaattaacg a                                           21

<210> SEQ ID NO 203
<211> LENGTH: 21
<212> TYPE: DNA
<213> ORGANISM: artificial
```

```
<220> FEATURE:
<223> OTHER INFORMATION: primer

<400> SEQUENCE: 203
cgaactcacc tctctaccga c                                           21

<210> SEQ ID NO 204
<211> LENGTH: 25
<212> TYPE: DNA
<213> ORGANISM: artificial
<220> FEATURE:
<223> OTHER INFORMATION: primer

<400> SEQUENCE: 204
cgtataacta ttacctcgaa acgct                                       25

<210> SEQ ID NO 205
<211> LENGTH: 19
<212> TYPE: DNA
<213> ORGANISM: artificial
<220> FEATURE:
<223> OTHER INFORMATION: primer

<400> SEQUENCE: 205
cgacccctcc taactttcg                                              19

<210> SEQ ID NO 206
<211> LENGTH: 23
<212> TYPE: DNA
<213> ORGANISM: artificial
<220> FEATURE:
<223> OTHER INFORMATION: primer

<400> SEQUENCE: 206
aactaaaata cccgtactcc gct                                         23

<210> SEQ ID NO 207
<211> LENGTH: 25
<212> TYPE: DNA
<213> ORGANISM: artificial
<220> FEATURE:
<223> OTHER INFORMATION: primer

<400> SEQUENCE: 207
aaaaccttaa cgaaactaaa cgaaa                                       25

<210> SEQ ID NO 208
<211> LENGTH: 24
<212> TYPE: DNA
<213> ORGANISM: artificial
<220> FEATURE:
<223> OTHER INFORMATION: primer

<400> SEQUENCE: 208
gaaaaccata acgacgtact aacg                                        24

<210> SEQ ID NO 209
<211> LENGTH: 19
<212> TYPE: DNA
<213> ORGANISM: artificial
<220> FEATURE:
<223> OTHER INFORMATION: primer

<400> SEQUENCE: 209
ctccgaaaac catacgccc                                              19
```

<210> SEQ ID NO 210
<211> LENGTH: 19
<212> TYPE: DNA
<213> ORGANISM: artificial
<220> FEATURE:
<223> OTHER INFORMATION: primer

<400> SEQUENCE: 210
accatctcat cacgcctcg                                                  19

<210> SEQ ID NO 211
<211> LENGTH: 20
<212> TYPE: DNA
<213> ORGANISM: artificial
<220> FEATURE:
<223> OTHER INFORMATION: primer

<400> SEQUENCE: 211
atcccccgaa cattacgatt                                                 20

<210> SEQ ID NO 212
<211> LENGTH: 21
<212> TYPE: DNA
<213> ORGANISM: artificial
<220> FEATURE:
<223> OTHER INFORMATION: primer

<400> SEQUENCE: 212
ctacgaaatt ccctttacgc t                                               21

<210> SEQ ID NO 213
<211> LENGTH: 25
<212> TYPE: DNA
<213> ORGANISM: artificial
<220> FEATURE:
<223> OTHER INFORMATION: primer

<400> SEQUENCE: 213
gtaatccaaa aataaaaact acgcc                                           25

<210> SEQ ID NO 214
<211> LENGTH: 23
<212> TYPE: DNA
<213> ORGANISM: artificial
<220> FEATURE:
<223> OTHER INFORMATION: primer

<400> SEQUENCE: 214
cttcatctac acctcgatac ccg                                             23

<210> SEQ ID NO 215
<211> LENGTH: 19
<212> TYPE: DNA
<213> ORGANISM: artificial
<220> FEATURE:
<223> OTHER INFORMATION: primer

<400> SEQUENCE: 215
cccgataacc gcttcgtat                                                  19

<210> SEQ ID NO 216
<211> LENGTH: 22
<212> TYPE: DNA
<213> ORGANISM: artificial
<220> FEATURE:
<223> OTHER INFORMATION: primer -continued

<400> SEQUENCE: 216
acaaacgacc ctaaaaacga ac                                              22

<210> SEQ ID NO 217
<211> LENGTH: 22
<212> TYPE: DNA
<213> ORGANISM: artificial
<220> FEATURE:
<223> OTHER INFORMATION: primer

<400> SEQUENCE: 217
acgaatttta cctcaaacga cc                                              22

<210> SEQ ID NO 218
<211> LENGTH: 22
<212> TYPE: DNA
<213> ORGANISM: artificial
<220> FEATURE:
<223> OTHER INFORMATION: primer

<400> SEQUENCE: 218
aacccgaaac tacgactacg ac                                              22

<210> SEQ ID NO 219
<211> LENGTH: 20
<212> TYPE: DNA
<213> ORGANISM: artificial
<220> FEATURE:
<223> OTHER INFORMATION: primer

<400> SEQUENCE: 219
gccccttacc cataacgaac                                                 20

<210> SEQ ID NO 220
<211> LENGTH: 22
<212> TYPE: DNA
<213> ORGANISM: artificial
<220> FEATURE:
<223> OTHER INFORMATION: primer

<400> SEQUENCE: 220
gaacgacaaa caaaactcga aa                                              22

<210> SEQ ID NO 221
<211> LENGTH: 20
<212> TYPE: DNA
<213> ORGANISM: artificial
<220> FEATURE:
<223> OTHER INFORMATION: primer

<400> SEQUENCE: 221
gcgatcctat caaatccgaa                                                 20

<210> SEQ ID NO 222
<211> LENGTH: 23
<212> TYPE: DNA
<213> ORGANISM: artificial
<220> FEATURE:
<223> OTHER INFORMATION: primer

<400> SEQUENCE: 222
gaatactcta attccacgcg act                                             23

<210> SEQ ID NO 223

```
<211> LENGTH: 20
<212> TYPE: DNA
<213> ORGANISM: artificial
<220> FEATURE:
<223> OTHER INFORMATION: primer

<400> SEQUENCE: 223
gacttctcat accgcaatcg                                               20

<210> SEQ ID NO 224
<211> LENGTH: 20
<212> TYPE: DNA
<213> ORGANISM: artificial
<220> FEATURE:
<223> OTHER INFORMATION: primer

<400> SEQUENCE: 224
cctaccctcg aaacaaacga                                               20

<210> SEQ ID NO 225
<211> LENGTH: 19
<212> TYPE: DNA
<213> ORGANISM: artificial
<220> FEATURE:
<223> OTHER INFORMATION: primer

<400> SEQUENCE: 225
aacccgaatt acgcaaacg                                                19

<210> SEQ ID NO 226
<211> LENGTH: 19
<212> TYPE: DNA
<213> ORGANISM: artificial
<220> FEATURE:
<223> OTHER INFORMATION: primer

<400> SEQUENCE: 226
cgcctcaata ataccgacc                                                19

<210> SEQ ID NO 227
<211> LENGTH: 20
<212> TYPE: DNA
<213> ORGANISM: artificial
<220> FEATURE:
<223> OTHER INFORMATION: primer

<400> SEQUENCE: 227
cctctcgatt ccctacgttt                                               20

<210> SEQ ID NO 228
<211> LENGTH: 19
<212> TYPE: DNA
<213> ORGANISM: artificial
<220> FEATURE:
<223> OTHER INFORMATION: primer

<400> SEQUENCE: 228
taaccgcctt taaccccga                                                19

<210> SEQ ID NO 229
<211> LENGTH: 24
<212> TYPE: DNA
<213> ORGANISM: artificial
<220> FEATURE:
<223> OTHER INFORMATION: primer

<400> SEQUENCE: 229
```
cccgtacttc gctaactta aacg                                                24

<210> SEQ ID NO 230
<211> LENGTH: 20
<212> TYPE: DNA
<213> ORGANISM: artificial
<220> FEATURE:
<223> OTHER INFORMATION: primer

<400> SEQUENCE: 230
gcgttataca ataccccg                                                      20

<210> SEQ ID NO 231
<211> LENGTH: 23
<212> TYPE: DNA
<213> ORGANISM: artificial
<220> FEATURE:
<223> OTHER INFORMATION: primer

<400> SEQUENCE: 231
ctacgaccaa actaaatccg aac                                                23

<210> SEQ ID NO 232
<211> LENGTH: 20
<212> TYPE: DNA
<213> ORGANISM: artificial
<220> FEATURE:
<223> OTHER INFORMATION: primer

<400> SEQUENCE: 232
aaaaacccga acgaacgtaa                                                    20

<210> SEQ ID NO 233
<211> LENGTH: 20
<212> TYPE: DNA
<213> ORGANISM: artificial
<220> FEATURE:
<223> OTHER INFORMATION: primer

<400> SEQUENCE: 233
cgcatctaca aactccgaaa                                                    20

<210> SEQ ID NO 234
<211> LENGTH: 23
<212> TYPE: DNA
<213> ORGANISM: artificial
<220> FEATURE:
<223> OTHER INFORMATION: primer

<400> SEQUENCE: 234
taactactaa acccgaaccg aac                                                23

<210> SEQ ID NO 235
<211> LENGTH: 20
<212> TYPE: DNA
<213> ORGANISM: artificial
<220> FEATURE:
<223> OTHER INFORMATION: primer

<400> SEQUENCE: 235
cgaaacatcg acaccttcgt                                                    20

<210> SEQ ID NO 236
<211> LENGTH: 23
<212> TYPE: DNA

```
<213> ORGANISM: artificial
<220> FEATURE:
<223> OTHER INFORMATION: primer

<400> SEQUENCE: 236
cgaaataaaa actaacaatc gcc                                              23

<210> SEQ ID NO 237
<211> LENGTH: 21
<212> TYPE: DNA
<213> ORGANISM: artificial
<220> FEATURE:
<223> OTHER INFORMATION: primer

<400> SEQUENCE: 237
tcttcgataa ctctaccccg a                                                21

<210> SEQ ID NO 238
<211> LENGTH: 22
<212> TYPE: DNA
<213> ORGANISM: artificial
<220> FEATURE:
<223> OTHER INFORMATION: primer

<400> SEQUENCE: 238
gacaatcatc catcaatcga aa                                               22

<210> SEQ ID NO 239
<211> LENGTH: 21
<212> TYPE: DNA
<213> ORGANISM: artificial
<220> FEATURE:
<223> OTHER INFORMATION: primer

<400> SEQUENCE: 239
caattctaaa aacgcacgac t                                                21

<210> SEQ ID NO 240
<211> LENGTH: 20
<212> TYPE: DNA
<213> ORGANISM: artificial
<220> FEATURE:
<223> OTHER INFORMATION: primer

<400> SEQUENCE: 240
cacgaactaa cgctacgcaa                                                  20

<210> SEQ ID NO 241
<211> LENGTH: 22
<212> TYPE: DNA
<213> ORGANISM: artificial
<220> FEATURE:
<223> OTHER INFORMATION: primer

<400> SEQUENCE: 241
gacccctaca tcttaacaac cg                                               22

<210> SEQ ID NO 242
<211> LENGTH: 23
<212> TYPE: DNA
<213> ORGANISM: artificial
<220> FEATURE:
<223> OTHER INFORMATION: primer

<400> SEQUENCE: 242
tacctactcc gctaccaacg taa                                              23
```

```
<210> SEQ ID NO 243
<211> LENGTH: 20
<212> TYPE: DNA
<213> ORGANISM: artificial
<220> FEATURE:
<223> OTHER INFORMATION: primer

<400> SEQUENCE: 243
ctaattcgtc tatcccgtcc                                                   20

<210> SEQ ID NO 244
<211> LENGTH: 19
<212> TYPE: DNA
<213> ORGANISM: artificial
<220> FEATURE:
<223> OTHER INFORMATION: primer

<400> SEQUENCE: 244
attttacccc gctacctcg                                                    19

<210> SEQ ID NO 245
<211> LENGTH: 20
<212> TYPE: DNA
<213> ORGANISM: artificial
<220> FEATURE:
<223> OTHER INFORMATION: primer

<400> SEQUENCE: 245
aaaacgatac gctaaacccg                                                   20

<210> SEQ ID NO 246
<211> LENGTH: 21
<212> TYPE: DNA
<213> ORGANISM: artificial
<220> FEATURE:
<223> OTHER INFORMATION: primer

<400> SEQUENCE: 246
cacccgaatt acaaataccg a                                                 21

<210> SEQ ID NO 247
<211> LENGTH: 20
<212> TYPE: DNA
<213> ORGANISM: artificial
<220> FEATURE:
<223> OTHER INFORMATION: primer

<400> SEQUENCE: 247
ccgcaatatc actaaaccga                                                   20

<210> SEQ ID NO 248
<211> LENGTH: 27
<212> TYPE: DNA
<213> ORGANISM: artificial
<220> FEATURE:
<223> OTHER INFORMATION: primer

<400> SEQUENCE: 248
catacctcaa taacaaacaa acaaacg                                           27

<210> SEQ ID NO 249
<211> LENGTH: 19
<212> TYPE: DNA
<213> ORGANISM: artificial
<220> FEATURE:
```

```
<223> OTHER INFORMATION: primer

<400> SEQUENCE: 249
aaaaacaaaa cacgcgaaa                                                    19

<210> SEQ ID NO 250
<211> LENGTH: 19
<212> TYPE: DNA
<213> ORGANISM: artificial
<220> FEATURE:
<223> OTHER INFORMATION: primer

<400> SEQUENCE: 250
ttacctactt ccccgcgac                                                    19

<210> SEQ ID NO 251
<211> LENGTH: 19
<212> TYPE: DNA
<213> ORGANISM: artificial
<220> FEATURE:
<223> OTHER INFORMATION: primer

<400> SEQUENCE: 251
ccgacgacaa ctaccgaaa                                                    19

<210> SEQ ID NO 252
<211> LENGTH: 21
<212> TYPE: DNA
<213> ORGANISM: artificial
<220> FEATURE:
<223> OTHER INFORMATION: primer

<400> SEQUENCE: 252
ctacacccta aaacgcgaa c                                                  21

<210> SEQ ID NO 253
<211> LENGTH: 22
<212> TYPE: DNA
<213> ORGANISM: artificial
<220> FEATURE:
<223> OTHER INFORMATION: primer

<400> SEQUENCE: 253
cataaaacga acacccgaac cg                                                22

<210> SEQ ID NO 254
<211> LENGTH: 22
<212> TYPE: DNA
<213> ORGANISM: artificial
<220> FEATURE:
<223> OTHER INFORMATION: primer

<400> SEQUENCE: 254
acctaacaaa ctacgaacgc ca                                                22

<210> SEQ ID NO 255
<211> LENGTH: 22
<212> TYPE: DNA
<213> ORGANISM: artificial
<220> FEATURE:
<223> OTHER INFORMATION: primer

<400> SEQUENCE: 255
aactaaacaa cactccgaac ga                                                22
```

```
<210> SEQ ID NO 256
<211> LENGTH: 23
<212> TYPE: DNA
<213> ORGANISM: artificial
<220> FEATURE:
<223> OTHER INFORMATION: primer

<400> SEQUENCE: 256
ccgaatactc tctaaaaccc gat                                              23

<210> SEQ ID NO 257
<211> LENGTH: 21
<212> TYPE: DNA
<213> ORGANISM: artificial
<220> FEATURE:
<223> OTHER INFORMATION: primer

<400> SEQUENCE: 257
ccgtcgcctt cctccgacga a                                                21

<210> SEQ ID NO 258
<211> LENGTH: 22
<212> TYPE: DNA
<213> ORGANISM: artificial
<220> FEATURE:
<223> OTHER INFORMATION: primer

<400> SEQUENCE: 258
tactactacg ccgcttacgt cc                                               22

<210> SEQ ID NO 259
<211> LENGTH: 25
<212> TYPE: DNA
<213> ORGANISM: artificial
<220> FEATURE:
<223> OTHER INFORMATION: primer

<400> SEQUENCE: 259
acgtaaaata aacaatcaac tatcg                                            25

<210> SEQ ID NO 260
<211> LENGTH: 21
<212> TYPE: DNA
<213> ORGANISM: artificial
<220> FEATURE:
<223> OTHER INFORMATION: primer

<400> SEQUENCE: 260
taacacccaa accgaaaaac g                                                21

<210> SEQ ID NO 261
<211> LENGTH: 19
<212> TYPE: DNA
<213> ORGANISM: artificial
<220> FEATURE:
<223> OTHER INFORMATION: primer

<400> SEQUENCE: 261
aacgaatcca catacccga                                                   19

<210> SEQ ID NO 262
<211> LENGTH: 20
<212> TYPE: DNA
<213> ORGANISM: artificial
<220> FEATURE:
<223> OTHER INFORMATION: primer
```

<400> SEQUENCE: 262
cgctactcct taaaaacgcc                                        20

<210> SEQ ID NO 263
<211> LENGTH: 22
<212> TYPE: DNA
<213> ORGANISM: artificial
<220> FEATURE:
<223> OTHER INFORMATION: primer

<400> SEQUENCE: 263
acaacgaaat cgaaatcgt aa                                      22

<210> SEQ ID NO 264
<211> LENGTH: 19
<212> TYPE: DNA
<213> ORGANISM: artificial
<220> FEATURE:
<223> OTHER INFORMATION: primer

<400> SEQUENCE: 264
accattcccg actcctcgt                                         19

<210> SEQ ID NO 265
<211> LENGTH: 101
<212> TYPE: DNA
<213> ORGANISM: artificial
<220> FEATURE:
<223> OTHER INFORMATION: synthetic construct

<400> SEQUENCE: 265
gtttggttcg ggttagcgtt aattcggttt tcgtggaagt cgtggcgaaa ggcgagaggg      60
gtaaaaagtt gagaaatagg cgagcgggag agataagtag g                         101

<210> SEQ ID NO 266
<211> LENGTH: 110
<212> TYPE: DNA
<213> ORGANISM: artificial
<220> FEATURE:
<223> OTHER INFORMATION: synthetic construct

<400> SEQUENCE: 266
ttgcgtttta tttgtatttc gcgtcgtttc gcggttcgcg gttgattcgt ttttcggttt      60
gcgggttttt ggagttttat tttttagagt cggttaagtc gttcgttaag               110

<210> SEQ ID NO 267
<211> LENGTH: 114
<212> TYPE: DNA
<213> ORGANISM: artificial
<220> FEATURE:
<223> OTHER INFORMATION: synthetic construct

<400> SEQUENCE: 267
ttttattgcg agtcgtcggt cgttgttatg gacgtttatt atagttcggt gtcgtagagt      60
cgggagggtt cgtcgttttt tagggtattt ttcggaggcg ataagttcgg tata           114

<210> SEQ ID NO 268
<211> LENGTH: 106
<212> TYPE: DNA
<213> ORGANISM: artificial
<220> FEATURE:
<223> OTHER INFORMATION: synthetic construct

<400> SEQUENCE: 268

```
tgtataggag tcgaagggac gtattacgtt agttttagtt cggttttagc gatagttaac      60 gtttttgta gcgcggcggt ttcgaagtcg tcgttcggag ttgttt                      106

<210> SEQ ID NO 269
<211> LENGTH: 95
<212> TYPE: DNA
<213> ORGANISM: artificial
<220> FEATURE:
<223> OTHER INFORMATION: synthetic construct

<400> SEQUENCE: 269
gttaggtaag tggtacggcg agcgtaaggg aagggttag ttattgatta gcggtagtaa       60
ttgtaggaat cgtcgtcgta gttgtagtcg ttttt                                 95

<210> SEQ ID NO 270
<211> LENGTH: 91
<212> TYPE: DNA
<213> ORGANISM: artificial
<220> FEATURE:
<223> OTHER INFORMATION: synthetic construct

<400> SEQUENCE: 270
atttaatgag gacggtaggt agcgaggttt tattcgaagt ttttcggcgt tatgagtagt      60
taataggagt tcgtgtagaa gcgagtttgt t                                     91

<210> SEQ ID NO 271
<211> LENGTH: 117
<212> TYPE: DNA
<213> ORGANISM: artificial
<220> FEATURE:
<223> OTHER INFORMATION: synthetic construct

<400> SEQUENCE: 271
tttaatataa gtcgggttac gttcgagggt aataatatga ttaaaattat agtaggaatt      60
ataataagga ataagattta ggttaaagta aatatagcga tagttttttgc gtcgtat       117

<210> SEQ ID NO 272
<211> LENGTH: 116
<212> TYPE: DNA
<213> ORGANISM: artificial
<220> FEATURE:
<223> OTHER INFORMATION: synthetic construct

<400> SEQUENCE: 272
ttagggagta agtgcgtttg cgcgcggtgt gcgttttta acgcgattta aggcgtcggg       60
tttgttgtta attaattata aggtagtttc gttcgagcgt aggttaatcg gttttt         116

<210> SEQ ID NO 273
<211> LENGTH: 113
<212> TYPE: DNA
<213> ORGANISM: artificial
<220> FEATURE:
<223> OTHER INFORMATION: synthetic construct

<400> SEQUENCE: 273
tagacggtta cgagtaggcg gtaggttcgt tgtagggacg cgtttggtat cgcggcgttg      60
tcgtttagga gcggttttcg aagttttatt ttttcgtcgt cgttttaaga agg            113

<210> SEQ ID NO 274
<211> LENGTH: 107
<212> TYPE: DNA
```

<213> ORGANISM: artificial
<220> FEATURE:
<223> OTHER INFORMATION: synthetic construct

<400> SEQUENCE: 274
tttttcgtat tttaggaagt ggcgcggttt gtcgagggta gcgtggagga ggaagaggag    60
gcgcggttta acgcgatcga agtttcgtcg taaaggttcg ggaggaa                 107

<210> SEQ ID NO 275
<211> LENGTH: 101
<212> TYPE: DNA
<213> ORGANISM: artificial
<220> FEATURE:
<223> OTHER INFORMATION: synthetic construct

<400> SEQUENCE: 275
tttggggttc gattatattt cggttagcgc gttttaggtt ttcgattttt tgtagtaggt    60
gtttcgtatc gcggcgttag ggatcggttt cggagttttc g                       101

<210> SEQ ID NO 276
<211> LENGTH: 115
<212> TYPE: DNA
<213> ORGANISM: artificial
<220> FEATURE:
<223> OTHER INFORMATION: synthetic construct

<400> SEQUENCE: 276 gttattttc ggcgggttcg tttttttttt ttggttttta gttttattt tttatggtcg    60 ttcggggcgt tttagttgt ttaggttaga gaggtggcga agggcgatt attag         115

<210> SEQ ID NO 277
<211> LENGTH: 113
<212> TYPE: DNA
<213> ORGANISM: artificial
<220> FEATURE:
<223> OTHER INFORMATION: synthetic construct

<400> SEQUENCE: 277
tacgcgtagg ttttaagtcg cggttaatgg gcgacgcggt cgtagattcg ttcggtttcg    60
ttttgttttg tgagttttt cggtcgggtt gcggggtttc gtttagttcg gga           113

<210> SEQ ID NO 278
<211> LENGTH: 95
<212> TYPE: DNA
<213> ORGANISM: artificial
<220> FEATURE:
<223> OTHER INFORMATION: synthetic construct

<400> SEQUENCE: 278
tttgattttt gaaagcgtcg ttgcgtttcg cgtcgcgggt aggtagggcg ggattttag    60 gaggatcggt agaggcgcgt ataggtgcgt ggtgt                             95

<210> SEQ ID NO 279
<211> LENGTH: 119
<212> TYPE: DNA
<213> ORGANISM: artificial
<220> FEATURE:
<223> OTHER INFORMATION: synthetic construct

<400> SEQUENCE: 279
tttttaggga agtaaagcgt cgttttcgtc gtaggtatcg agacgtcgtt tagatggaag    60
aaatttggga gatgcgcgtt tttatatcgg tgtcgcggcg ttcgggttta gtattacgt    119

<210> SEQ ID NO 280
<211> LENGTH: 101
<212> TYPE: DNA
<213> ORGANISM: artificial
<220> FEATURE:
<223> OTHER INFORMATION: synthetic construct

<400> SEQUENCE: 280
tagtttggta gttagcgggt cggggcgttt agtttattt tttagagcgt tgcggttttg    60
tgtttgaagg ttaaatagtt tgacggttat ttcggaggtt t                      101

<210> SEQ ID NO 281
<211> LENGTH: 106
<212> TYPE: DNA
<213> ORGANISM: artificial
<220> FEATURE:
<223> OTHER INFORMATION: synthetic construct

<400> SEQUENCE: 281 ataggggag ttcggtacgg cgcgggcgtt taggagagaa ggaataataa atggatgagg    60
gggatgttta gggttgtttt cgggatagtc gagcgggta aattgt                  106

<210> SEQ ID NO 282
<211> LENGTH: 90
<212> TYPE: DNA
<213> ORGANISM: artificial
<220> FEATURE:
<223> OTHER INFORMATION: synthetic construct

<400> SEQUENCE: 282
cgtttttata gggttttggt tggacgtcgt cgtcgtcgtt gttatcgttt ttgatttaag   60 ttattttcg ttaggtgagt ttcgagattt                                    90

<210> SEQ ID NO 283
<211> LENGTH: 120
<212> TYPE: DNA
<213> ORGANISM: artificial
<220> FEATURE:
<223> OTHER INFORMATION: synthetic construct

<400> SEQUENCE: 283
tagttgtatc ggtttaggcg ttttggtggg gtgggaagga ttcgagtcgt atttgaatga   60
aggttagttt tttttaaga tattaattag gtagggagaa atcgaagggt acgaaggtag   120

<210> SEQ ID NO 284
<211> LENGTH: 152
<212> TYPE: DNA
<213> ORGANISM: artificial
<220> FEATURE:
<223> OTHER INFORMATION: synthetic construct

<400> SEQUENCE: 284
gttatggcga tgcggtttcg gagagcgtac gtttgtcgcg gtcggtatgg aaacgttttc   60
gttaggttcg ggggcgtcgt tgattggtcg atttaataga cgcgggtggg tagtttagtc  120
gtatcgttaa gttcggtcgt tttttaggtt gg                                152

<210> SEQ ID NO 285
<211> LENGTH: 96
<212> TYPE: DNA
<213> ORGANISM: artificial
<220> FEATURE:

<223> OTHER INFORMATION: synthetic construct

<400> SEQUENCE: 285
gaaggtagcg tttttcgatg gtgagtaggt tttgtaggac gcggtcgttt cggagtaggt    60
tgcggtttcg tacggttttg cggatcgggt ttattt    96

<210> SEQ ID NO 286
<211> LENGTH: 92
<212> TYPE: DNA
<213> ORGANISM: artificial
<220> FEATURE:
<223> OTHER INFORMATION: synthetic construct

<400> SEQUENCE: 286
aattttaggt tagagggtta tcgcgtttat gcgaggtcgg gtgggcgggt cgttagtttc    60
gttttgggga ggggttcgcg ttgttgattg gt    92

<210> SEQ ID NO 287
<211> LENGTH: 94
<212> TYPE: DNA
<213> ORGANISM: artificial
<220> FEATURE:
<223> OTHER INFORMATION: synthetic construct

<400> SEQUENCE: 287 gaggggtag gaaagtcgcg ttcgttttt attatttatt ttttattttt attattgggg    60
ggttcggagc gcgcgaggtt tttaggtcgt ttcg    94

<210> SEQ ID NO 288
<211> LENGTH: 91
<212> TYPE: DNA
<213> ORGANISM: artificial
<220> FEATURE:
<223> OTHER INFORMATION: synthetic construct

<400> SEQUENCE: 288
gggacgattt ttcgttgttc ggggttttcg aacggcgggg gcgggaggcg gtaatttatt    60
cggagcgcgt cggagagcga gagtagtaga a    91

<210> SEQ ID NO 289
<211> LENGTH: 92
<212> TYPE: DNA
<213> ORGANISM: artificial
<220> FEATURE:
<223> OTHER INFORMATION: synthetic construct

<400> SEQUENCE: 289
aatttcgttt gtagagtcgt cgtcgtcgtc gtcgtcggag gagcgagtcg atttttttt    60 ttttttttc gaagcgaagt ttttaatata ga    92

<210> SEQ ID NO 290
<211> LENGTH: 82
<212> TYPE: DNA
<213> ORGANISM: artificial
<220> FEATURE:
<223> OTHER INFORMATION: synthetic construct

<400> SEQUENCE: 290
gtcggtaagg tttggagagc ggttgggttc gcgggattcg cgggtttgta ttcgtttaga    60
ttcggacggg ttttgttatt tt    82

```
<210> SEQ ID NO 291
<211> LENGTH: 90
<212> TYPE: DNA
<213> ORGANISM: artificial
<220> FEATURE:
<223> OTHER INFORMATION: synthetic construct

<400> SEQUENCE: 291
ttagaagtaa tttaggcgcg ttcgttggtt tttgagcgtt aggaaaagtt cggagttaac    60
gatcggtcgt tcggttattg tacggggttt                                    90

<210> SEQ ID NO 292
<211> LENGTH: 108
<212> TYPE: DNA
<213> ORGANISM: artificial
<220> FEATURE:
<223> OTHER INFORMATION: synthetic construct

<400> SEQUENCE: 292
aatttgattt gtgtgtgtat cgcgttttta gcgatttcgg atttattgcg ttgttagggg    60 tttggggtg ggtttttgt tgttttgcg acgatatttt tacgtttc                   108

<210> SEQ ID NO 293
<211> LENGTH: 103
<212> TYPE: DNA
<213> ORGANISM: artificial
<220> FEATURE:
<223> OTHER INFORMATION: synthetic construct

<400> SEQUENCE: 293
gtttacgcga tttttgggac gtcggagata acggggtttt tgggaaggcg cggagttcgg    60
ggaagtcggg gatgtgcgcg tgagtcgtgt tcgtagggtt ttt                     103

<210> SEQ ID NO 294
<211> LENGTH: 100
<212> TYPE: DNA
<213> ORGANISM: artificial
<220> FEATURE:
<223> OTHER INFORMATION: synthetic construct

<400> SEQUENCE: 294 agggttttc ggagtcgttt attagggttt tttgggggtt cggtttcgat tgggtagggg    60
gatttggata gggtttcgga gcgtggagac ggttgaggaa                         100

<210> SEQ ID NO 295
<211> LENGTH: 103
<212> TYPE: DNA
<213> ORGANISM: artificial
<220> FEATURE:
<223> OTHER INFORMATION: synthetic construct

<400> SEQUENCE: 295
aggcgtcgta tttatagcgt tttgttcgcg tatatatttt ttttggggtt ggttgtaaat    60
ttgtatgatt tacgtttaaa gaatgtcgcg gaaagtaagg gga                     103

<210> SEQ ID NO 296
<211> LENGTH: 117
<212> TYPE: DNA
<213> ORGANISM: artificial
<220> FEATURE:
<223> OTHER INFORMATION: synthetic construct

<400> SEQUENCE: 296
```

```
gtgggggtcg gtgtagtatc gggttggggg cgtcggggg cgtattatta ttacgaatag      60
ttgtgttggt tttaggagag attttgaggt gcggtcgttc ggcgttttta gtaggga        117

<210> SEQ ID NO 297
<211> LENGTH: 106
<212> TYPE: DNA
<213> ORGANISM: artificial
<220> FEATURE:
<223> OTHER INFORMATION: synthetic construct

<400> SEQUENCE: 297
tataaaaggg gttcgggtta gtcgtcggag tagacgggag ttttttttcg gggtcggagt    60
aggaggtacg cggagtgtga ggttacgtat gagcggacgt taattt                  106

<210> SEQ ID NO 298
<211> LENGTH: 80
<212> TYPE: DNA
<213> ORGANISM: artificial
<220> FEATURE:
<223> OTHER INFORMATION: synthetic construct

<400> SEQUENCE: 298
aggaagtatt tattgcgtat gtttcgtagt ttgggatgtt gaggttgtga gcggaggcga    60
gcgtcgagga taagtgatgg                                                80

<210> SEQ ID NO 299
<211> LENGTH: 112
<212> TYPE: DNA
<213> ORGANISM: artificial
<220> FEATURE:
<223> OTHER INFORMATION: synthetic construct

<400> SEQUENCE: 299
taattttaag gaggacgagg gtcggttgtc gggcgcgggc gagaaaggtg aggaggggcg    60
taggcggtcg cgggttgggg gcgagcgtat atttcgcgtc gttggagttt at           112

<210> SEQ ID NO 300
<211> LENGTH: 86
<212> TYPE: DNA
<213> ORGANISM: artificial
<220> FEATURE:
<223> OTHER INFORMATION: synthetic construct

<400> SEQUENCE: 300
gttttgggag aggcggttcg ggttcgcgtt ttagttttcg tcgtcgtcgt cgttgggttc    60
gagcggtcgt cgtttcgtta ttatga                                         86

<210> SEQ ID NO 301
<211> LENGTH: 84
<212> TYPE: DNA
<213> ORGANISM: artificial
<220> FEATURE:
<223> OTHER INFORMATION: synthetic construct

<400> SEQUENCE: 301
ggtgtagcgt ttagggtcgt cgtaggtcgg gggtagggtt tttagcggtt ttttcgcggt    60
tagcggttac gtaggaaaaa ttcg                                           84

<210> SEQ ID NO 302
<211> LENGTH: 98
<212> TYPE: DNA
<213> ORGANISM: artificial
```

```
<220> FEATURE:
<223> OTHER INFORMATION: synthetic construct

<400> SEQUENCE: 302
ggatagtcgg atcgagttaa cgtcggggat tttgtttttt tcgcggaggg gattcggtaa    60
ttcgtagcgg tagggtttgg ggtcggcgtt tgggaggg                            98

<210> SEQ ID NO 303
<211> LENGTH: 93
<212> TYPE: DNA
<213> ORGANISM: artificial
<220> FEATURE:
<223> OTHER INFORMATION: synthetic construct

<400> SEQUENCE: 303
aggataggta tgaatttcgg tttcggaagg cggttattat ttttttttgtt tttcggtttt   60 ttcgttttcg ttttcgttgt tgttcgttcg ttt                                 93

<210> SEQ ID NO 304
<211> LENGTH: 82
<212> TYPE: DNA
<213> ORGANISM: artificial
<220> FEATURE:
<223> OTHER INFORMATION: synthetic construct

<400> SEQUENCE: 304
cgggtttgag ggtaatagaa tcgatagttt taagtgggta aagggtggtt aaataggagt    60
ggttttcgac gttattgtgg cg                                             82

<210> SEQ ID NO 305
<211> LENGTH: 107
<212> TYPE: DNA
<213> ORGANISM: artificial
<220> FEATURE:
<223> OTHER INFORMATION: synthetic construct

<400> SEQUENCE: 305 gtgcgggta agaaggaacg gaagcggtgc gatttatagg gttgggtttt tttgtatttt     60
gggttacgtt tttttggcga gaaagcgttt cgtatttgat tgttttt                 107

<210> SEQ ID NO 306
<211> LENGTH: 120
<212> TYPE: DNA
<213> ORGANISM: artificial
<220> FEATURE:
<223> OTHER INFORMATION: synthetic construct

<400> SEQUENCE: 306
gagagagaaa gcgggagttc gcggcgagcg tagcgtaagt tcgttttttta ggtatcgttg   60 cgttggtagc gattcgttgt tttttgtgag ttagggggata acgtttcggg gtaattgtga  120

<210> SEQ ID NO 307
<211> LENGTH: 101
<212> TYPE: DNA
<213> ORGANISM: artificial
<220> FEATURE:
<223> OTHER INFORMATION: synthetic construct

<400> SEQUENCE: 307
taggagcgtt gtttcggtcg tttcggaggg tcgtatcgtt gtttttcgaa gagttcgttt    60
cggttttttc gattaatatt ggacggagtt aggggggtcgt g                      101
```

<210> SEQ ID NO 308
<211> LENGTH: 83
<212> TYPE: DNA
<213> ORGANISM: artificial
<220> FEATURE:
<223> OTHER INFORMATION: synthetic construct

<400> SEQUENCE: 308
tttaggtggg aagcgtattt atcggacggt cggttcggtg aggcgtagcg ttttagattg    60
gcgtattcgc ggttttagcg ttt                                           83

<210> SEQ ID NO 309
<211> LENGTH: 113
<212> TYPE: DNA
<213> ORGANISM: artificial
<220> FEATURE:
<223> OTHER INFORMATION: synthetic construct

<400> SEQUENCE: 309
gggatagtgg ggttgacgcg tggtttcggc gtcgcgcggt ttttcgaatt tcagtttcg     60 cgttcggcgc ggtcggggtt tttaatcgtt ttttcgttcg tcgggatttt tat          113

<210> SEQ ID NO 310
<211> LENGTH: 83
<212> TYPE: DNA
<213> ORGANISM: artificial
<220> FEATURE:
<223> OTHER INFORMATION: synthetic construct

<400> SEQUENCE: 310
gcgtgggttt tcgtcgtagt ttcgcggagt ttcggtgttt tttgtaatag ggggcggggg    60
gaatagcggc gagtagtttt ggg                                           83

<210> SEQ ID NO 311
<211> LENGTH: 91
<212> TYPE: DNA
<213> ORGANISM: artificial
<220> FEATURE:
<223> OTHER INFORMATION: synthetic construct

<400> SEQUENCE: 311
cgggttgtag ttaatatcga gggtgtagtg cgggggagg cggggtcgc ggttggggga     60 ggggaggcgg gaacggcgta gaatgagaga g                                  91

<210> SEQ ID NO 312
<211> LENGTH: 95
<212> TYPE: DNA
<213> ORGANISM: artificial
<220> FEATURE:
<223> OTHER INFORMATION: synthetic construct

<400> SEQUENCE: 312
tttgttcgtt tttcgattgt tcgttttcg gggttcgggc gtatttttt aggtaggagt     60 agttgtggcg gcgcggtagg agttttatag cgtta                              95

<210> SEQ ID NO 313
<211> LENGTH: 92
<212> TYPE: DNA
<213> ORGANISM: artificial
<220> FEATURE:
<223> OTHER INFORMATION: synthetic construct

<400> SEQUENCE: 313

```
cgttaatcgg ataagagtgc gcgcgggatt cgtttttttt tttcggtatc gttttcgttt      60
tcgttttttc ggttcgtttt tcgcgtggtt tt                                    92

<210> SEQ ID NO 314
<211> LENGTH: 136
<212> TYPE: DNA
<213> ORGANISM: artificial
<220> FEATURE:
<223> OTHER INFORMATION: synthetic construct

<400> SEQUENCE: 314
gtatagtttc gtagtttgcg tttagcggag gtgtagtcgg ggtcgcgtat tttcgtttcg      60
tttttgtacg tgatttttat aggttagtta gcgttttagg gtcgagttgt tgggtcgggg     120
attcgagtcg cgagtt                                                     136

<210> SEQ ID NO 315
<211> LENGTH: 94
<212> TYPE: DNA
<213> ORGANISM: artificial
<220> FEATURE:
<223> OTHER INFORMATION: synthetic construct

<400> SEQUENCE: 315
ggtattgtta ttttgcgttt tcggagtcgt tggtgggcga taagttttcg tttatttttt      60
tttatgtgcg agttgtcgtg tagtttgttt cggg                                  94

<210> SEQ ID NO 316
<211> LENGTH: 96
<212> TYPE: DNA
<213> ORGANISM: artificial
<220> FEATURE:
<223> OTHER INFORMATION: synthetic construct

<400> SEQUENCE: 316
gatttcgggt tgttatggcg attttttaata atttgatttt tattaattgt agttggtggt     60
ttattttcgc gttggagagc gatgcggtta agttag                                96

<210> SEQ ID NO 317
<211> LENGTH: 114
<212> TYPE: DNA
<213> ORGANISM: artificial
<220> FEATURE:
<223> OTHER INFORMATION: synthetic construct

<400> SEQUENCE: 317
gaaagaagga ggtttcggcg cggcggtttt ttttcgttta gtattatatg gtttcgtcga      60
gtttgttttt tttttttttt ttttttcgtt tcgtgaatgt tattatttat cggg           114

<210> SEQ ID NO 318
<211> LENGTH: 72
<212> TYPE: DNA
<213> ORGANISM: artificial
<220> FEATURE:
<223> OTHER INFORMATION: synthetic construct

<400> SEQUENCE: 318
gttgtgagtt gcgtttttta cgtcggtttc gcgttttagg ggttgttgag cgtttagcgg      60
atatcggtag cg                                                          72

<210> SEQ ID NO 319
```

```
<211> LENGTH: 90
<212> TYPE: DNA
<213> ORGANISM: artificial
<220> FEATURE:
<223> OTHER INFORMATION: synthetic construct

<400> SEQUENCE: 319
ggtcgtagtc gtagtcggga gattgagggt tagggcgcgg tcgcggggtt ttttgggtcg     60
gggcgcggtt tacgttttag gttttttgcgg                                    90

<210> SEQ ID NO 320
<211> LENGTH: 108
<212> TYPE: DNA
<213> ORGANISM: artificial
<220> FEATURE:
<223> OTHER INFORMATION: synthetic construct

<400> SEQUENCE: 320
gaatttggta cgattttacg gagatttcgt ttttttagc gtagttttcg ttattgagcg     60
cgggattaac gtaggcgatg tcggcggtc gatagggaaa gtttagat                  108

<210> SEQ ID NO 321
<211> LENGTH: 94
<212> TYPE: DNA
<213> ORGANISM: artificial
<220> FEATURE:
<223> OTHER INFORMATION: synthetic construct

<400> SEQUENCE: 321
atttagtatt ggggcggagc ggggcgggat tatttttata aggttcggag gtcgcgaggt     60
tttcgttgga gtttcgtcgt cgtagttttc gtta                                94

<210> SEQ ID NO 322
<211> LENGTH: 107
<212> TYPE: DNA
<213> ORGANISM: artificial
<220> FEATURE:
<223> OTHER INFORMATION: synthetic construct

<400> SEQUENCE: 322
agtagtagga atagaaacgg cgacggcggc ggcggggtag gcggaggtag ggttagcgtt     60
gggttttaga tgatgttgag gttttttttg tcggcggttg tagtttt                  107

<210> SEQ ID NO 323
<211> LENGTH: 100
<212> TYPE: DNA
<213> ORGANISM: artificial
<220> FEATURE:
<223> OTHER INFORMATION: synthetic construct

<400> SEQUENCE: 323
gaagttggtt agggtacggt cgtgagcgga gcgggtaggg ttttttagg agcgcgggcg     60 aggtcggcgt tggaggggcg aggatcgggt ataagaagtt                          100

<210> SEQ ID NO 324
<211> LENGTH: 112
<212> TYPE: DNA
<213> ORGANISM: artificial
<220> FEATURE:
<223> OTHER INFORMATION: synthetic construct

<400> SEQUENCE: 324
ggatcgttgg attttggttc gagtattcgt tttcgttacg tggtaagttt gcgtggaaag    60
```

```
gataggtgag gtttcgtttt tttgtggttg gtttacgtgg ggcgaggata ta          112
```

<210> SEQ ID NO 325
<211> LENGTH: 88
<212> TYPE: DNA
<213> ORGANISM: artificial
<220> FEATURE:
<223> OTHER INFORMATION: synthetic construct

<400> SEQUENCE: 325

```
tttttagagt aaatagcggg agcgtattgg gggtatttat tatttacgtt tgtttttga   60 tttaacgcgt aggggttgta aggcgtat                                     88
```

<210> SEQ ID NO 326
<211> LENGTH: 89
<212> TYPE: DNA
<213> ORGANISM: artificial
<220> FEATURE:
<223> OTHER INFORMATION: synthetic construct

<400> SEQUENCE: 326

```
ttttatttat tcggggagtt gcgggtggga ggtggggacg agagttgagt ttttatcgtt  60
ttttgtatat tcgagaacga ggattttgt                                    89
```

<210> SEQ ID NO 327
<211> LENGTH: 110
<212> TYPE: DNA
<213> ORGANISM: artificial
<220> FEATURE:
<223> OTHER INFORMATION: synthetic construct

<400> SEQUENCE: 327

```
tcgtagggtt cgtagtcgtt tagaatggaa gggtaagagg tttaaatatg cggttaaaga  60
attcgttcgc gttcggcggg tttggcgcgt ttcgcggaaa aagatttgga             110
```

<210> SEQ ID NO 328
<211> LENGTH: 105
<212> TYPE: DNA
<213> ORGANISM: artificial
<220> FEATURE:
<223> OTHER INFORMATION: synthetic construct

<400> SEQUENCE: 328

```
gtcggttgac gttttgagat aagtcggaaa agggtcgggt tcgtcgaagg tcgcgtaatt  60
tatttggtcg ttgaggagga aagagtcgtc gttcgagaag acggt                  105
```

<210> SEQ ID NO 329
<211> LENGTH: 95
<212> TYPE: DNA
<213> ORGANISM: artificial
<220> FEATURE:
<223> OTHER INFORMATION: synthetic construct

<400> SEQUENCE: 329

```
tcggatttcg tttttagcgt atgttattag tattttatta gttgttcgtt cgggtttcgg  60
aggtagttaa cgtcgttagt ttgaggtagg tgttc                             95
```

<210> SEQ ID NO 330
<211> LENGTH: 90
<212> TYPE: DNA
<213> ORGANISM: artificial
<220> FEATURE:

<223> OTHER INFORMATION: synthetic construct

<400> SEQUENCE: 330

```
taggttggtt tggtttcggt cgtttagagt tttcgttgat tttttgttta tttcgggttt     60
ttagttcgtc gcgatggagg tcgtcgttta                                      90
```

<210> SEQ ID NO 331
<211> LENGTH: 91
<212> TYPE: DNA
<213> ORGANISM: artificial
<220> FEATURE:
<223> OTHER INFORMATION: synthetic construct

<400> SEQUENCE: 331

```
gggattataa gtcgcgtcgc gttgtcgttg gttttttagt aatttcgat atggcgttga      60
ggcggttatc gcgatttcgg ttttgcgttc g                                    91
```

<210> SEQ ID NO 332
<211> LENGTH: 96
<212> TYPE: DNA
<213> ORGANISM: artificial
<220> FEATURE:
<223> OTHER INFORMATION: synthetic construct

<400> SEQUENCE: 332

```
ttagatttcg taaacggtga aaacggattt aggcgatcga tatagtagag tcgcggtcgt     60
cggcggtttt gggtcgcgag cgttttcgg aggaga                                96
```

<210> SEQ ID NO 333
<211> LENGTH: 97
<212> TYPE: DNA
<213> ORGANISM: artificial
<220> FEATURE:
<223> OTHER INFORMATION: synthetic construct

<400> SEQUENCE: 333

```
tggatggagt ttaggttata tcgtcgagtt gtttgtgcgt gttattttg gaagttattt      60
cgtgtgttaa ttatgtaggg cggtttcgta gtatttt                              97
```

<210> SEQ ID NO 334
<211> LENGTH: 85
<212> TYPE: DNA
<213> ORGANISM: artificial
<220> FEATURE:
<223> OTHER INFORMATION: synthetic construct

<400> SEQUENCE: 334

```
aggagggatt gtcggattta cgcggcggtt cgttttttgt ttagtcgtaa ggttgttttc     60
gtagtcgtta attttgattc ggagc                                           85
```

<210> SEQ ID NO 335
<211> LENGTH: 103
<212> TYPE: DNA
<213> ORGANISM: artificial
<220> FEATURE:
<223> OTHER INFORMATION: synthetic construct

<400> SEQUENCE: 335

```
tttttagatt tatcgagtgg cggcggaggc gagatgcgcg ggggcgtgtt tttggttttg     60
ttgttgtgtg tcgtcgcgta gtgtcggtag agaggtgagt tcg                      103
```

```
<210> SEQ ID NO 336
<211> LENGTH: 105
<212> TYPE: DNA
<213> ORGANISM: artificial
<220> FEATURE:
<223> OTHER INFORMATION: synthetic construct

<400> SEQUENCE: 336
cggtatcgtt gtttaggagg cgtcgatatt tcgtaaagg tttagtcggg gtgaggggta      60 ttgggggcg atcgggttag agcgtttcga ggtaatagtt atacg                    105

<210> SEQ ID NO 337
<211> LENGTH: 106
<212> TYPE: DNA
<213> ORGANISM: artificial
<220> FEATURE:
<223> OTHER INFORMATION: synthetic construct

<400> SEQUENCE: 337
agttgtttgg tattcgcggt ttttaaaggg gaaagaaagt tgcgttcgcg ttaggcgtag     60
cgcgttcggc ggacgcggtt tttcgggcga aagttaggag gggtcg                  106

<210> SEQ ID NO 338
<211> LENGTH: 120
<212> TYPE: DNA
<213> ORGANISM: artificial
<220> FEATURE:
<223> OTHER INFORMATION: synthetic construct

<400> SEQUENCE: 338
gttagattga tttcgttcga ggaggacgtg gtttatagaa aataaaaacg gggtttaaat     60
tacgtgaggg aaggagaaat ttttaattaa ggaggcgagc ggagtacggg tattttagtt    120

<210> SEQ ID NO 339
<211> LENGTH: 120
<212> TYPE: DNA
<213> ORGANISM: artificial
<220> FEATURE:
<223> OTHER INFORMATION: synthetic construct

<400> SEQUENCE: 339
tagtagattt ttagcggtga agacgtagag tatcgggttg acgttagaat tgaagaaggt     60
taaggtcgta gttttcgttc gcgtcgtttg gtcggtttcg tttagtttcg ttaaggtttt    120

<210> SEQ ID NO 340
<211> LENGTH: 139
<212> TYPE: DNA
<213> ORGANISM: artificial
<220> FEATURE:
<223> OTHER INFORMATION: synthetic construct

<400> SEQUENCE: 340
ttcgggtttt tttgttttta attcgcgcgc gggggcgttt aggttattgg gtttcgcgga     60
gttagcgaga ggtttgcgcg gagtttgagc ggcgttcgtt tcgttttaag gtcgacgtta    120
gtacgtcgtt atggttttc                                                139

<210> SEQ ID NO 341
<211> LENGTH: 81
<212> TYPE: DNA
<213> ORGANISM: artificial
<220> FEATURE:
<223> OTHER INFORMATION: synthetic construct
```

<400> SEQUENCE: 341
gtaagtgagt tcgagtgtc gcgttttagt ttttttcgc ggcggtaagg gacgtacggg    60
tcgggcgtat ggttttcgga g    81

<210> SEQ ID NO 342
<211> LENGTH: 113
<212> TYPE: DNA
<213> ORGANISM: artificial
<220> FEATURE:
<223> OTHER INFORMATION: synthetic construct

<400> SEQUENCE: 342
gaaaggtcgg atttgttttt cgagggtcga gttagttttt gtagatggtt gtagttttag    60
ttatgagtgt tattttttt ttgttttat agggcgaggc gtgatgagat ggt    113

<210> SEQ ID NO 343
<211> LENGTH: 89
<212> TYPE: DNA
<213> ORGANISM: artificial
<220> FEATURE:
<223> OTHER INFORMATION: synthetic construct

<400> SEQUENCE: 343
agattttgtg gtttcgtcgt taattttttt tagttcggtt tagaatagga gattagttta    60
ggttcgttga atcgtaatgt tcgggggat    89

<210> SEQ ID NO 344
<211> LENGTH: 99
<212> TYPE: DNA
<213> ORGANISM: artificial
<220> FEATURE:
<223> OTHER INFORMATION: synthetic construct

<400> SEQUENCE: 344
gcggttttta aggagtttta ttttcgggat taaatggttc gtaaggtttg gggtagcggc    60
gttgtaggag atgagtttag cgtaaaggga atttcgtag    99

<210> SEQ ID NO 345
<211> LENGTH: 92
<212> TYPE: DNA
<213> ORGANISM: artificial
<220> FEATURE:
<223> OTHER INFORMATION: synthetic construct

<400> SEQUENCE: 345
gagagattcg ggattcgtgt gttttcggg gtttaaaggc gttgggcggg cggttgtttt    60
cgggagaggc gtagttttta tttttggatt ac    92

<210> SEQ ID NO 346
<211> LENGTH: 90
<212> TYPE: DNA
<213> ORGANISM: artificial
<220> FEATURE:
<223> OTHER INFORMATION: synthetic construct

<400> SEQUENCE: 346
agtacgttgt tcggagtttt ttcggcgtcg tcggcggtta cggacgcggc gtatatgtcg    60
gcgtttacgg gtatcgaggt gtagatgaag    90

<210> SEQ ID NO 347
<211> LENGTH: 89

```
<212> TYPE: DNA
<213> ORGANISM: artificial
<220> FEATURE:
<223> OTHER INFORMATION: synthetic construct

<400> SEQUENCE: 347
gcgtcgtttt gtatgggtat cgcgggtagc gggtagtcgg cgtgtatcgt ttttgggggt      60
agtgtcgtgt atacgaagcg gttatcggg                                       89

<210> SEQ ID NO 348
<211> LENGTH: 113
<212> TYPE: DNA
<213> ORGANISM: artificial
<220> FEATURE:
<223> OTHER INFORMATION: synthetic construct

<400> SEQUENCE: 348
cgagtagtag ttgcgtcggg attacggttc ggtgagtggt cgttgtcgtt tttacggagt      60
agtgggtaga gaggggtagt ggaggaggga agttcgtttt tagggtcgtt tgt            113

<210> SEQ ID NO 349
<211> LENGTH: 124
<212> TYPE: DNA
<213> ORGANISM: artificial
<220> FEATURE:
<223> OTHER INFORMATION: synthetic construct

<400> SEQUENCE: 349
tgtatgattt tagttcgcgg ataagtgggt gtgttagggt cgtttttaga gggtcggggt      60
tttttcgttt ggttaaattt tagattcgtt tattggggtt tgggtcgttt gaggtaaaat    120
tcgt                                                                 124

<210> SEQ ID NO 350
<211> LENGTH: 119
<212> TYPE: DNA
<213> ORGANISM: artificial
<220> FEATURE:
<223> OTHER INFORMATION: synthetic construct

<400> SEQUENCE: 350
gcgggattta tttgttacgg atttagttat ttcgttaaga ttttttttt attttcgagc      60 gttttagttg gcggggttgg ggagtcgtag tttcgcggtc gtagtcgtag tttcgggtt     119

<210> SEQ ID NO 351
<211> LENGTH: 81
<212> TYPE: DNA
<213> ORGANISM: artificial
<220> FEATURE:
<223> OTHER INFORMATION: synthetic construct

<400> SEQUENCE: 351
attgcgtcgg gtttagtttc ggttatttcg gttatttcgg cgttaggtag ttggtcggtt      60
cgttcgttat gggtaagggg c                                               81

<210> SEQ ID NO 352
<211> LENGTH: 83
<212> TYPE: DNA
<213> ORGANISM: artificial
<220> FEATURE:
<223> OTHER INFORMATION: synthetic construct

<400> SEQUENCE: 352
```

```
gtttagggaa agcggacgag agggaaggga ggtaggcgga ttcgatttat tttattagtt    60
ttttcgagtt ttgtttgtcg ttc                                           83
```

<210> SEQ ID NO 353
<211> LENGTH: 100
<212> TYPE: DNA
<213> ORGANISM: artificial
<220> FEATURE:
<223> OTHER INFORMATION: synthetic construct

<400> SEQUENCE: 353

```
gttcgtagtt cggggcgttg gggagggcgc ggttggattt gcggggttat aagaaggtag    60
tcggattttc gtatcgtagg ttcggatttg ataggatcgc                         100
```

<210> SEQ ID NO 354
<211> LENGTH: 114
<212> TYPE: DNA
<213> ORGANISM: artificial
<220> FEATURE:
<223> OTHER INFORMATION: synthetic construct

<400> SEQUENCE: 354

```
ttattttgcg agcggtttcg cgatacgagg tagtcgtttt cgttttcga cgcggttatg     60 ggttcggtcg gcgcggggt aagttagagc gagtcgcgtg gaattagagt attc          114
```

<210> SEQ ID NO 355
<211> LENGTH: 75
<212> TYPE: DNA
<213> ORGANISM: artificial
<220> FEATURE:
<223> OTHER INFORMATION: synthetic construct

<400> SEQUENCE: 355

```
gatttgggcg ttttggttt ttcgcggttt cgagttttcg ataaattttt tgcgtcgatt     60
gcggtatgag aagtc                                                    75
```

<210> SEQ ID NO 356
<211> LENGTH: 114
<212> TYPE: DNA
<213> ORGANISM: artificial
<220> FEATURE:
<223> OTHER INFORMATION: synthetic construct

<400> SEQUENCE: 356

```
gtgggtttta agtttacggt ttcgtagatt ttgattttaa gaaggttatt gaatattatt    60
atggtcgggg cggggagtgg gggtcggggt tatttcgttt gtttcgaggg tagg         114
```

<210> SEQ ID NO 357
<211> LENGTH: 119
<212> TYPE: DNA
<213> ORGANISM: artificial
<220> FEATURE:
<223> OTHER INFORMATION: synthetic construct

<400> SEQUENCE: 357

```
ggcggagttt gtatagaggc ggagtcgcgg tagtcggaga gaacgtttta gtaatagtcg    60
ttaggaggaa gttttaggag ttttgtcgt ttacggaacg cgtttgcgta attcgggtt    119
```

<210> SEQ ID NO 358
<211> LENGTH: 110
<212> TYPE: DNA
<213> ORGANISM: artificial

```
<220> FEATURE:
<223> OTHER INFORMATION: synthetic construct

<400> SEQUENCE: 358
tttttgggtt tcgttgtttc gagttggcgt cgttcgcgcg tttcgtcgta ttgatagcgg      60
cgcgagtttc gtaatcgcga gttttgtttt cggtcggtat tattgaggcg                110

<210> SEQ ID NO 359
<211> LENGTH: 84
<212> TYPE: DNA
<213> ORGANISM: artificial
<220> FEATURE:
<223> OTHER INFORMATION: synthetic construct

<400> SEQUENCE: 359
ttcgtttcgt ttaggtatcg tttttggttt aatttatttt cggcgcgttc ggttgtagcg      60
ggagaaacgt agggaatcga gagg                                             84

<210> SEQ ID NO 360
<211> LENGTH: 104
<212> TYPE: DNA
<213> ORGANISM: artificial
<220> FEATURE:
<223> OTHER INFORMATION: synthetic construct

<400> SEQUENCE: 360
tttaggatta tagtgagcga cgggagagga gggatgggga agttagaat tggcgagaag       60 gaaatggtta gattagaagt agaggtcggg gttaaaggcg gtta                      104

<210> SEQ ID NO 361
<211> LENGTH: 75
<212> TYPE: DNA
<213> ORGANISM: artificial
<220> FEATURE:
<223> OTHER INFORMATION: synthetic construct

<400> SEQUENCE: 361
gcgttgaagt cggggttcgt tttgtggttt cgttcggttc gcgtttgtta gcgtttaaag      60
ttagcgaagt acggg                                                       75

<210> SEQ ID NO 362
<211> LENGTH: 103
<212> TYPE: DNA
<213> ORGANISM: artificial
<220> FEATURE:
<223> OTHER INFORMATION: synthetic construct

<400> SEQUENCE: 362
ggtcgtttcg ttgttttata gcgtcggggg gaggggtcg cgtttcgta atcgcgcggg        60 gtgaaagatc aaggggagg cgtcgggggt atttgtataa cgc                        103

<210> SEQ ID NO 363
<211> LENGTH: 110
<212> TYPE: DNA
<213> ORGANISM: artificial
<220> FEATURE:
<223> OTHER INFORMATION: synthetic construct

<400> SEQUENCE: 363
ttacggttag tagaaggagt agcgtatttc gtagagaggt tcggacggtc gttatgttcg      60
ggtcgggcgg ttttagagtc gcgggatgtt cggatttagt ttggtcgtag                110
```

```
<210> SEQ ID NO 364
<211> LENGTH: 101
<212> TYPE: DNA
<213> ORGANISM: artificial
<220> FEATURE:
<223> OTHER INFORMATION: synthetic construct

<400> SEQUENCE: 364
tcgaggaaga agatgtcgaa gattacggtg agtgagagta cgtatatgat cgcgatttgt      60
attacgcgta ttatgtatag gttacgttcg ttcgggtttt t                         101

<210> SEQ ID NO 365
<211> LENGTH: 94
<212> TYPE: DNA
<213> ORGANISM: artificial
<220> FEATURE:
<223> OTHER INFORMATION: synthetic construct

<400> SEQUENCE: 365
gaggcgtaag taggcgaaat tttagtatat taattcggag gaggattagg gcgagtagta      60
gtcgtagtag tagatttcgg agtttgtaga tgcg                                  94

<210> SEQ ID NO 366
<211> LENGTH: 120
<212> TYPE: DNA
<213> ORGANISM: artificial
<220> FEATURE:
<223> OTHER INFORMATION: synthetic construct

<400> SEQUENCE: 366
gattagagcg agcgaacgaa tcgcggcggt tcggagagtt tcgagcgtag cgtaggattt      60
gggtacgtcg cgaggaatcg tgtagtttag cgcggtcgtt cggttcgggt ttagtagtta     120

<210> SEQ ID NO 367
<211> LENGTH: 111
<212> TYPE: DNA
<213> ORGANISM: artificial
<220> FEATURE:
<223> OTHER INFORMATION: synthetic construct

<400> SEQUENCE: 367
ggtttgttgg tcgtttttag cgaaggcgta gtagatgtcg atggcggtcg agatgattag      60
tatgttcgcg aatattacgt agttttatat tacgaaggtg tcgatgtttc g              111

<210> SEQ ID NO 368
<211> LENGTH: 101
<212> TYPE: DNA
<213> ORGANISM: artificial
<220> FEATURE:
<223> OTHER INFORMATION: synthetic construct

<400> SEQUENCE: 368
gtatttaggg tagcgggtcg attttttcgag gttttatatt tgggtttgag gggcgcggtt    60
cgtagcggcg ggtgtagggg cgattgttag ttttttatttc g                       101

<210> SEQ ID NO 369
<211> LENGTH: 111
<212> TYPE: DNA
<213> ORGANISM: artificial
<220> FEATURE:
<223> OTHER INFORMATION: synthetic construct

<400> SEQUENCE: 369
```

```
gcgttatggt gttttttatag cgtttcgttc gcgagttaga cggtagtagt cgttgattat    60
tttcgttcgg ggtcgttttt aggtgtagtt tcggggtaga gttatcgaag a             111

<210> SEQ ID NO 370
<211> LENGTH: 113
<212> TYPE: DNA
<213> ORGANISM: artificial
<220> FEATURE:
<223> OTHER INFORMATION: synthetic construct

<400> SEQUENCE: 370
ttgtaggcgg tttgtagtcg ttgagtggtc gtcgggagag ggggttgcg gcggggagg       60 gcggggagga gtttggtttt ggatgtgtgt ttttcgattg atggatgatt gtc           113

<210> SEQ ID NO 371
<211> LENGTH: 88
<212> TYPE: DNA
<213> ORGANISM: artificial
<220> FEATURE:
<223> OTHER INFORMATION: synthetic construct

<400> SEQUENCE: 371
gaggatcggt ttaggttgcg gcggagtcga gggcgaggga gaggtcgcgt gagtgagtag    60
agtttagagt cgtgcgtttt tagaattg                                        88

<210> SEQ ID NO 372
<211> LENGTH: 83
<212> TYPE: DNA
<213> ORGANISM: artificial
<220> FEATURE:
<223> OTHER INFORMATION: synthetic construct

<400> SEQUENCE: 372
aggggaagac gaagagcgta tatttatagt ttttcggtgt tgcggggat attttttgggt    60 acgttgcgta gcgttagttc gtg                                             83

<210> SEQ ID NO 373
<211> LENGTH: 94
<212> TYPE: DNA
<213> ORGANISM: artificial
<220> FEATURE:
<223> OTHER INFORMATION: synthetic construct

<400> SEQUENCE: 373
tagcggagag gagattacgc gtttttttgtt ttttaaggat gaatttggcg gtaaaagagt    60
tggggttttt aacggttgtt aagatgtagg ggtc                                 94

<210> SEQ ID NO 374
<211> LENGTH: 96
<212> TYPE: DNA
<213> ORGANISM: artificial
<220> FEATURE:
<223> OTHER INFORMATION: synthetic construct

<400> SEQUENCE: 374
aggggtattt ataggcgttt agcgttgcgg gggatgtttc gaggaatcgc gcggaggttt    60
agttcgtggt agtttacgtt ggtagcggag taggta                              96

<210> SEQ ID NO 375
<211> LENGTH: 87
<212> TYPE: DNA
```

```
<213> ORGANISM: artificial
<220> FEATURE:
<223> OTHER INFORMATION: synthetic construct

<400> SEQUENCE: 375
gaagggtaat cgggtgtttt cggcgtcgtt cggggttttg agggttggtt agggtttagg    60
tcggggggga cgggatagac gaattag                                       87

<210> SEQ ID NO 376
<211> LENGTH: 116
<212> TYPE: DNA
<213> ORGANISM: artificial
<220> FEATURE:
<223> OTHER INFORMATION: synthetic construct

<400> SEQUENCE: 376
gatagggttt tgttttcggc gggtgtggag atagttgggg cggaggaggg tgtgttaggg    60
cgcgttttaa gagggtttgg cggtagaaag tggaattcga ggtagcgggg taaaat       116

<210> SEQ ID NO 377
<211> LENGTH: 115
<212> TYPE: DNA
<213> ORGANISM: artificial
<220> FEATURE:
<223> OTHER INFORMATION: synthetic construct

<400> SEQUENCE: 377
ttgtagtttt cgagttggag gtcgttgagg atcgagcgta ggaggaagga gatagcgcgt    60
agcggcggtc ggcgaggaga tagtatattt cgggtcgggt ttagcgtatc gtttt        115

<210> SEQ ID NO 378
<211> LENGTH: 86
<212> TYPE: DNA
<213> ORGANISM: artificial
<220> FEATURE:
<223> OTHER INFORMATION: synthetic construct

<400> SEQUENCE: 378
gttaggagtt cgtcggttag cgagtatttg ttttttttga gtagcgtttt ggttttgcgg    60
cgcggtcggt atttgtaatt cgggtg                                        86

<210> SEQ ID NO 379
<211> LENGTH: 117
<212> TYPE: DNA
<213> ORGANISM: artificial
<220> FEATURE:
<223> OTHER INFORMATION: synthetic construct

<400> SEQUENCE: 379
gagatgtttc gagggttgcg cgggtttttc ggttcgaagt cgtcgttcgt gttttggttt    60
gtcgcggttt ggtttatagc gtatttaggg ttttagtcg gtttagtgat attgcgg       117

<210> SEQ ID NO 380
<211> LENGTH: 70
<212> TYPE: DNA
<213> ORGANISM: artificial
<220> FEATURE:
<223> OTHER INFORMATION: synthetic construct

<400> SEQUENCE: 380
tttcgcggtt tttagattg ttcggagagc gcgttttgtt tgtcgtttgt tgtttgtta     60 ttgaggtatg                                                          70
```

<210> SEQ ID NO 381
<211> LENGTH: 89
<212> TYPE: DNA
<213> ORGANISM: artificial
<220> FEATURE:
<223> OTHER INFORMATION: synthetic construct

<400> SEQUENCE: 381
atcgtaggtt gggtttggtc gttggtaggg aagtgggtag aggggaggtt cggttaggtt    60
tttcggtaat tttcgcgtgt tttgttttt                                     89

<210> SEQ ID NO 382
<211> LENGTH: 114
<212> TYPE: DNA
<213> ORGANISM: artificial
<220> FEATURE:
<223> OTHER INFORMATION: synthetic construct

<400> SEQUENCE: 382
tggttgcgtt gtttatcgtt ttggttttgg gttgtgttat cggcgttttt tcggatttta    60
gatttcgtta gttttttgtag aagttttttgg ttgttgtcgc ggggaagtag gtaa        114

<210> SEQ ID NO 383
<211> LENGTH: 98
<212> TYPE: DNA
<213> ORGANISM: artificial
<220> FEATURE:
<223> OTHER INFORMATION: synthetic construct

<400> SEQUENCE: 383
gggtatttat tgcgacggat agtttcgcgg ggtgttgagt tttttttggtt ttttcgagcg   60 tacgttggtc gtttcgtatt ttcggtagtt gtcgtcgg                            98

<210> SEQ ID NO 384
<211> LENGTH: 88
<212> TYPE: DNA
<213> ORGANISM: artificial
<220> FEATURE:
<223> OTHER INFORMATION: synthetic construct

<400> SEQUENCE: 384
ggtttcgata gcgtagttgt ttcgggcgga ttcgggggtt tgggtcgcgt ttttcgttc     60 gcgcgtcgtt cgcgttttta gggtgtag                                      88

<210> SEQ ID NO 385
<211> LENGTH: 87
<212> TYPE: DNA
<213> ORGANISM: artificial
<220> FEATURE:
<223> OTHER INFORMATION: synthetic construct

<400> SEQUENCE: 385
gttcgttggg taaggcgttc gagaaagcgt ttggcgggag gaggtgcgcg gttttttgtt    60
ttaggcggtt cgggtgttcg ttttatg                                       87

<210> SEQ ID NO 386
<211> LENGTH: 80
<212> TYPE: DNA
<213> ORGANISM: artificial
<220> FEATURE:
<223> OTHER INFORMATION: synthetic construct

```
<400> SEQUENCE: 386
taaggaattt tgtattcgga ggcggggagg gcgtaggtaa attcggtttt ggcggcgttg    60
gcgttcgtag tttgttaggt                                                80

<210> SEQ ID NO 387
<211> LENGTH: 113
<212> TYPE: DNA
<213> ORGANISM: artificial
<220> FEATURE:
<223> OTHER INFORMATION: synthetic construct

<400> SEQUENCE: 387
gtggttagcg gatttcgagt cgtttttagt ttgtagtcgt ttgttttttta gtagttttaa    60 gttgtgagtt tatattttgc gttcgtcgat ttcgttcgga gtgttgttta gtt           113

<210> SEQ ID NO 388
<211> LENGTH: 92
<212> TYPE: DNA
<213> ORGANISM: artificial
<220> FEATURE:
<223> OTHER INFORMATION: synthetic construct

<400> SEQUENCE: 388
tttcgtaggg ttcggtgtcg ttttttatcg ttgttgtatt cggtagtttt ggagattgtt    60
attcgaaaaa tcgggtttta gagagtattc gg                                  92

<210> SEQ ID NO 389
<211> LENGTH: 77
<212> TYPE: DNA
<213> ORGANISM: artificial
<220> FEATURE:
<223> OTHER INFORMATION: synthetic construct

<400> SEQUENCE: 389
gttagggttc gggggcgttg ttcgtacgtt tcggcgggga aggaaatcgt ttcgcgttcg    60
tcggaggaag gcgacgg                                                   77

<210> SEQ ID NO 390
<211> LENGTH: 112
<212> TYPE: DNA
<213> ORGANISM: artificial
<220> FEATURE:
<223> OTHER INFORMATION: synthetic construct

<400> SEQUENCE: 390
tttagttcgt tagtttcgtc ggtcgacgat agtttgagta atagcgagga agagttagat    60
cggtagtagt cgtcgagcgg taagcgcggg ggacgtaagc ggcgtagtag ta            112

<210> SEQ ID NO 391
<211> LENGTH: 85
<212> TYPE: DNA
<213> ORGANISM: artificial
<220> FEATURE:
<223> OTHER INFORMATION: synthetic construct

<400> SEQUENCE: 391
ttttgtggtt agtcgcggta ggggaatttg gagtttttttg gttatttttag tagaagttat    60 cgatagttga ttgtttatttt tacgt                                          85

<210> SEQ ID NO 392
<211> LENGTH: 93
```

```
<212> TYPE: DNA
<213> ORGANISM: artificial
<220> FEATURE:
<223> OTHER INFORMATION: synthetic construct

<400> SEQUENCE: 392
gcgtcgttag atattttgtt gcgttgtagt tttttagtt agggttgttt tcgtttagac    60
ggttgggcgc gtcgttttc ggtttgggtg tta                                 93

<210> SEQ ID NO 393
<211> LENGTH: 87
<212> TYPE: DNA
<213> ORGANISM: artificial
<220> FEATURE:
<223> OTHER INFORMATION: synthetic construct

<400> SEQUENCE: 393
gtatggagcg ttttgcgatt gtaggagtac gttagttttt tagcgttggt ttagtgtcgt   60
ttgggttttc gggtatgtgg attcgtt                                       87

<210> SEQ ID NO 394
<211> LENGTH: 118
<212> TYPE: DNA
<213> ORGANISM: artificial
<220> FEATURE:
<223> OTHER INFORMATION: synthetic construct

<400> SEQUENCE: 394
tgtgttatat cggttagttg agagcgcgtg ttgggttgaa gaggagggtg ttttcgagag   60
ggacgttttt tcggattcgt ttttatttta gttgcgaggg cgtttttaag gagtagcg    118

<210> SEQ ID NO 395
<211> LENGTH: 107
<212> TYPE: DNA
<213> ORGANISM: artificial
<220> FEATURE:
<223> OTHER INFORMATION: synthetic construct

<400> SEQUENCE: 395
cgtttgtttt tataggttcg ggtaatggag attcgcggtc gttttcgttt tttgattttg   60
ttttattttt tacgttcgtt gtcgtttacg attttcgatt tcgttgt               107

<210> SEQ ID NO 396
<211> LENGTH: 109
<212> TYPE: DNA
<213> ORGANISM: artificial
<220> FEATURE:
<223> OTHER INFORMATION: synthetic construct

<400> SEQUENCE: 396
tgtatgcgga gaggtcgtag ttattgttgt gagtaggata tagtggcggt tgatttggga   60
gaagttatag agggacgggg tgggagaggg acgaggagtc gggaatggt             109

<210> SEQ ID NO 397
<211> LENGTH: 43
<212> TYPE: DNA
<213> ORGANISM: artificial
<220> FEATURE:
<223> OTHER INFORMATION: hybridization probe

<400> SEQUENCE: 397
cgacatgcgc ggttgattcg tttttcggtt tgcgggcatg tcg                    43
```

```
<210> SEQ ID NO 398
<211> LENGTH: 47
<212> TYPE: DNA
<213> ORGANISM: artificial
<220> FEATURE:
<223> OTHER INFORMATION: hybridization probe

<400> SEQUENCE: 398
cgacatgccg tcgtaggtat cgagacgtcg tttagatggg catgtcg        47

<210> SEQ ID NO 399
<211> LENGTH: 44
<212> TYPE: DNA
<213> ORGANISM: artificial
<220> FEATURE:
<223> OTHER INFORMATION: hybridization probe

<400> SEQUENCE: 399
cgacatgcgt agtcggggtc gcgtattttc gtttcggcat gtcg           44

<210> SEQ ID NO 400
<211> LENGTH: 43
<212> TYPE: DNA
<213> ORGANISM: artificial
<220> FEATURE:
<223> OTHER INFORMATION: hybridization probe

<400> SEQUENCE: 400
cgacatgcga taaaaactca actctcgtcc ccaccgcatg tcg            43

<210> SEQ ID NO 401
<211> LENGTH: 35
<212> TYPE: DNA
<213> ORGANISM: artificial
<220> FEATURE:
<223> OTHER INFORMATION: hybridization probe

<400> SEQUENCE: 401
cgacacgata tggcgttgag gcggttatcg tgtcg                     35

<210> SEQ ID NO 402
<211> LENGTH: 33
<212> TYPE: DNA
<213> ORGANISM: artificial
<220> FEATURE:
<223> OTHER INFORMATION: hybridization probe

<400> SEQUENCE: 402
cgtctgcaac cgccgacgac cgcgacgcag acg                       33

<210> SEQ ID NO 403
<211> LENGTH: 35
<212> TYPE: DNA
<213> ORGANISM: artificial
<220> FEATURE:
<223> OTHER INFORMATION: hybridization probe

<400> SEQUENCE: 403
cgacatgccc gatcgccccc caataccgca tgtcg                     35

<210> SEQ ID NO 404
<211> LENGTH: 34
<212> TYPE: DNA
<213> ORGANISM: artificial
<220> FEATURE:
<223> OTHER INFORMATION: hybridization probe
```

<400> SEQUENCE: 404
cgacatgcgg cgttgggcgg gcggttgcat gtcg         34

<210> SEQ ID NO 405
<211> LENGTH: 39
<212> TYPE: DNA
<213> ORGANISM: artificial
<220> FEATURE:
<223> OTHER INFORMATION: hybridization probe

<400> SEQUENCE: 405
acatgccgtt tttagagggt cggggttttt tcggcatgt    39

<210> SEQ ID NO 406
<211> LENGTH: 37
<212> TYPE: DNA
<213> ORGANISM: artificial
<220> FEATURE:
<223> OTHER INFORMATION: hybridization probe

<400> SEQUENCE: 406
cgacatgcga cccaaacccc cgaatccgcg catgtcg      37

<210> SEQ ID NO 407
<211> LENGTH: 38
<212> TYPE: DNA
<213> ORGANISM: artificial
<220> FEATURE:
<223> OTHER INFORMATION: hybridization probe

<400> SEQUENCE: 407
cgacatgcac cgcgcacctc ctcccgccaa gcatgtcg     38

<210> SEQ ID NO 408
<211> LENGTH: 38
<212> TYPE: DNA
<213> ORGANISM: artificial
<220> FEATURE:
<223> OTHER INFORMATION: hybridization probe

<400> SEQUENCE: 408
cgacatgccg gcggggaagg aaatcgtttc gcatgtcg     38

<210> SEQ ID NO 409
<211> LENGTH: 36
<212> TYPE: DNA
<213> ORGANISM: artificial
<220> FEATURE:
<223> OTHER INFORMATION: hybridization probe

<400> SEQUENCE: 409
cgacatgcac gacgccccccg aacctaacgc atgtcg      36

<210> SEQ ID NO 410
<211> LENGTH: 34
<212> TYPE: DNA
<213> ORGANISM: artificial
<220> FEATURE:
<223> OTHER INFORMATION: hybridization probe

<400> SEQUENCE: 410
cgacatgccc gacttccccg aactccgcat gtcg         34

<210> SEQ ID NO 411

-continued

```
<211> LENGTH: 44
<212> TYPE: DNA
<213> ORGANISM: artificial
<220> FEATURE:
<223> OTHER INFORMATION: hybridization probe

<400> SEQUENCE: 411
cgacatgcgc gatttcggat ttattgcgtt gttagggcat gtcg            44

<210> SEQ ID NO 412
<211> LENGTH: 39
<212> TYPE: DNA
<213> ORGANISM: artificial
<220> FEATURE:
<223> OTHER INFORMATION: hybridization probe

<400> SEQUENCE: 412
cgacatgcgg gattaacgta ggcgatgtcg ggcatgtcg                  39

<210> SEQ ID NO 413
<211> LENGTH: 37
<212> TYPE: DNA
<213> ORGANISM: artificial
<220> FEATURE:
<223> OTHER INFORMATION: hybridization probe

<400> SEQUENCE: 413
cgacatgcgg tttttgggt cggggcgcgg catgtcg                     37

<210> SEQ ID NO 414
<211> LENGTH: 43
<212> TYPE: DNA
<213> ORGANISM: artificial
<220> FEATURE:
<223> OTHER INFORMATION: hybridization probe

<400> SEQUENCE: 414
cgacatgcag ggttttttta ggagcgcggg cgagggcatg tcg             43

<210> SEQ ID NO 415
<211> LENGTH: 38
<212> TYPE: DNA
<213> ORGANISM: artificial
<220> FEATURE:
<223> OTHER INFORMATION: hybridization probe

<400> SEQUENCE: 415
cgacatgcgg gtcgggttcg tcgaaggtcg gcatgtcg                   38

<210> SEQ ID NO 416
<211> LENGTH: 33
<212> TYPE: DNA
<213> ORGANISM: artificial
<220> FEATURE:
<223> OTHER INFORMATION: hybridization probe

<400> SEQUENCE: 416
cgacatgcca aaaacacgcc cccgcgcatg tcg                        33

<210> SEQ ID NO 417
<211> LENGTH: 43
<212> TYPE: DNA
<213> ORGANISM: artificial
<220> FEATURE:
<223> OTHER INFORMATION: hybridization probe

<400> SEQUENCE: 417
```

```
cgacatgcgt agttttcgtt cgcgtcgttt ggtcggcatg tcg          43
```

<210> SEQ ID NO 418
<211> LENGTH: 42
<212> TYPE: DNA
<213> ORGANISM: artificial
<220> FEATURE:
<223> OTHER INFORMATION: hybridization probe

<400> SEQUENCE: 418

```
cgacatgcaa acgaacgccg ctcaaactcc gcgcgcatgt cg           42
```

<210> SEQ ID NO 419
<211> LENGTH: 52
<212> TYPE: DNA
<213> ORGANISM: artificial
<220> FEATURE:
<223> OTHER INFORMATION: hybridization probe

<400> SEQUENCE: 419

```
cgacatgcgt tcggtttaga ataggagatt agtttaggtt cgttgcatgt cg     52
```

<210> SEQ ID NO 420
<211> LENGTH: 39
<212> TYPE: DNA
<213> ORGANISM: artificial
<220> FEATURE:
<223> OTHER INFORMATION: hybridization probe

<400> SEQUENCE: 420

```
cgacatgggt tcgtaaggtt tggggtagcg gccatgtcg              39
```

<210> SEQ ID NO 421
<211> LENGTH: 36
<212> TYPE: DNA
<213> ORGANISM: artificial
<220> FEATURE:
<223> OTHER INFORMATION: hybridization probe

<400> SEQUENCE: 421

```
cgacatgcgc gggtagtcgg cgtgtatcgc atgtcg                 36
```

<210> SEQ ID NO 422
<211> LENGTH: 42
<212> TYPE: DNA
<213> ORGANISM: artificial
<220> FEATURE:
<223> OTHER INFORMATION: hybridization probe

<400> SEQUENCE: 422

```
cgtctgcgtg gtttcgttcg gttcgcgttt gttaggcaga cg          42
```

<210> SEQ ID NO 423
<211> LENGTH: 43
<212> TYPE: DNA
<213> ORGANISM: artificial
<220> FEATURE:
<223> OTHER INFORMATION: hybridization probe

<400> SEQUENCE: 423

```
cgacatgcgg aggattaggg cgagtagtag tcgtagcatg tcg         43
```

<210> SEQ ID NO 424
<211> LENGTH: 43
<212> TYPE: DNA

```
<213> ORGANISM: artificial
<220> FEATURE:
<223> OTHER INFORMATION: hybridization probe

<400> SEQUENCE: 424
cgacatgcgt tcgtgttttg gtttgtcgcg gtttggcatg tcg             43

<210> SEQ ID NO 425
<211> LENGTH: 40
<212> TYPE: DNA
<213> ORGANISM: artificial
<220> FEATURE:
<223> OTHER INFORMATION: hybridization probe

<400> SEQUENCE: 425
cgacatgcgg tttttcgag cgtacgttgg tcgcatgtcg                  40

<210> SEQ ID NO 426
<211> LENGTH: 23
<212> TYPE: DNA
<213> ORGANISM: artificial
<220> FEATURE:
<223> OTHER INFORMATION: primer

<400> SEQUENCE: 426
cgttaggttt tgttgtttag cgt                                   23

<210> SEQ ID NO 427
<211> LENGTH: 23
<212> TYPE: DNA
<213> ORGANISM: artificial
<220> FEATURE:
<223> OTHER INFORMATION: primer

<400> SEQUENCE: 427
cgttaggttt tgttgtttag cgt                                   23

<210> SEQ ID NO 428
<211> LENGTH: 25
<212> TYPE: DNA
<213> ORGANISM: artificial
<220> FEATURE:
<223> OTHER INFORMATION: primer

<400> SEQUENCE: 428
gtttcgtagt ttagcgttag agcgt                                 25

<210> SEQ ID NO 429
<211> LENGTH: 25
<212> TYPE: DNA
<213> ORGANISM: artificial
<220> FEATURE:
<223> OTHER INFORMATION: primer

<400> SEQUENCE: 429
gtttcgtagt ttcgtagttt cgtag                                 25

<210> SEQ ID NO 430
<211> LENGTH: 20
<212> TYPE: DNA
<213> ORGANISM: artificial
<220> FEATURE:
<223> OTHER INFORMATION: primer

<400> SEQUENCE: 430
ggtcgttgtt atggacgttt                                       20
```

```
<210> SEQ ID NO 431
<211> LENGTH: 25
<212> TYPE: DNA
<213> ORGANISM: artificial
<220> FEATURE:
<223> OTHER INFORMATION: primer

<400> SEQUENCE: 431
ttcgttatat tttagtttag cgttt                                    25

<210> SEQ ID NO 432
<211> LENGTH: 22
<212> TYPE: DNA
<213> ORGANISM: artificial
<220> FEATURE:
<223> OTHER INFORMATION: primer

<400> SEQUENCE: 432
cgacacaact ttcctatcga cc                                       22

<210> SEQ ID NO 433
<211> LENGTH: 19
<212> TYPE: DNA
<213> ORGANISM: artificial
<220> FEATURE:
<223> OTHER INFORMATION: primer

<400> SEQUENCE: 433
aactttccta tcgaccgcc                                           19

<210> SEQ ID NO 434
<211> LENGTH: 23
<212> TYPE: DNA
<213> ORGANISM: artificial
<220> FEATURE:
<223> OTHER INFORMATION: primer

<400> SEQUENCE: 434
aaaacgaata cttcttaccg acc                                      23

<210> SEQ ID NO 435
<211> LENGTH: 21
<212> TYPE: DNA
<213> ORGANISM: artificial
<220> FEATURE:
<223> OTHER INFORMATION: primer

<400> SEQUENCE: 435
ttcttaccga cccaaaacgt a                                        21

<210> SEQ ID NO 436
<211> LENGTH: 24
<212> TYPE: DNA
<213> ORGANISM: artificial
<220> FEATURE:
<223> OTHER INFORMATION: primer

<400> SEQUENCE: 436
aaaattatac cgaacttatc gcct                                     24

<210> SEQ ID NO 437
<211> LENGTH: 19
<212> TYPE: DNA
<213> ORGANISM: artificial
<220> FEATURE:
```

<223> OTHER INFORMATION: primer

<400> SEQUENCE: 437
acacaaacct tcgtcgtcc                                          19

<210> SEQ ID NO 438
<211> LENGTH: 94
<212> TYPE: DNA
<213> ORGANISM: artificial
<220> FEATURE:
<223> OTHER INFORMATION: synthetic construct

<400> SEQUENCE: 438
cgttaggttt tgttgtttag cgtcgtaacg ggttcggttt ttggcgtttt cgaattttg      60 tgttttggcg gcggtcgata ggaaagttgt gtcg                                 94

<210> SEQ ID NO 439
<211> LENGTH: 88
<212> TYPE: DNA
<213> ORGANISM: artificial
<220> FEATURE:
<223> OTHER INFORMATION: synthetic construct

<400> SEQUENCE: 439
cgttaggttt tgttgtttag cgtcgtaacg ggttcggttt ttggcgtttt cgaattttg      60 tgttttggcg gcggtcgata ggaaagtt                                        88

<210> SEQ ID NO 440
<211> LENGTH: 80
<212> TYPE: DNA
<213> ORGANISM: artificial
<220> FEATURE:
<223> OTHER INFORMATION: synthetic construct

<400> SEQUENCE: 440
gtttcgtagt ttagcgttag agcgttgcgc ggagattttt tgtcgtcgta cgttttgggt     60
cggtaagaag tattcgtttt                                                 80

<210> SEQ ID NO 441
<211> LENGTH: 85
<212> TYPE: DNA
<213> ORGANISM: artificial
<220> FEATURE:
<223> OTHER INFORMATION: synthetic construct

<400> SEQUENCE: 441
gtttcgtagt ttcgtagttt cgtagtttag cgttagagcg ttgcgcggag atttttttgtc    60 gtcgtacgtt ttgggtcggt aagaa                                           85

<210> SEQ ID NO 442
<211> LENGTH: 102
<212> TYPE: DNA
<213> ORGANISM: artificial
<220> FEATURE:
<223> OTHER INFORMATION: synthetic construct

<400> SEQUENCE: 442
ggtcgttgtt atggacgttt attatagttc ggtgtcgtag agtcgggagg gttcgtcgtt     60
ttttagggta tttttcggag gcgataagtt cggtataatt tt                       102

<210> SEQ ID NO 443
<211> LENGTH: 92

-continued

```
<212> TYPE: DNA
<213> ORGANISM: artificial
<220> FEATURE:
<223> OTHER INFORMATION: synthetic construct

<400> SEQUENCE: 443
ttcgttatat tttagtttag cgttttttata gtagagggaa atagttaata agacgtgtaa      60
gtgattatgt attggacgac gaaggtttgt gt                                    92

<210> SEQ ID NO 444
<211> LENGTH: 94
<212> TYPE: DNA
<213> ORGANISM: Homo sapiens

<400> SEQUENCE: 444
cgccaggtcc tgctgcccag cgccgtaacg ggcccggctc ttggcgtccc cgaatccctg      60
tgctttggcg gcggccgaca ggaaagttgt gccg                                  94

<210> SEQ ID NO 445
<211> LENGTH: 88
<212> TYPE: DNA
<213> ORGANISM: Homo sapiens

<400> SEQUENCE: 445
cgccaggtcc tgctgcccag cgccgtaacg ggcccggctc ttggcgtccc cgaatccctg      60
tgctttggcg gcggccgaca ggaaagtt                                         88

<210> SEQ ID NO 446
<211> LENGTH: 80
<212> TYPE: DNA
<213> ORGANISM: Homo sapiens

<400> SEQUENCE: 446
gccccgcagc ccagcgccag agcgctgcgc ggagactcct tgccgccgca cgccctgggc      60
cggtaagaag catccgcttc                                                  80

<210> SEQ ID NO 447
<211> LENGTH: 85
<212> TYPE: DNA
<213> ORGANISM: Homo sapiens

<400> SEQUENCE: 447
gccccgcagc cccgcagccc cgcagcccag cgccagagcg ctgcgcggag actccttgcc      60
gccgcacgcc ctgggccggt aagaa                                            85

<210> SEQ ID NO 448
<211> LENGTH: 102
<212> TYPE: DNA
<213> ORGANISM: Homo sapiens

<400> SEQUENCE: 448
ggccgctgcc atggacgcct actacagccc ggtgtcgcag agtcgggagg gctcgtcgcc      60
ttttagggca tttcccggag gcgacaagtt cggcacaact tt                        102

<210> SEQ ID NO 449
<211> LENGTH: 92
<212> TYPE: DNA
<213> ORGANISM: Homo sapiens

<400> SEQUENCE: 449
```

```
tccgctacat cccagcccag cgcccttaca gcagagggaa atagttaaca agacgtgcaa        60
gtgaccatgc actggacgac gaaggcttgt gt                                     92
```